(12) United States Patent
Samsoondar

(10) Patent No.: US 11,327,084 B2
(45) Date of Patent: May 10, 2022

(54) JOINT HEMATOLOGY AND BIOCHEMISTRY POINT-OF-CARE TESTING SYSTEM

(71) Applicant: INVIDX CORP., Markham (CA)

(72) Inventor: James Samsoondar, Markham (CA)

(73) Assignee: INVIDX CORP., Schomberg (CA)

( * ) Notice: Subject to any disclaimer, the term of this patent is extended or adjusted under 35 U.S.C. 154(b) by 39 days.

(21) Appl. No.: 16/575,645

(22) Filed: Sep. 19, 2019

(65) Prior Publication Data

US 2021/0088534 A1   Mar. 25, 2021

(51) Int. Cl.
*G01N 33/80* (2006.01)
*G01N 33/569* (2006.01)
(Continued)

(52) U.S. Cl.
CPC ............ *G01N 33/80* (2013.01); *G01N 33/49* (2013.01); *G01N 33/555* (2013.01);
(Continued)

(58) Field of Classification Search
CPC ............ G01N 33/80; G01N 33/56972; G01N 33/555; G01N 33/49; G01N 2496/05; G01N 2496/15; G01N 33/86; G01N 2021/0346; G01N 21/03; G01N 15/05; G01N 15/12; G01N 15/1484; G01N 2015/045; G01N 2800/22; G01N 33/52; G01N 33/72; B01L 2300/0816; B01L 2400/0481; B01L 2400/0487; B01L 2300/0867; B01L 2200/0605; B01L 2200/027;
(Continued)

(56) References Cited

U.S. PATENT DOCUMENTS

| 2,656,508 A | 10/1953 | Coulter |
| 5,112,455 A | 5/1992 | Cozzette et al. |

(Continued)

FOREIGN PATENT DOCUMENTS

| CA | 2709456 A1 * | 7/2009 | .......... B01J 19/0046 |
| CA | 2911318 A1 | 11/2015 | |

(Continued)

OTHER PUBLICATIONS

Thefreedictionary.com definition of "slot".*
(Continued)

*Primary Examiner* — Mohamed K Amara
(74) *Attorney, Agent, or Firm* — Bereskin & Parr LLP/S.E.N.C.R.L., s.r.l.

(57) ABSTRACT

A joint point-of-care testing (POCT) analyzer, and a system comprising an analyzer and a cartridge, for measuring one or more analyte quantities per unit volume of blood and one or more formed element quantities per unit volume of blood, is described. Examples of formed elements of blood are red blood cells and white blood cells, and cell counts are determined by imaging using a two-dimensional multi-channel detector. Examples of analytes are hemoglobin and bilirubin, and hemoglobin and bilirubin concentrations are determined by spectroscopy using a one-dimensional multi-channel detector. Other examples of analytes are electrolytes, and electrolyte concentrations may be determined using biosensors incorporated in the cartridges.

36 Claims, 21 Drawing Sheets

(51) Int. Cl.
*G01N 33/555* (2006.01)
*G01N 33/49* (2006.01)

(52) U.S. Cl.
CPC ... *G01N 33/56972* (2013.01); *G01N 2496/05* (2013.01); *G01N 2496/15* (2013.01)

(58) Field of Classification Search
CPC ..... B01L 2300/0887; B01L 2300/0654; B01L 2300/027; B01L 2300/069; B01L 2300/0819; B01L 2400/049; B01L 3/502784; A61B 5/150229; A61K 39/395; G01J 2003/2866; G01J 3/433
See application file for complete search history.

(56) References Cited

U.S. PATENT DOCUMENTS

| | | | | |
|---|---|---|---|---|
| 5,793,485 | A * | 8/1998 | Gourley | G01N 15/1429 356/318 |
| 5,821,399 | A | 10/1998 | Zelin | |
| 5,885,840 | A * | 3/1999 | Kamentsky | G01N 15/1475 436/63 |
| 6,198,532 | B1 * | 3/2001 | Cabib | A61B 5/14555 250/461.2 |
| 6,372,503 | B1 | 4/2002 | Samsoondar | |
| 6,651,015 | B2 | 11/2003 | Samsoondar | |
| 6,711,516 | B2 | 3/2004 | Samsoondar | |
| 6,743,576 | B1 * | 6/2004 | Sabry | G06K 9/00127 435/4 |
| 7,139,415 | B2 * | 11/2006 | Finkbeiner | G01N 21/253 382/128 |
| 7,521,243 | B2 | 4/2009 | Lindberg et al. | |
| 7,547,904 | B2 * | 6/2009 | Schmidt | B01L 3/502715 250/573 |
| 7,553,453 | B2 * | 6/2009 | Gu | B01L 3/502776 422/537 |
| 7,682,833 | B2 * | 3/2010 | Miller | B01L 3/502707 436/165 |
| 7,738,094 | B2 * | 6/2010 | Goldberg | G01N 21/6428 356/246 |
| 7,745,221 | B2 * | 6/2010 | Butler | B01L 3/502761 436/63 |
| 7,852,490 | B2 * | 12/2010 | Kiesel | A61B 5/1459 356/519 |
| 7,887,750 | B2 * | 2/2011 | Blatt | G01N 21/8483 422/423 |
| 8,206,650 | B2 | 6/2012 | Samsoondar | |
| 8,216,529 | B2 * | 7/2012 | Ade | B29C 66/1122 422/547 |
| 8,320,983 | B2 * | 11/2012 | Martini | A61B 5/1459 600/316 |
| 8,634,607 | B2 * | 1/2014 | Levenson | G01J 3/453 382/128 |
| 8,797,527 | B2 * | 8/2014 | Hukari | B01L 3/502738 356/246 |
| 9,063,117 | B2 * | 6/2015 | Gourley | G01N 33/574 |
| 9,470,673 | B2 | 10/2016 | Samsoondar | |
| 9,767,343 | B1 * | 9/2017 | Jones | B01L 3/502715 |
| 9,821,307 | B2 | 11/2017 | Samsoondar | |
| 9,976,973 | B2 * | 5/2018 | Watkins | G01N 33/56972 |
| 9,999,884 | B2 | 6/2018 | Samsoondar | |
| 10,018,640 | B2 * | 7/2018 | Bornheimer | G01N 33/721 |
| 10,024,855 | B2 * | 7/2018 | Kasdan | G01N 33/68 |
| 10,272,430 | B2 | 4/2019 | Samsoondar | |
| 10,408,995 | B1 * | 9/2019 | Dong | G02B 6/0208 |
| 10,527,568 | B2 * | 1/2020 | Watkins | G01N 15/12 |
| 10,761,094 | B2 * | 9/2020 | Kasdan | G01N 21/75 |
| 10,876,956 | B2 * | 12/2020 | Nugent | C12Q 1/6806 |
| 10,900,885 | B2 * | 1/2021 | Yamamoto | G01N 15/1459 |
| 2003/0215791 | A1 * | 11/2003 | Garini | G01N 33/54306 435/5 |
| 2004/0233543 | A1 * | 11/2004 | Chang | G02B 26/125 359/686 |
| 2005/0054078 | A1 | 3/2005 | Miller | |
| 2005/0105077 | A1 * | 5/2005 | Padmanabhan | A61B 5/150221 356/39 |
| 2005/0181383 | A1 * | 8/2005 | Su | C12Q 1/6869 435/6.18 |
| 2005/0249633 | A1 * | 11/2005 | Blatt | B01L 3/5027 422/400 |
| 2006/0068412 | A1 * | 3/2006 | Tang | G01N 33/54373 435/6.11 |
| 2006/0097176 | A1 * | 5/2006 | Szu | A61B 5/0059 250/370.08 |
| 2006/0209413 | A1 * | 9/2006 | Kim | G02B 5/284 359/577 |
| 2006/0238866 | A1 * | 10/2006 | Von Lerber | H04B 10/299 359/485.06 |
| 2008/0006535 | A1 * | 1/2008 | Paik | B01L 3/502792 204/600 |
| 2008/0260225 | A1 * | 10/2008 | Szu | G01J 3/36 382/128 |
| 2009/0215072 | A1 * | 8/2009 | McDevitt | G01N 33/56972 435/7.1 |
| 2010/0120083 | A1 | 5/2010 | Ritzen et al. | |
| 2011/0201045 | A1 | 8/2011 | Levine et al. | |
| 2011/0251075 | A1 * | 10/2011 | McDevitt | B01L 3/5025 506/7 |
| 2012/0071342 | A1 * | 3/2012 | Lochhead | G01N 21/6452 506/9 |
| 2012/0258472 | A1 * | 10/2012 | Roy | G01N 35/1002 435/7.9 |
| 2013/0161190 | A1 * | 6/2013 | Ewart | G01N 27/27 204/403.03 |
| 2016/0169801 | A1 * | 6/2016 | Rogacs | C12Q 1/6825 506/9 |
| 2017/0059477 | A1 * | 3/2017 | Feitisch | G01N 21/274 |
| 2017/0144146 | A1 | 5/2017 | Samsoondar | |
| 2017/0341077 | A1 * | 11/2017 | Neethirajan | G01N 33/5308 |
| 2017/0355637 | A1 * | 12/2017 | Nomura | G02B 5/208 |
| 2018/0120575 | A1 * | 5/2018 | Chen | G02B 27/16 |
| 2018/0219302 | A1 * | 8/2018 | Vella | H01L 51/00 |
| 2018/0272342 | A1 * | 9/2018 | Samsoondar | B01L 3/502784 |
| 2019/0054466 | A1 * | 2/2019 | Gershtein | G01N 15/1436 |
| 2019/0056304 | A1 * | 2/2019 | Gershtein | G01N 15/1404 |
| 2019/0224667 | A1 | 7/2019 | Samsoondar | |
| 2020/0290035 | A1 | 9/2020 | Samsoondar | |

FOREIGN PATENT DOCUMENTS

| | | |
|---|---|---|
| CA | 2978737 | 10/2018 |
| WO | 2010/070521 A1 | 6/2010 |
| WO | 2018/209418 A1 | 11/2018 |

OTHER PUBLICATIONS

Zhang, Chu et al. Mid-Infrared Spectroscopy for Coffee Variety Identification: Comparison of Pattern Recognition Methods, J. of Spectroscopy, vol. 2016, Article ID 7927286, pp. 1-8.

G. O. Gogstad et al., "Turbidimetric Determination of Prothrombin Time by Clotting in a Centrifugal Analyzer" Clin. Chem. 32/10, 1857-1862, 1986.

Written Opinion and International Search Report dated Nov. 30, 2021 in respect of PCT/CA2021/051289.

* cited by examiner

FIG. 1A (Prior Art)
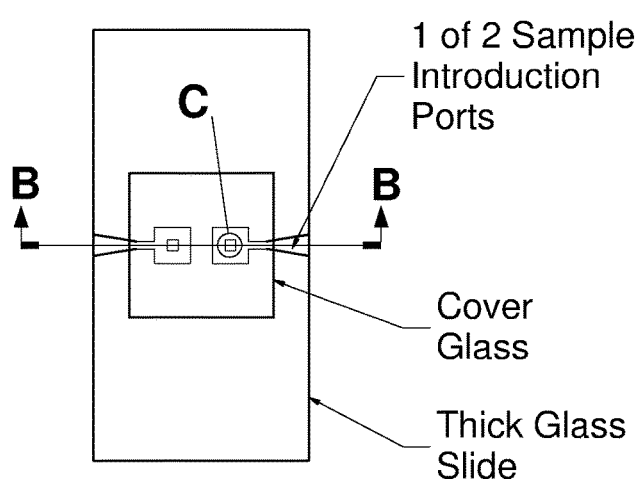
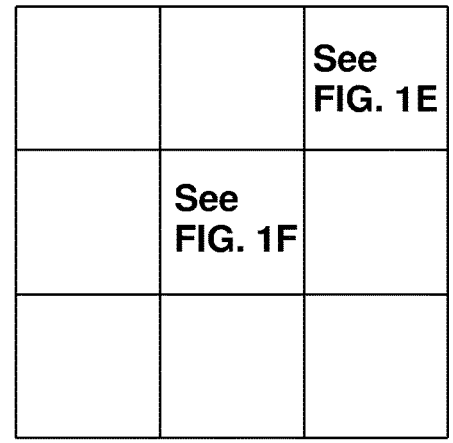
FIG. 1B
FIG. 1C
FIG. 1D
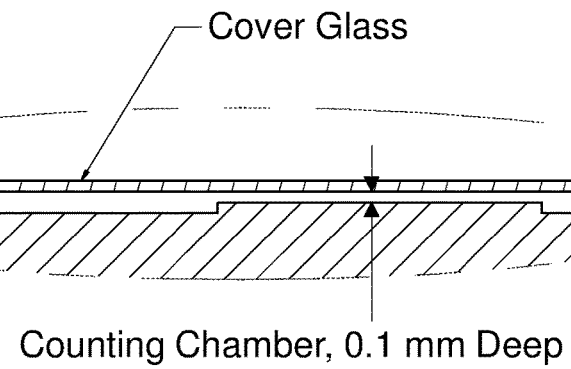
Counting Chamber, 0.1 mm Deep
FIG. 1E
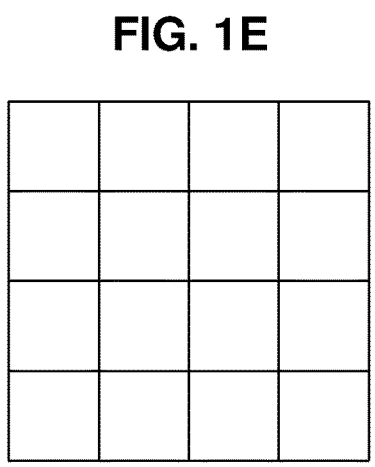
0.25 mm
FIG. 1F
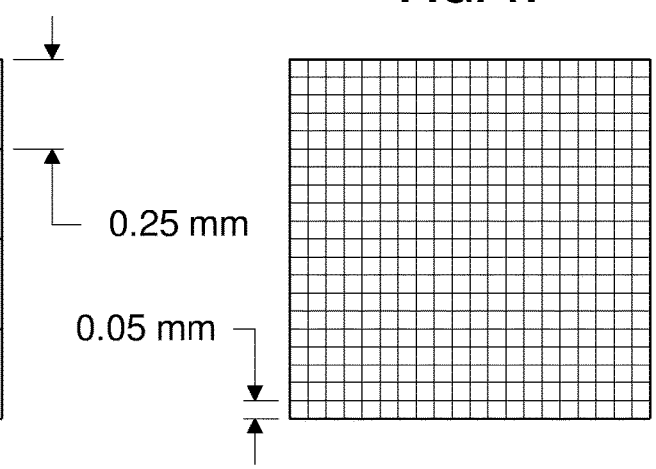
0.05 mm

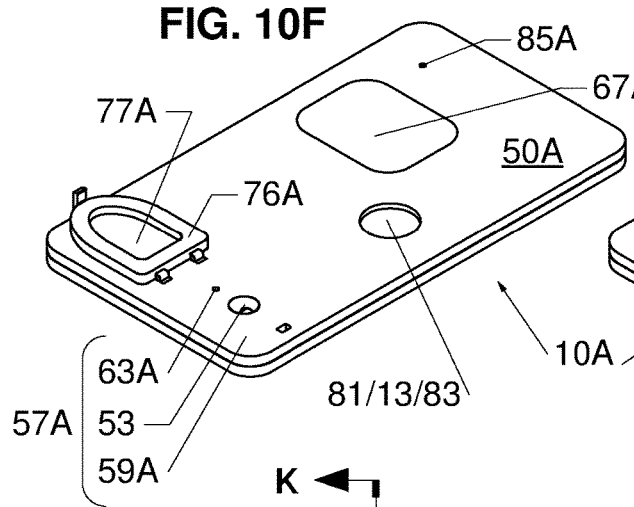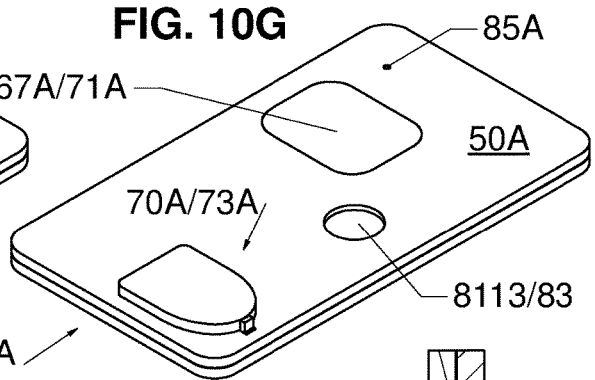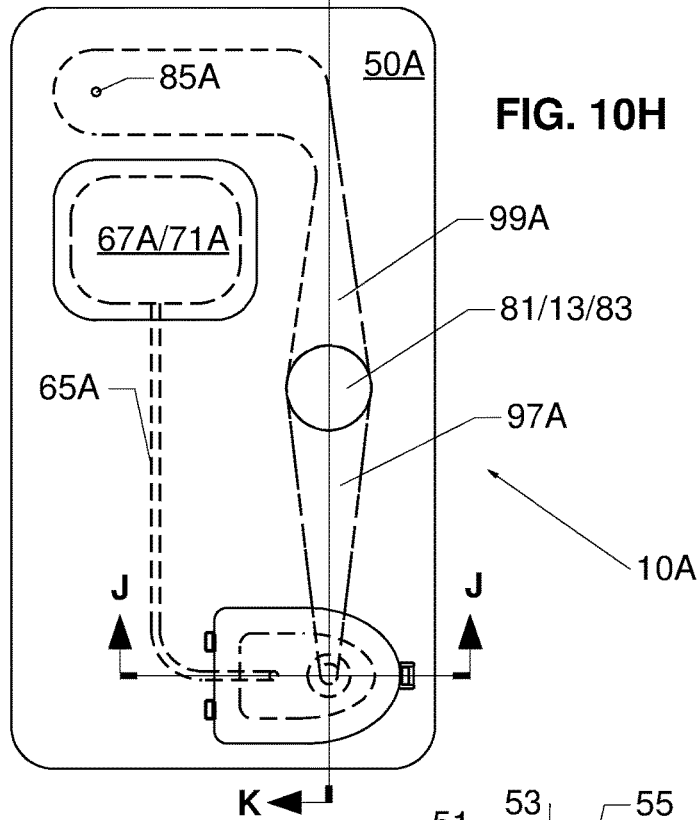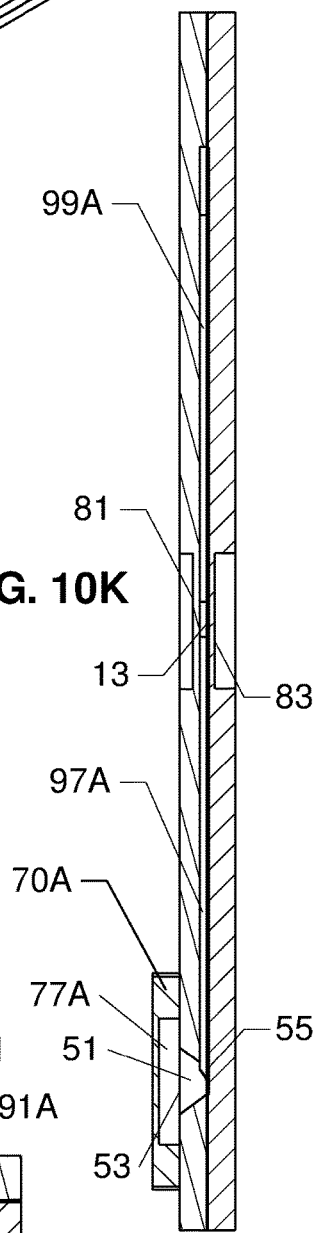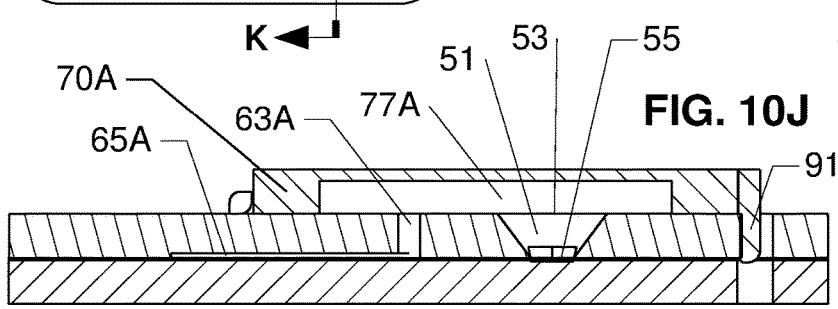

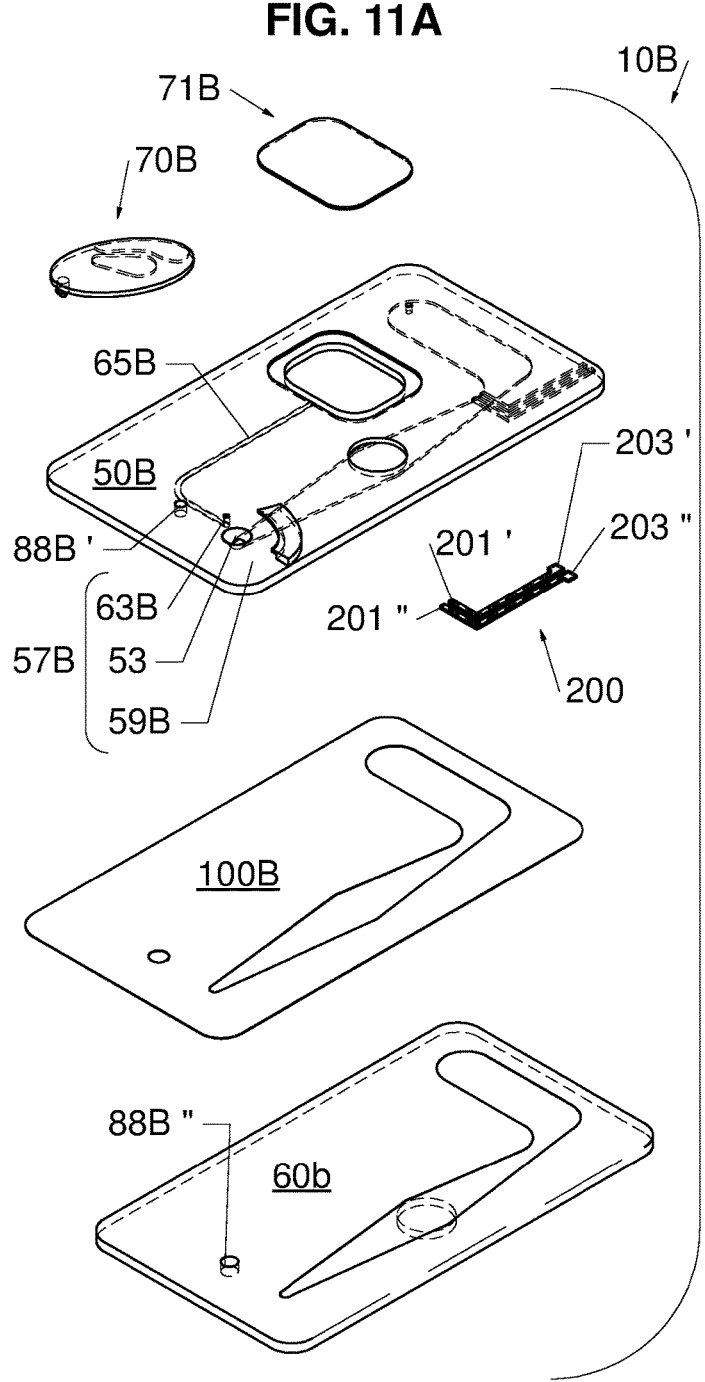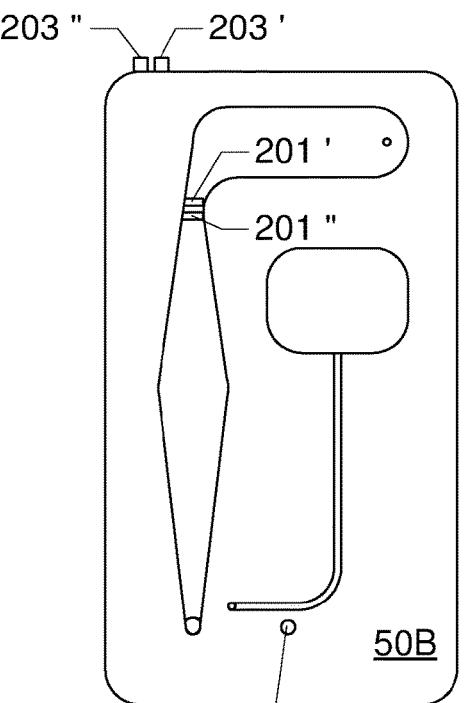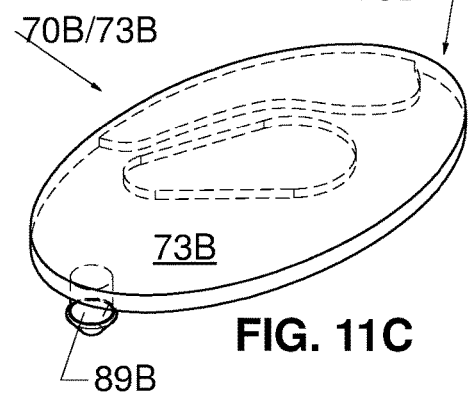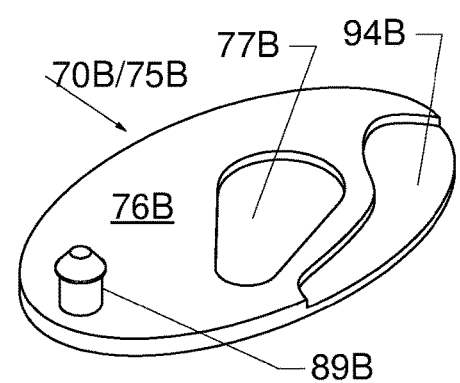

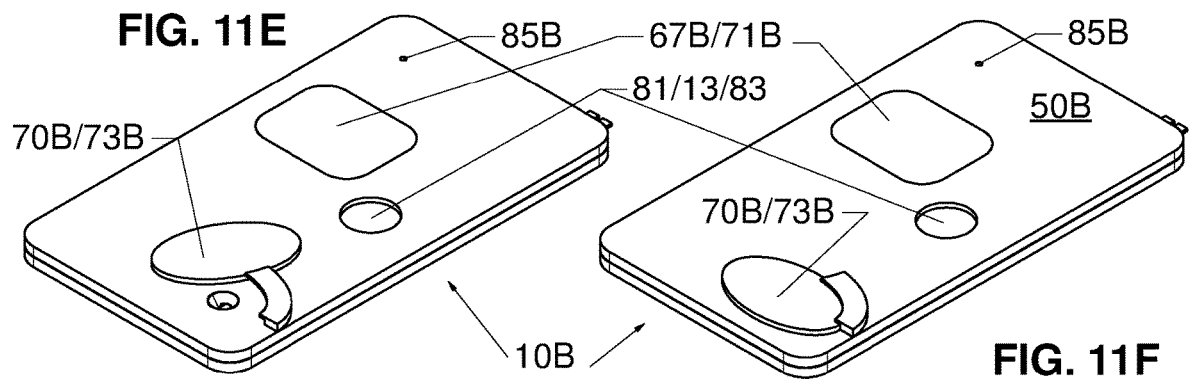
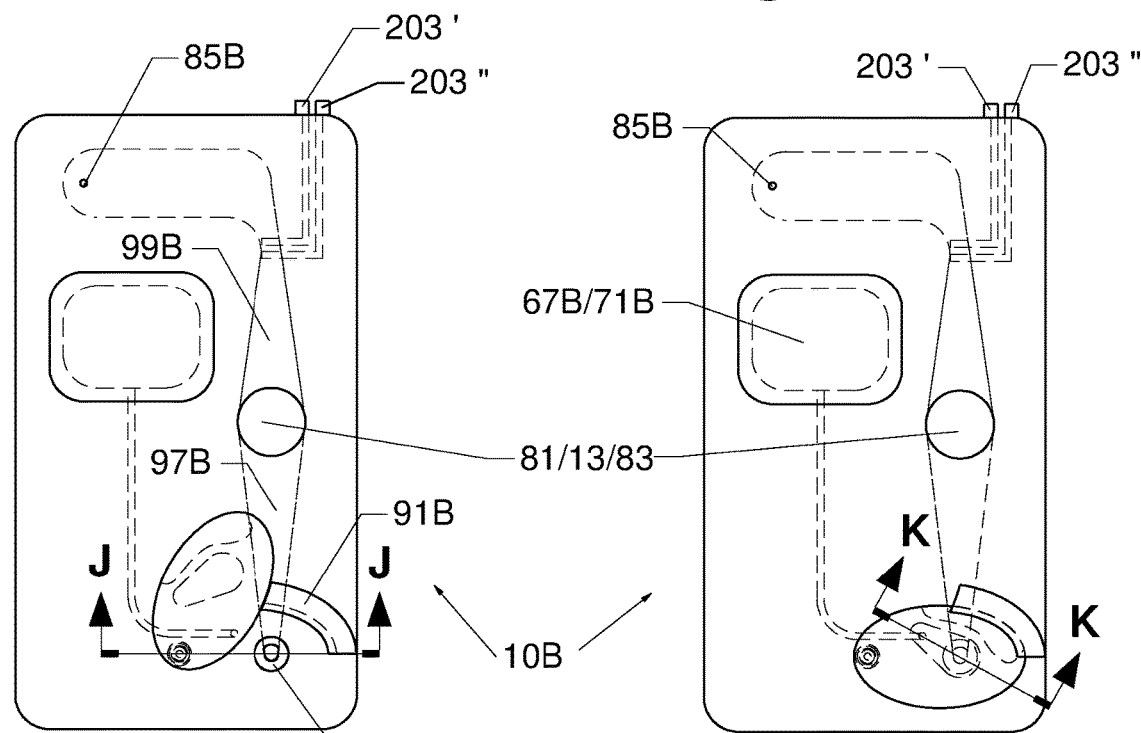
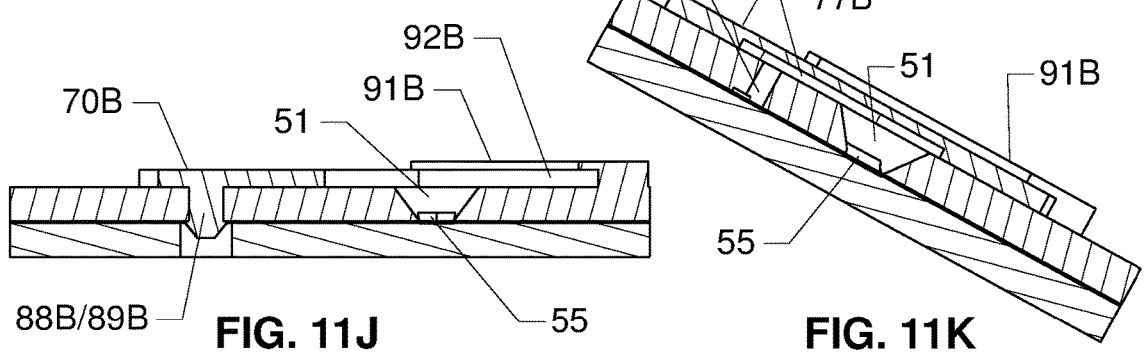

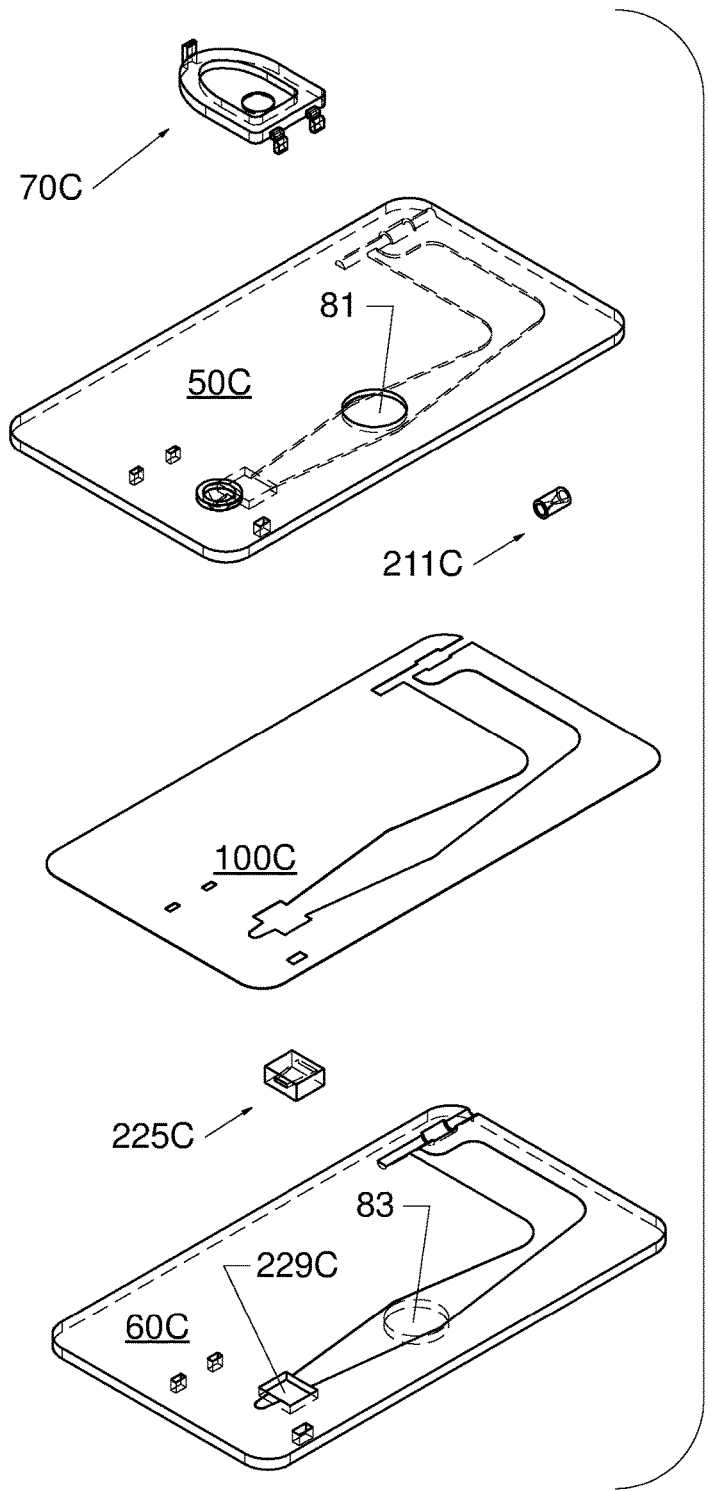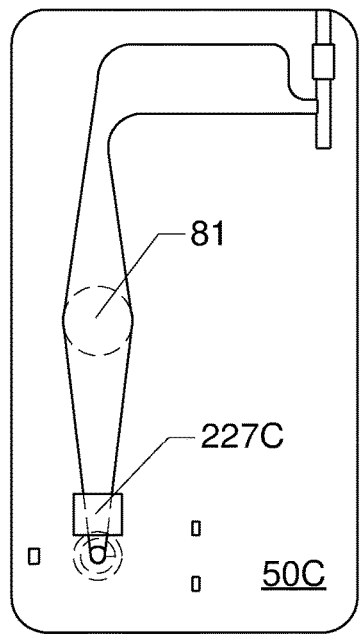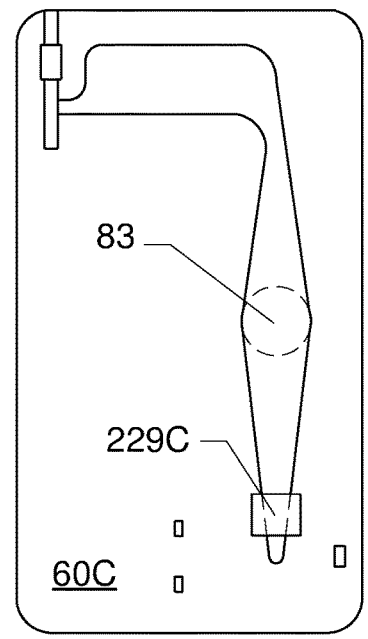
FIG. 12A
FIG. 12B
FIG. 12C

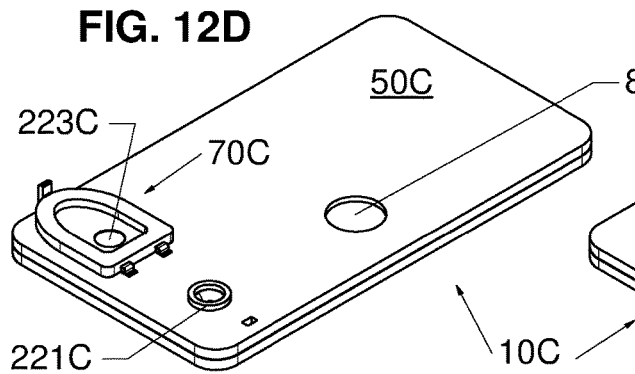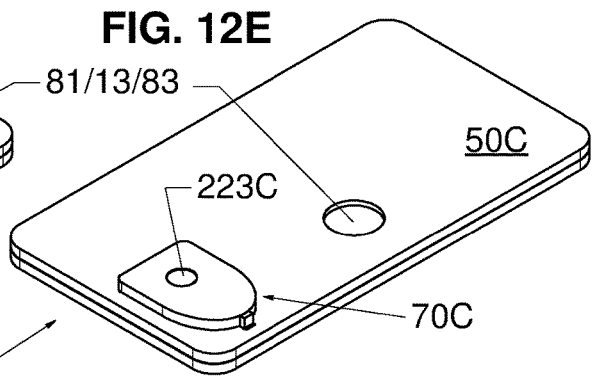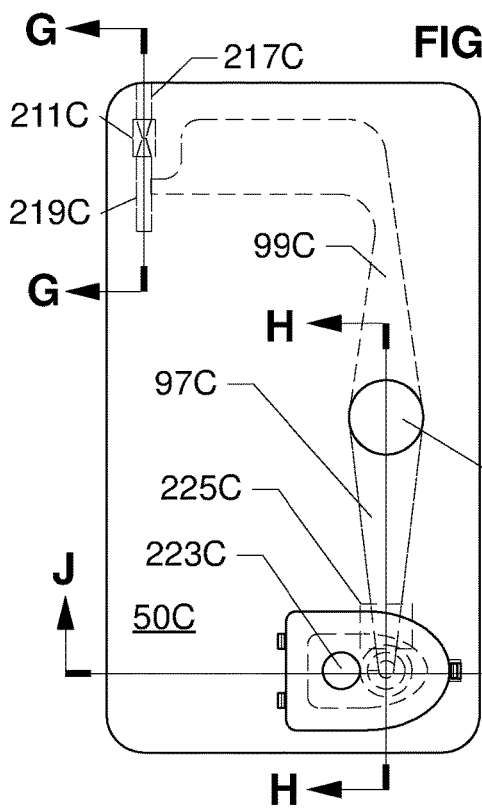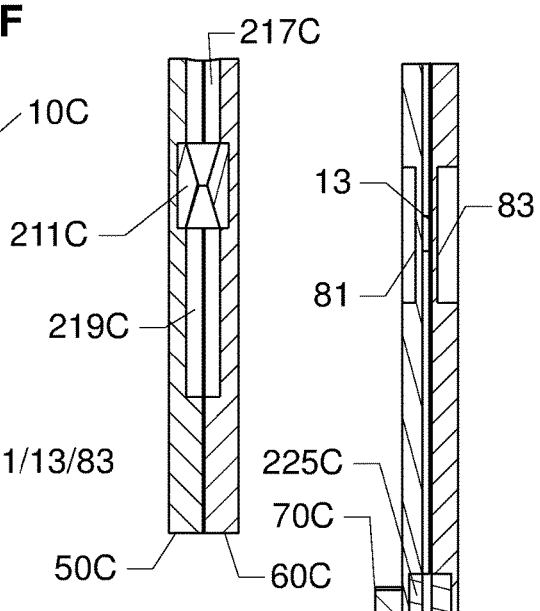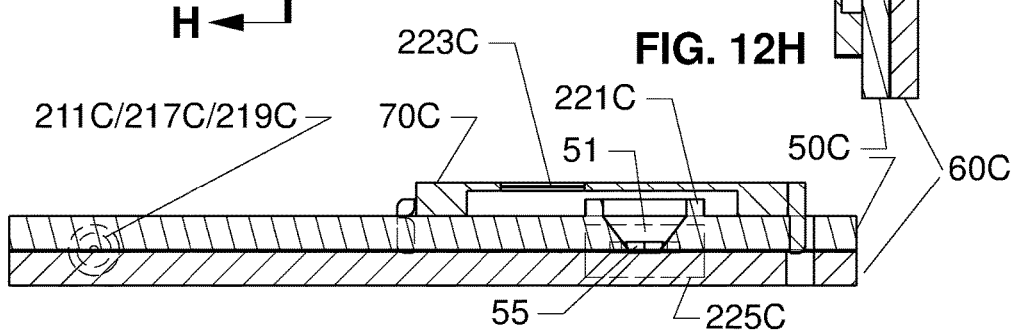

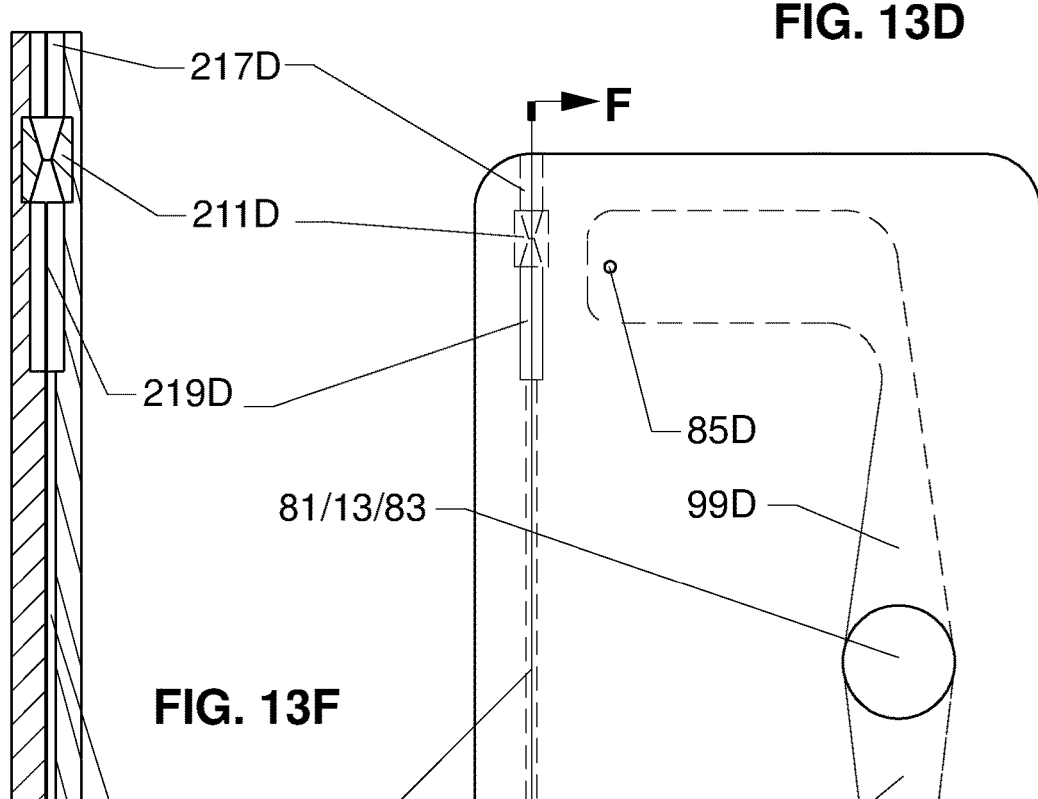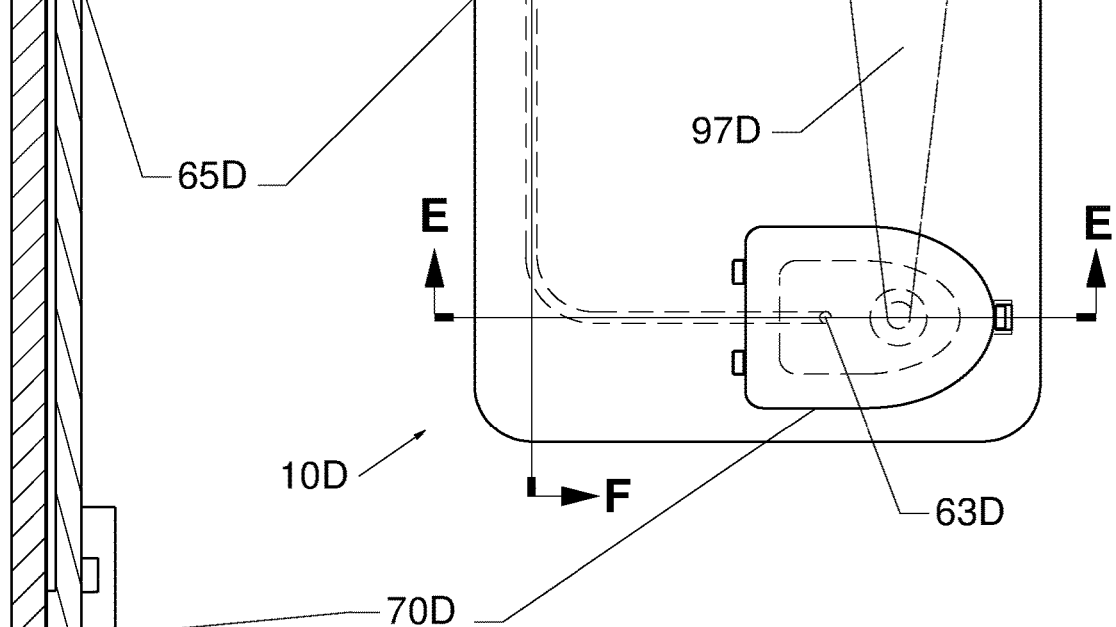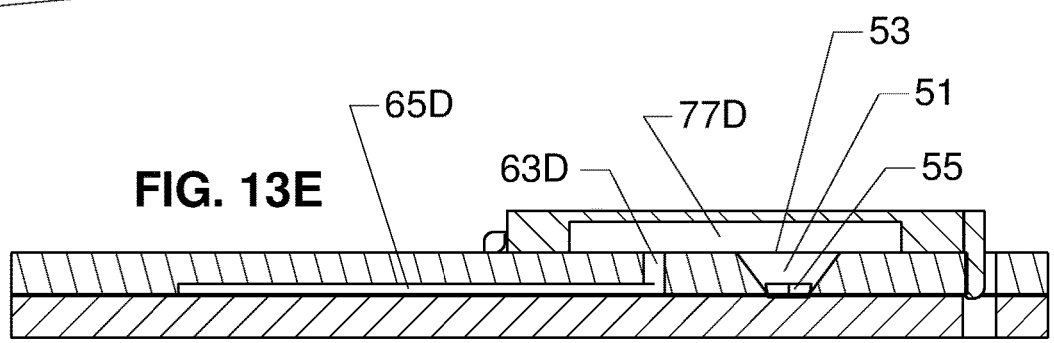

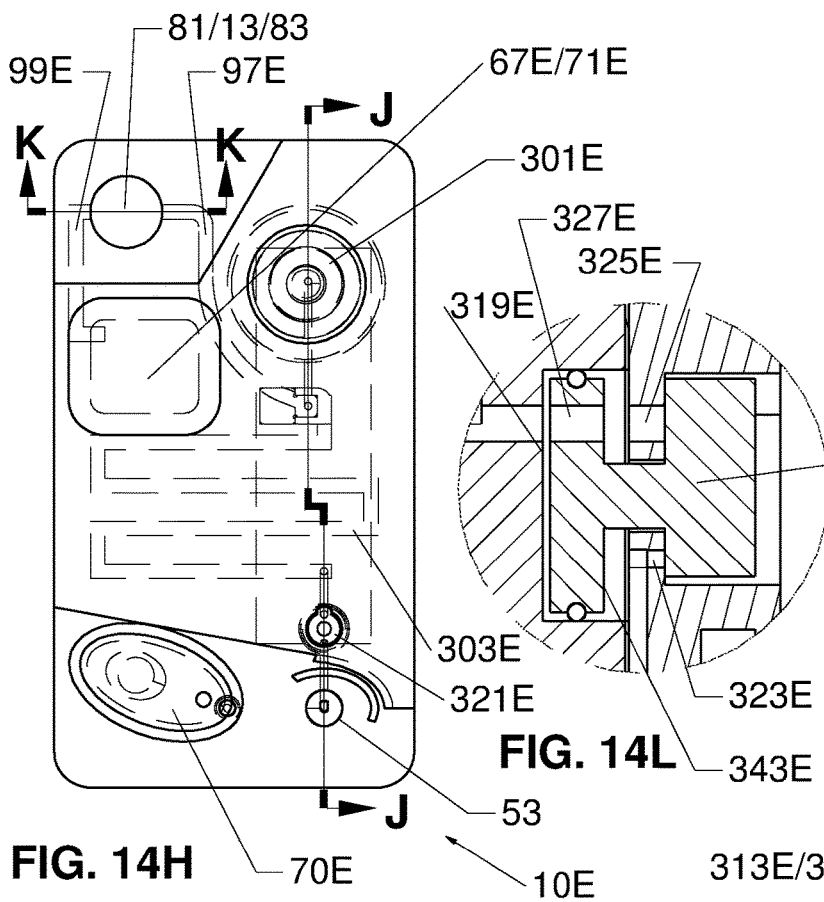
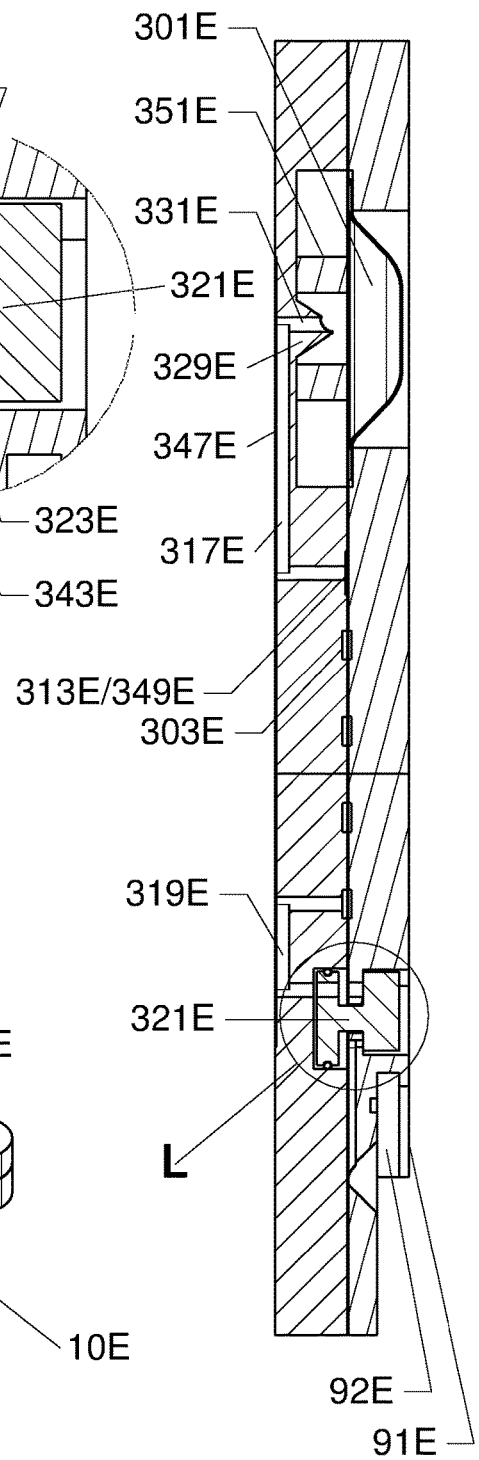
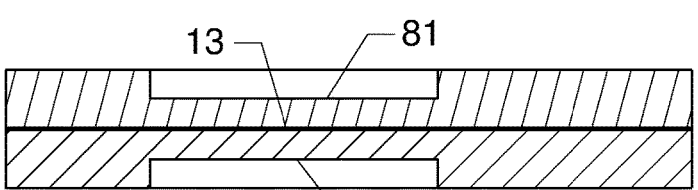
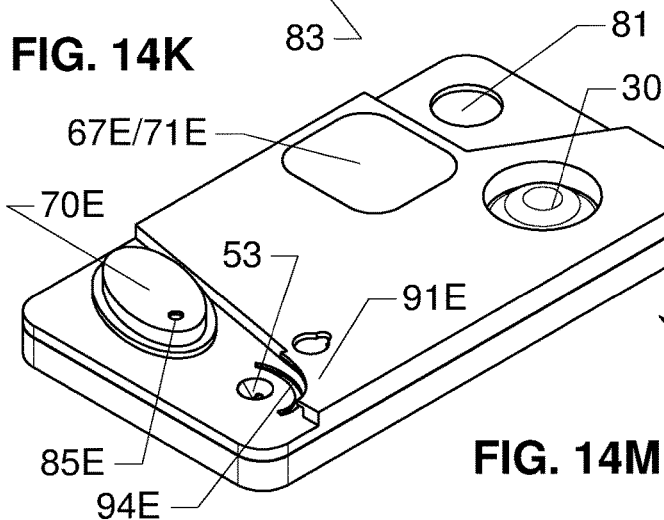

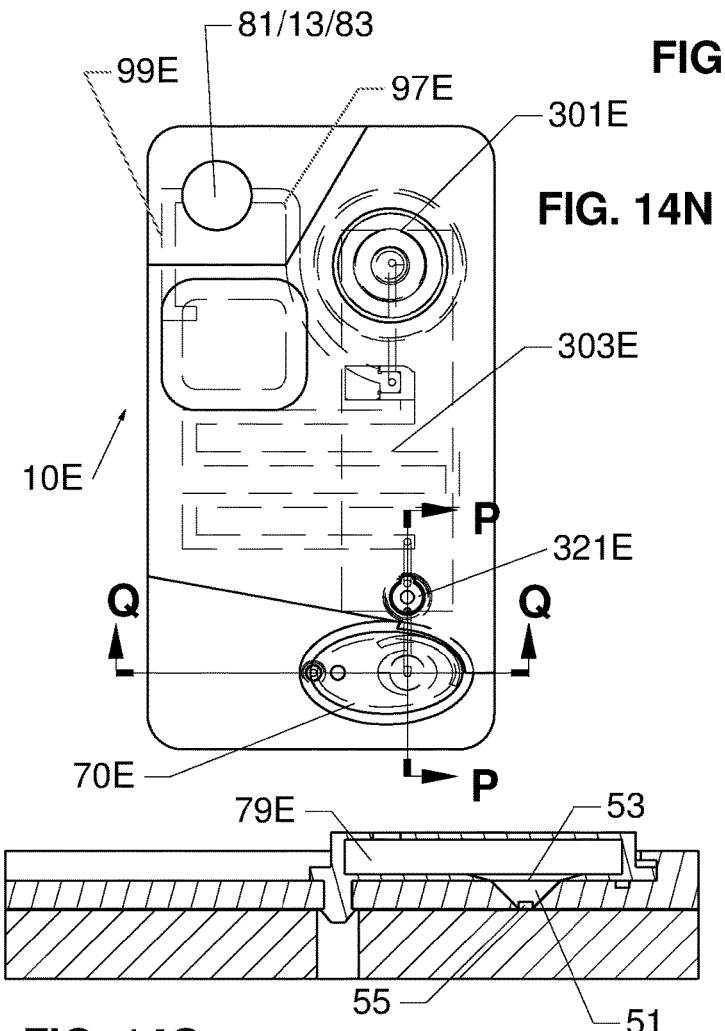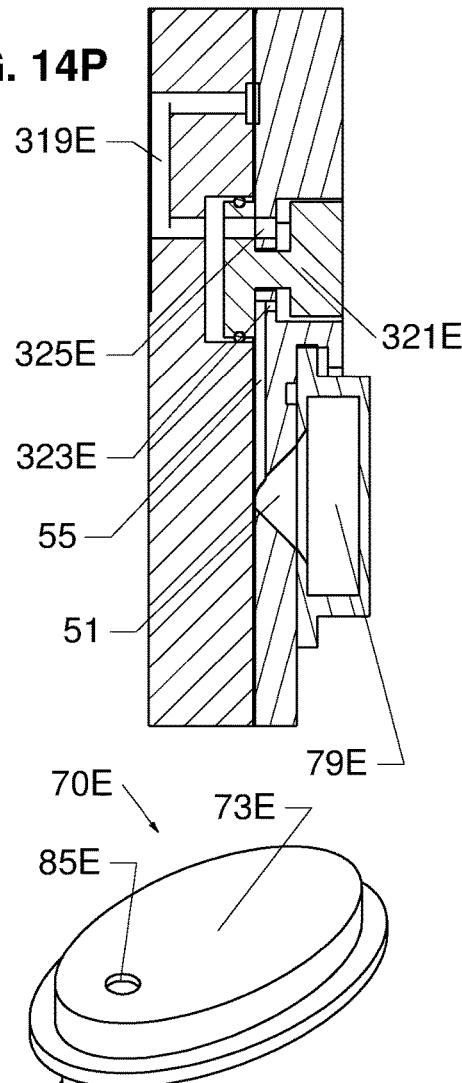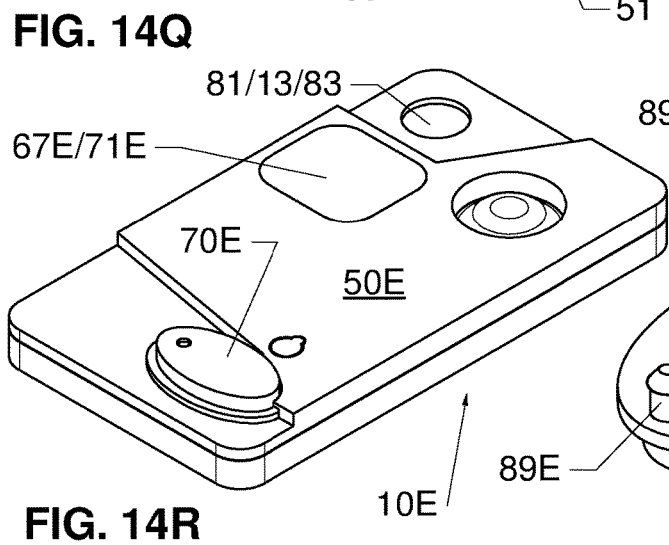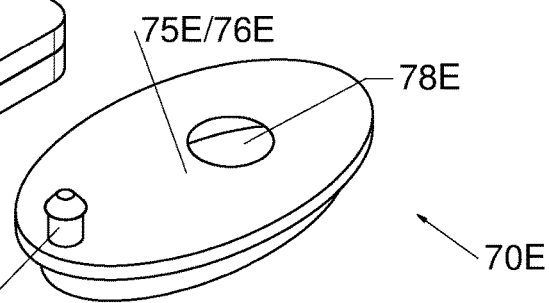

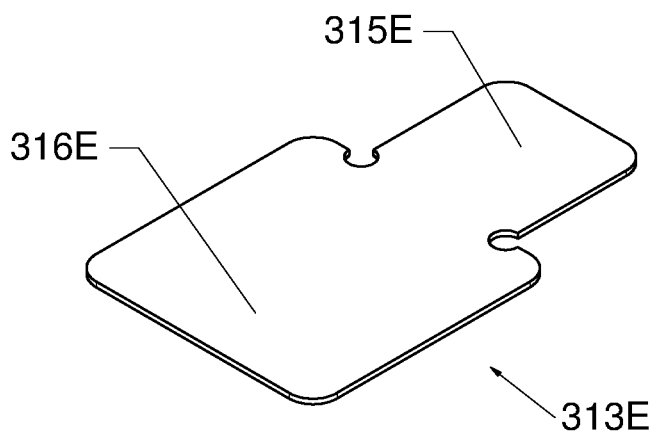
FIG. 14U
FIG. 14V
FIG. 14W
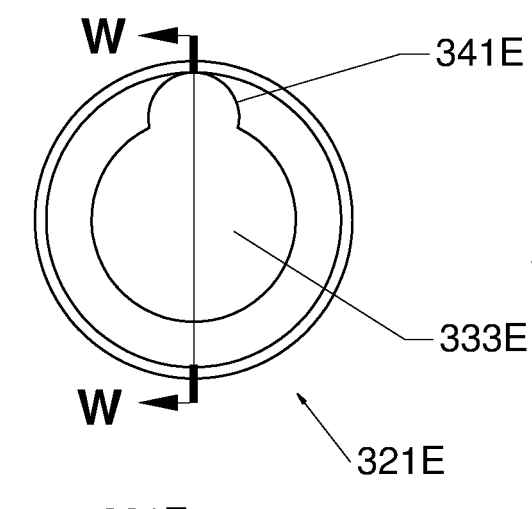
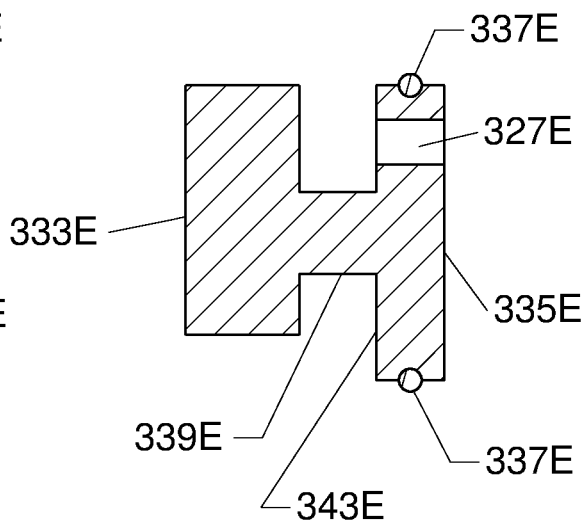
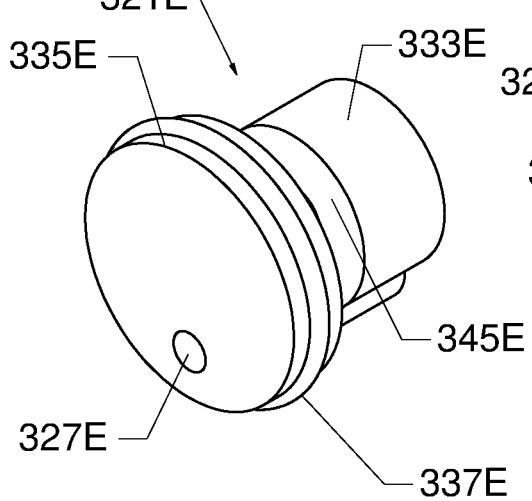
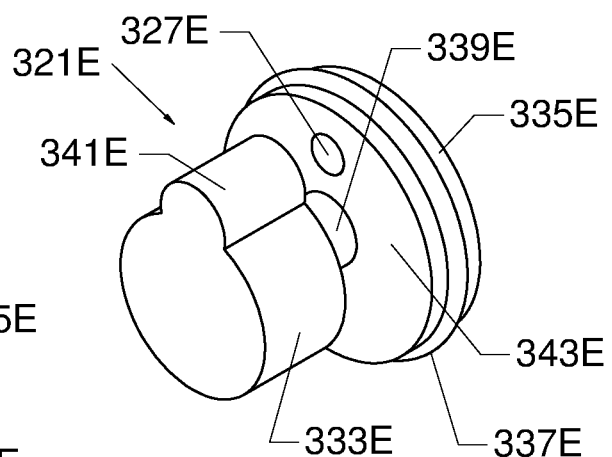
FIG. 14X
FIG. 14Y

JOINT HEMATOLOGY AND BIOCHEMISTRY POINT-OF-CARE TESTING SYSTEM

FIELD OF THE INVENTION

The invention relates to a point-of-care testing (POCT) system that consolidates analytical tests in a single analyzer.

BACKGROUND OF THE INVENTION

The result of reaction between a liquid sample and one or more reagent depends on the quantity of the one or more reagent and the volume of liquid sample. Although any type of liquid sample is implied, serum, plasma and blood (also referred to as whole blood) are samples of particular interest. The reagent is preferably in a dry form, in order to avoid dilution of the sample. When blood is allowed to clot and the sample is centrifuged, the yellow liquid that sits on top of the blood clot is called serum. If the blood is collected in a tube containing an anticoagulant, for example heparin, and the blood centrifuged, the cells and cell fragments, referred to as formed elements, are separated from a yellow liquid called plasma, which sits on top of the formed elements. The plasma is usually about 90 percent water, in which the formed elements are usually suspended, and it transports nutrients as well as wastes throughout the body. Various analytes are dissolved in the plasma for example, glucose, electrolytes, blood gases, drugs, hormones, lipids, enzymes (e.g., ALT, which may be used for assessing liver function), and metabolites (e.g., creatinine which may be used for assessing kidney function, and lactate which may be used for detecting sepsis).

The formed elements are cells and cell fragments suspended in the plasma. Because the formed elements are heavier than the liquid matrix, they are packed in the bottom of the collection tube by the centrifugal force. The plasma accounts for about 55 percent of the blood volume. The volume of the red blood cells is called the hematocrit, or packed cell volume (PCV). The white blood cells and platelets form a thin white layer, called the "buffy coat", disposed between the plasma and the red blood cells. The classes of the formed elements are: erythrocytes (red blood cells or RBCs), leukocytes (white blood cells), and thrombocytes (platelets). Erythrocytes are the most numerous of the formed elements. Erythrocytes are tiny biconcave disks, thin in the middle and thicker around the periphery. A normal erythrocyte has a diameter of about 6-8 micrometers (μm). The shape provides a combination of flexibility for moving through tiny capillaries with a maximum surface area for the diffusion of gases. The primary function of erythrocytes is to transport oxygen to body tissue and, to transport carbon dioxide to the lungs where the carbon dioxide is expelled through the nose and mouth. Since only the erythrocytes contain hemoglobin, total hemoglobin concentration is highly correlated with hematocrit, except in cases of for example, macrocytic anemia where the mean red cell hemoglobin concentration is lower than that of a normal red cell.

Leukocytes, or white blood cells, are generally larger than erythrocytes, but they are fewer in number. An average diameter of a leukocyte is about 12-17 μm. Leukocytes use the blood as a transport medium to other tissues, where they participate in defense against organisms that cause disease and either promote or inhibit inflammatory responses. Some leukocytes are phagocytic, others produce antibodies, and some secrete histamine and heparin. Leukocytes are able to move through the capillary walls into the extravascular tissue spaces, a process called diapedesis.

There are two main groups of leukocytes in the blood. The cells that develop granules in the cytoplasm are called granulocytes (and include neutrophils, eosinophils, and basophils) and those that do not have granules are called agranulocytes (and include monocytes and lymphocytes). This classification depends on whether granules can be distinguished in their cytoplasm, using a light microscope and conventional staining techniques.

Neutrophils are the commonest type of leukocytes found in blood, making up 60-70% of the total amount of leukocytes. The neutrophils are 12-14 μm in diameter. Neutrophils comprise a single nucleus, which is multilobed, and the number of lobes can be between 2 and 5.

Eosinophils make up 1-6% of the total leukocytes. Eosinophils are 12-17 μm in diameter, and the nucleus comprises two lobes. Eosinophils have large acidophilic specific granules that stain bright red, or reddish-purple.

Basophils are the rarest type of leukocytes, making up only 0.5-1% of the leukocytes in blood. Basophil are 14-16 μm in diameter, contain deep blue staining granules (basic) and the nucleus comprises two lobes. The granules contain heparin, histamine, serotonin, prostaglandins and leukotrienes. In the extravascular tissues, they are called mast cells.

Lymphocytes are the second most common leukocytes, making up 20-50% leukocytes in blood. Lymphocytes are agranulocytes that have a special role in immune processes. Some attack bacteria directly, and some produce antibodies. Most of the lymphocytes are 6-9 μm in diameter. About 10% are larger, having a diameter of 10-14 μm. These larger cells have more cytoplasm, more free ribosomes and mitochondria. Lymphocytes can look like monocytes, except that lymphocytes do not have a kidney-bean shaped nucleus like the monocytes, and lymphocytes are usually smaller.

Monocytes are the third most common type of leukocytes, making up about 2-10% of leukocytes in blood. Monocytes are the largest type of leukocytes, and can be 9-20 μm in diameter. They have a large eccentrically placed nucleus, which is kidney bean shaped, and have abundant cytoplasm.

Thrombocytes, or platelets, are not complete cells, but are small fragments of very large cells called megakaryocytes. Thrombocytes are the smallest formed elements of blood, having a diameter of 2-4 μm. Megakaryocytes develop from hemocytoblasts in the red bone marrow. Thrombocytes become sticky and clump together to form platelet plugs that close breaks and tears in blood vessels. They also initiate the formation of blood clots.

A summary of the reference ranges in cell counts per liter (L) and sizes in micrometers of formed elements of blood are provided in Table 1 (see URL: histology.leeds.ac.uk).

TABLE 1

| Name of Formed Element of Blood | Reference Range (Counts/Liter) | Normal Size (Diameter) |
|---|---|---|
| Erythrocytes (red blood cells) | $4\text{-}6 \times 10^{12}/L$ | 6-8 μm |
| Neutrophils (leukocytes or white blood cells) | 60-70% of $4.5\text{-}10 \times 10^9/L$ | 12-14 μm |
| Eosinophils (leukocytes or white blood cells) | 1-6% of $4.5\text{-}10 \times 10^9/L$ | 12-17 μm |
| Basophils (leukocytes or white blood cells) | 0.5-1% of $4.5\text{-}10 \times 10^9/L$ | 14-16 μm |
| Lymphocytes (leukocytes or white blood cells) | 20-50% of $4.5\text{-}10 \times 10^9/L$ | 6-14 μm |

TABLE 1-continued

| Name of Formed Element of Blood | Reference Range (Counts/Liter) | Normal Size (Diameter) |
|---|---|---|
| Monocytes (leukocytes or white blood cells) | 2-10% of 4.5-10 × $10^9$/L | 9-20 μm |
| Thrombocytes (platelets) | 150-450 × $10^9$/L | 2-4 μm |

In the clinical laboratory, a tissue substance from the body that is undergoing analysis is usually referred to as an analyte or a test. "Point-of-care Testing (POCT) is defined as medical diagnostic testing performed in close proximity to where the patient is receiving care. Point-of-care (POC) is not restricted to laboratory tests but are more common with respect to laboratory tests. POCT is usually performed by non-laboratory personnel and the results are used for clinical decision making. An example of a non-laboratory POC is POC ultrasound or POCUS.

For the sake of convenience and rapid turnaround time, the tissue or sample of choice for POCT is whole blood. Due to the complexity of blood, certain tests can only be performed on serum or plasma. Regardless whether the sample is serum, plasma or whole blood, the quantities of analytes measured are usually measured in the plasma component of whole blood and are usually reported as a mass or molar quantity per unit volume of the whole blood used for analysis. Because the actual volume of plasma present in the blood depends on the hematocrit, some systems attempt to correct the measured values to account for hematocrit.

Hemoglobin is an example of an analyte that is not present in the plasma unless hemolysis has occurred. Hemoglobin is usually present in red blood cells, and the mass or molar concentration of hemoglobin may be measured in unaltered blood, or in hemolyzed blood. Hemolyzed blood may be produced using sound waves or chemicals. Some analyzers measure hematocrit by electrical conductivity and convert the hematocrit measurement to a total hemoglobin concentration, and some analyzers measure total hemoglobin concentration by spectroscopy, and convert the total hemoglobin concentration to a hematocrit value. Spectroscopic calibration algorithms can be developed to measure both hematocrit and total hemoglobin concentration.

Another analyte that resides inside red blood cells is folic acid (~50% localized in red blood cells, the rest is stored mostly in the liver), and the measurement of RBC folate provides useful diagnostic information. Potassium is another analyte that resides in the RBCs, at much greater concentration compared with plasma concentration, however measurement of RBC potassium provides no diagnostic value, whereas plasma potassium is a commonly ordered analyte for aiding in assessing acid-base-electrolyte balance.

POCT involves a range of procedures of varying complexity that may include manual procedures and automated procedures conducted by portable analyzers. POCT is most efficient when the sample of interest can be applied to or loaded onto a test cartridge, the sample inlet of the cartridge capped, and the analytical (testing) steps performed automatically after the loaded and capped test cartridge is inserted into a slot or receptor of an analyzer. Some blood tests, for example coagulation assays and immunoassays require a fixed volume of sample to ensure that when mixed with a reagent, the ratio of the volume of sample to the volume (or mass) of the reagent is held constant. Sample volume must also be considered, for example when determining the lipid content in plasma. Other tests, for example electrolytes, may not require a fixed volume of sample. In the case of electrolytes, sample volume is usually not an issue if the electrolyte concentration is estimated by measuring electrical activity in the sample. Electrical activity is usually measured using electrochemical sensors, also referred to as biosensors. There are other tests that do not require a fixed volume of sample, and cannot be measured using biosensors, for example CO-oximetry and bilirubin. CO-oximetry is a spectroscopic or optical technique that is used to measure the amount of different Hemoglobin (Hb) species present in a blood sample, for example, Oxy-Hb, Deoxy-Hb, Met-Hb, Carboxy-Hb and Total-Hb. Met-Hb and Carboxy-Hb are non-functional hemoglobin, and their measurements are used to assess the oxygenation status of a patient. Billirubin is a degradation product of Hb and is elevated in liver disease and intravascular hemolysis. Billirubin accumulates in the plasma of neonates until the liver develops sufficiently to be able to eliminate the excess bilirubin from the plasma. Very high levels of bilirubin in neonates may cause brain damage.

Although electrolytes and CO-oximetry measurements do not usually require fixed volumes of blood, the distance the blood sample travels along microfluidic channels inside some cartridges may need to be controlled or metered. The term metered blood means that the blood is supplied in a measured or regulated amount. Applying an unmetered sample volume to test strips is well known; some test strips contain absorbing sections that can accommodate a known volume of plasma, after the RBCs are retained in another section of the test strip near the blood application site. In some cases, the hematocrit affects the plasma flow in test strips, and therefore correction for hematocrit may improve accuracy of the analyte measurement.

U.S. Pat. No. 8,206,650 to Samsoondar (the present inventor) teaches the combination of spectroscopy and biosensor technologies in one cartridge, and can therefore provide pH, blood gases and CO-oximetry using a handheld POCT analyzer. The users are provided with the convenience of applying the sample once, as opposed to using a first analyzer that employs biosensor technology alone, and a second analyzer that employs spectroscopy alone.

U.S. Pat. No. 9,470,673 and CA Pat. No. 2,978,737 to Samsoondar, teach cartridges for operation with a joint spectroscopic and biosensor blood analyzer. These publications teach a male-configured cartridge inlet, with the dual purposes of engaging a female-configured cap for sealing the inlet and engaging a capillary adaptor for drawing blood into the cartridge by capillary action. The combination of cap, capillary adaptor and inlet provides for dispensing blood from a syringe into the cartridge, as well as drawing capillary blood from a pin prick drop of blood on a patient's skin into the cartridge, for testing.

U.S. Pat. Nos. 9,821,307, 9,999,884, 10,272,430, and U.S. Pat. Appl'n Pub. No. US 2019/0224667 to Samsoondar teach cartridges having hinged caps for conducting coagulation tests, for example PT-INR (Prothrombin Time-International Normalized Ratio) and ACT (Activated Clotting Time), using a small drop of blood. In U.S. Pat. Appl'n Pub. No. US 2019/0224667, the use of regulated blood flow within a cartridge by applying either a positive or a negative pressure to the sample is described. This publication also discloses the use of liquid reagents located in either the cartridge or the analyzer used in conjunction with the cartridge, with the reagent disposed along a sample storage conduit that is used to transfer the sample from the inlet to the optical chamber so that the blood and a reagent are mixed prior to entering the optical chamber.

Many laboratory analysis of blood samples may be divided into the following three major sections: 1) Biochemistry; 2) Hematology; and 3) Coagulation. Other categories of laboratory tests may include microbiology and molecular biology. Hematology tests are usually measurement of properties of the formed elements of blood. CBC (Complete Blood Count) is one of the most common panel of tests performed in the Emergency Department (ED) of a hospital. A CBC is a hematology blood test used to evaluate a person's overall health and may detect a wide range of disorders, including anemia, infection and leukemia. A CBC measures several properties of a patient's blood, including: number of red blood cells, which carry oxygen; number of leukocytes or white blood cells, which fight infection; hemoglobin, the oxygen-carrying protein in red blood cells; hematocrit, the proportion of red blood cells to the fluid component, or plasma, in blood; and platelets, which help with blood clotting.

Most POCT were developed to include mostly Biochemistry testing (e.g., glucose, electrolytes, blood gases, drugs and cardiac markers). Further development in POCT included coagulation tests (e.g. PT-INR and ACT). Development of POCT for hematology, which includes measuring the quantities of the formed elements of blood (commonly referred to as cell counting) has made little progress, even though there is a great need for POCT for the formed elements of blood. Abnormal increases or decreases in cell counts as revealed in a CBC may indicate an underlying medical condition that calls for further evaluation. Even if a POCT analyzer cannot provide all the CBC measurements, a "partial" CBC is still useful.

Commercial analyzers are available that only measure leukocyte counts. U.S. Pat. No. 7,521,243 to Lindberg et al teaches a sample acquiring device for volumetric enumeration of white blood cells in a blood sample that includes a measurement cavity for receiving a blood sample.

U.S. Pat. Appin. Pub. 2011/0201045 by Levine et al teaches a method and analyzer for analyzing a hematologic sample centrifuged within a capillary tube.

A hemocytometer, along with a microscope, is used for manual cell counting. The hemocytometer comprises a glass slide with grid lines divided into 9 major squares, each measuring 1×1 mm. Except for the central major square, each of the other 8 major squares are subdivided into 16 of 0.25×0.25 mm squares (see FIGS. 1C and 1E). The central square consists of smaller spaced grid lines that can assist in determining the size of a cell (see FIG. 1F). The coverglass for hemocytometers are specifically designed with regards to thickness and size. When the coverglass is placed over the counting area, this leaves a specific area for introducing the cells (suspended in liquid) to be counted. The gap between the top surface of the counting area and the bottom surface of the coverglass is 0.1 mm. Therefore, the volume of each 1×1 mm corner square is 100 nanoliters (nL). After the cell suspension is loaded in the hemocytometer, the number of cells in the corner squares may be counted using a microscope, and averaged. For illustration, a version of a hemocytometer (regarded as prior art), is provided in FIGS. 1A-1F. Some developing countries rely on manual blood cell counting, which is time consuming and errorprone.

U.S. Pat. No. 2,656,508 to Coulter, introduced the "Coulter Principle" that is still in use today for automated cell counting. The "Coulter Principle" refers to the use of an electric field for counting and sizing dilute suspensions of particles in conducting liquids. The "Coulter Principle" is currently applied in several modified procedures to provide more detailed blood cell counting, including red blood cell count, the different types of white cell counts, platelet count, and the mean size of the various cell types. Although the blood cell counting using the "Coulter Principle" is still very popular in clinical labs, the size of the analyzers limits the use of the "Coulter Principle" for POCT.

POCT has improved patient care in several areas including the Emergency Department (ED) of hospitals, but the ED is usually very busy and may have space for implementing one POCT analyzer, and practical issues (physical constraints) may limit implementation of more than one POCT analyzer. In addition to having accurate and reliable POCT in the ED, user friendliness and consolidation of tests is required. Therefore, there is a need to provide POCT analyzers that consolidate certain Hematology tests and certain Biochemistry tests. The present invention is intended to meet this need of consolidation of Hematology and Biochemistry tests in a single POCT system. Furthermore, the present invention may also decrease the volume of blood sample required for POCT.

SUMMARY OF THE INVENTION

The invention relates to a joint Hematology and Biochemistry point-of-care testing (POCT) system and also provides an improved Hematology POCT system.

An analyzer for measuring one or more analyte quantities per unit volume of blood and one or more formed element quantities per unit volume of blood, in a blood sample when the blood sample is present within the analyzer is described herein. The analyzer comprises:

a receptor for receiving a cartridge, the cartridge comprising an optical chamber for receiving the blood sample;

at least one source of interrogating electromagnetic radiation (EMR) for interrogating at least some of the blood sample when the blood sample is positioned within the optical chamber, and producing a first set of emerging EMR and a second set of emerging EMR;

a means for directing the first set of emerging EMR to a one-dimensional multi-channel detector and the second set of emerging EMR to a two-dimensional multi-channel detector;

a dispersing element for receiving and dispersing the first set of emerging EMR into its component wavelengths, to produce dispersed EMR;

the one-dimensional multi-channel detector for receiving the dispersed EMR and generating wavelength-specific electrical signals;

an analog to digital converter for receiving the wavelength-specific electrical signals and generating wavelength-specific digital information;

the two-dimensional multi-channel detector for receiving the second set of emerging EMR and generating detector-specific electrical signals;

one of the analog to digital converter and a second analog to digital converter for receiving the detector-specific electrical signals and generating detector-specific digital information;

one or more processors for:
controlling the analyzer;
transforming the wavelength-specific digital information into the one or more analyte quantities per unit volume of blood; and
transforming the detector-specific digital information into the one or more formed element quantities per unit volume of blood.

The at least one source of interrogating EMR within the analyzer described above may be one of a polychromatic EMR, a combination of a plurality of monochromatic EMR, and a combination of one or more polychromatic and one or more monochromatic EMR. Furthermore, the polychromatic source of EMR may be one of an incandescent lamp, a white LED, a ring of LEDs, a bundle of LEDs, a plurality of lasers, and a combination thereof. For example, the polychromatic source of EMR may encompass wavelengths within a range of about 300-2,500 nanometers. For example, the polychromatic source of EMR may encompasses wavelengths within a range of about 400-800 nanometers.

Furthermore, in the analyzer as described above, the means for directing the first set of emerging EMR to the one-dimensional multi-channel detector and the second set of emerging EMR to the two-dimensional multi-channel detector comprises one of a beam splitter or a pivotal mirror, wherein:
  the first set of emerging EMR is transmitted through the optical chamber, and the second set of emerging EMR is reflected from the optical chamber;
  the first set of emerging EMR is reflected from the optical chamber and the second set of emerging EMR is transmitted through the optical chamber; or
  the first set of emerging EMR is reflected from the optical chamber and the second set of emerging EMR is reflected from the optical chamber;
  and wherein a first general direction of the first set of emerging EMR and a second general direction of the second set of emerging EMR define an angle less than 90 degrees.

The beam splitter may be selected from one of a bifurcated optical fiber, a plate comprising a partially silvered coating, a plate comprising a dielectric coating, and a partially reflecting prism.

Also provided herein is an analyzer as described above, wherein the analyzer further comprises a magnification system disposed between the receptor and the two-dimensional multi-channel detector. The magnification system may provide a plurality of magnification settings for optimizing the image formed on the two-dimensional multi-channel detector.

The one-dimensional multi-channel detector of the analyzer as described above may be selected from a photodiode linear array and a charge-coupled device (CCD) linear array. The two-dimensional multi-channel detector may be selected from a CCD camera and a complementary metal oxide semiconductor (CMOS) camera. The CCD camera or the CMOS camera may comprise pixels having a pixel pitch of about 1-10 μm. For example, the pixel pitch may be less than 4 μm. The analyzer may further comprise a collimation system is disposed between the source of interrogating EMR and the two-dimensional multi-channel detector. Additionally, the analyzer may comprise a focusing system disposed between the source of interrogating EMR and the two-dimensional multi-channel detector.

The analyzer as described above may also comprise an analyzer pump for operating in conjunction with the cartridge, the analyzer pump having a positive pressure mode for generating positive pressure and a negative pressure mode for generating negative pressure, and a hollow needle comprising a first end operatively connected to the analyzer pump, a second end distal to the first end and operatively connected to the first end, the hollow needle further comprising an outer surface, the outer surface for engaging with a sealing member installed in cartridge exit duct of the cartridge.

Also described herein is a system comprising the analyzer as described above and a cartridge with an optical chamber placed within the receptor.

The cartridge of the system as described above may also comprise a biosensor chamber having one or more biosensors for generating additional one or more analyte quantities per unit volume of blood.

The optical chamber of the cartridge of the system as described above, comprises an upper and a lower optical window, and one or both of the upper and lower optical window may be a transparent, or a translucent optical window. One of the upper and the lower optical window may comprise a reflecting surface for reflecting EMR after the interrogating EMR has penetrated the optical chamber. Furthermore, the upper and the lower optical window are substantially parallel to each other, and the upper and the lower optical windows are spaced apart about 50-200 micrometers. Additionally, an area of the transparent or the translucent optical window may be about 1-100 square millimeters.

The cartridge of the system may also comprise an upper surface and a lower surface, the upper surface defining a sample storage well comprising a top opening, a hingedly attached cap, one of and a cartridge vent and a cap vent, one of an air bladder, a cartridge exit and a cartridge air inlet, the sample storage well in fluid communication with the one of a cartridge vent and cap vent, and the one of an air bladder, cartridge exit and a cartridge air inlet, and wherein at least one reagent is disposed between the top opening and one of the cartridge vent, the cartridge exit, and the cartridge air inlet. The at least one reagent may be one of a hemolyzing reagent and a staining reagent. The cartridge of the system as described above may also comprise a sealed blister containing one of a liquid reagent and a diluent, and the analyzer of the system may further comprise:
  a means for releasing the liquid reagent or the diluent from the sealed blister into the cartridge; and
  a means for mixing the liquid reagent or the diluent with the blood sample, when the blood sample is present within the cartridge.

Also provided herein is a cartridge (A) for measuring one or more analyte quantity per unit volume of blood and at least one first formed element quantity per unit volume of blood, of a blood sample when the blood sample is present within the cartridge, the cartridge comprising:
  a cartridge body having an upper surface and a lower surface;
  the upper surface defining a sample storage well, the sample storage well comprising a top portion for receiving a blood sample and a bottom portion for releasing at least a portion of the blood sample into an optical chamber;
  the optical chamber comprising an upper and a lower optical window;
  a pre-optical chamber conduit for transferring a portion of the blood sample from the sample storage well to the optical chamber;
  a post-optical chamber conduit between the optical chamber and one of a vent and a cartridge exit, the post-optical chamber conduit for receiving excess blood flowing out of the optical chamber;
  one or more reagents disposed in the post-optical chamber conduit, sufficiently far enough from the optical chamber and the vent or the cartridge exit, so that when the blood sample is positioned in the optical chamber a first sample interrogation may be performed on unaltered blood, and when the blood sample is mixed with at least some of the one or more reagents to produce an altered blood, a second sample interrogation may be performed on the altered blood;

a cap having a top side and an underside, the cap attached to the cartridge body and movable from a first to a second position;

the cartridge body further comprising one of:

A) a positive to negative pressure means, so that when the blood sample is present in the cartridge body and when a positive pressure is applied, at least a portion the blood sample flows in a direction towards the vent, and when a negative pressure is applied at least a portion of the blood sample flows in a direction away from the vent, the positive to negative pressure means comprising:

one of i) an air bladder in the cartridge body for generating the positive and the negative pressure by respectively squeezing and releasing the air bladder; and ii) a cartridge air inlet duct positioned in the cartridge body and operatively connected to a closed air passage facilitated by a groove set into the upper surface of the cartridge body, a recess set into the underside of the cap, or a combination thereof, the cartridge air inlet duct comprising a sealing member so that when the cartridge is inserted within an analyzer, the sealing member frictionally engages an outer surface of a hollow needle operatively connected with an analyzer pump, and the positive pressure and the negative pressure generated by the analyzer pump are transferable to the cartridge air inlet duct;

one of:

an air bladder communication port defined by the upper surface of the cartridge body, wherein the air bladder communication port is operatively connected with the air bladder; and an analyzer pump communication port defined by the upper surface of the cartridge body, so that when the cartridge is inserted within the analyzer, the analyzer pump communication port operatively connects with the analyzer pump;

a flat surface located on the upper surface of the cartridge body, the flat surface of the cartridge body surrounding the top portion of the sample storage well and one of the air bladder communication port and the analyzer pump communication port; and a cap flat surface located on the underside of the cap;

wherein the cartridge is adjustable between an unsealed configuration and a sealed configuration; in the unsealed configuration the cap is in the first position and the sample storage well is configured to receive the blood sample; and in the sealed configuration the cap is in the second position and a portion of the flat surface of the cartridge body mates with the cap flat surface to form the closed air passage operatively connecting one of the air bladder communication port and the analyzer pump communication port to the sample storage well so that either the positive pressure or the negative pressure is transferable to the sample storage well; and B) a negative to positive pressure means so that when the blood sample is present in the cartridge body and when the negative pressure is applied, at least a portion the blood sample flows in a direction towards a cartridge exit duct, and when the positive pressure is applied at least a portion of the blood sample flows in a direction away from the cartridge exit duct, the negative to positive pressure means comprising:

the cartridge exit duct positioned in the cartridge body and operatively connected to the optical chamber via the post-optical chamber conduit, the cartridge exit duct comprising a sealing member so that when the cartridge is inserted within the analyzer, the sealing member frictionally engages an outer surface of a hollow needle of the analyzer so that the negative pressure and the positive pressure generated by the analyzer pump are transferable to the cartridge exit duct; wherein the cartridge is adjustable between an open configuration and a closed configuration; in the open configuration the cap is in the first position and the sample storage well is configured to receive the blood sample; and in the closed configuration the cap is in the second position and the sample storage well is covered with the cap, the cap further comprising a cap vent so that when the blood sample is positioned within the sample storage well, the blood sample is subjected to atmospheric pressure, so that the negative pressure and the positive pressure are transferable to a leading edge of the blood sample.

The top portion of the sample storage well of the cartridge (A) as just described may comprise a boss for increasing a storage capacity of the sample storage well. The sample storage well may also be a sample storage well insert, and the sample storage well insert may be inserted in the cartridge body, furthermore the sample storage well insert is more wettable than the cartridge body.

Additionally the cap of cartridge (A) may be one of a hinged cap and a screw-type cap.

The cartridge (A) as described above may further comprise a conductivity sensor, the conductivity sensor comprising a pair of conductivity electrodes disposed between the optical chamber and one of the vent and the cartridge exit duct, so that when the blood sample is positioned within the cartridge body and the cartridge is positioned within the analyzer, the conductivity sensor detects a location of the leading edge of the blood and communicates with the analyzer to control one of the air bladder and the analyzer pump.

The cartridge (A) as described above may also comprise one of an enlarged cavity disposed near a junction of the bottom portion of the sample storage well and the pre-optical chamber, and a hydrophobic insert disposed near the junction, the sample storage well further comprising internal walls, the internal walls of the sample storage well characterized as being more wettable than a surface of the pre-optical chamber.

Furthermore, the cartridge (A) as described above, may comprise a biosensor chamber, the biosensor chamber disposed between, and in operative communication with the optical chamber and the one of a vent and a cartridge exit duct, and wherein the biosensor chamber comprises one or more biosensors for generating one or more signals used to calculate one or more properties of the blood sample.

An alternate cartridge (B) for measuring one or more of at least one analyte quantity per unit volume of blood and at least one formed element quantity per unit volume of blood, when the blood sample is present within the cartridge, is described herein. The cartridge comprises:

a cartridge body having an upper surface and a lower surface;

a sample inlet portion located on the upper surface, the sample inlet portion comprising:
  a sample storage well defined by the upper surface, the sample storage well comprising a top portion for receiving a blood sample and a bottom portion for releasing at least a portion of the blood sample into a pre-optical chamber conduit;
  an analyzer pump communication port defined by the upper surface, the analyzer pump communication port in operative communication with an analyzer pump when the cartridge is installed within an analyzer;
  a flat surface located on the upper surface of the cartridge body, the flat surface surrounding the top portion of the sample storage well and the analyzer pump communication port;
an optical chamber comprising an upper and a lower optical window;
the pre-optical chamber conduit for transferring at least a portion of the blood from the sample storage well to the optical chamber;
a post-optical chamber conduit for receiving excess blood flowing out of the optical chamber, post-optical chamber conduit in operative communication with the optical chamber and a vent, the vent for modulating blood flow in the cartridge;
a cartridge air inlet duct operatively connected to a closed air passage facilitated by a groove set into the upper surface of the cartridge body, a recess set into the underside of a cap, or a combination thereof, the cartridge air inlet duct comprising a sealing member for frictionally engaging an outer surface of an analyzer pump hollow needle so that when the cartridge is installed within the analyzer, pressure from the analyzer pump is transferable to the analyzer pump communication port via the cartridge air inlet duct;
a cap having a top side and an underside, the cap attached to the cartridge body and movable from a first to a second position;
a cap flat surface located on the underside: wherein the cartridge is adjustable between an unsealed configuration and a sealed configuration; in the unsealed configuration the cap is in the first position and the sample storage well is configured to receive the blood sample; and in the sealed configuration the cap is in the second position, and a portion of the flat surface of the cartridge body mates with the cap flat surface to form the closed air passage and operatively connecting the analyzer pump communication port to the sample storage well so that when installed within the analyzer, pressure is transferable from the analyzer pump to the sample storage well.

The top portion of the sample storage well of the alternate cartridge (B) as described above may comprise a boss for increasing the sample storage well storage capacity. Furthermore, the cap may be one of a hinged cap and a screw-type cap.

The alternate cartridge (B) as described above may further comprise a conductivity sensor, the conductivity sensor comprising a pair of conductivity electrodes disposed between the optical chamber and one of the vent and the cartridge exit duct, so that when the blood sample is positioned within the cartridge body and the cartridge is positioned within the analyzer, the conductivity sensor detects a location of a leading edge of the blood and communicates with the analyzer to control the analyzer pump.

The alternate cartridge (B) as described above may also comprise one of an enlarged cavity disposed near a junction of the bottom portion of the sample storage well and the pre-optical chamber, and a hydrophobic insert disposed near the junction, the sample storage well further comprising internal walls, the internal walls of the sample storage well characterized as being more wettable than a surface of the pre-optical chamber.

Also provided herein is a cartridge (C) for measuring one or more properties of a blood sample when the blood sample is present within the cartridge. The cartridge comprising:
  a cartridge body having a upper surface and a lower surface;
  a sample storage well defined by the upper surface, the sample storage well comprising a top portion for receiving the blood sample and a bottom portion for receiving a metered volume of a diluent and for releasing a diluted blood;
  a cartridge flat surface located on the upper surface surrounding the top portion of the sample storage well;
  a sealed blister for containing the diluent, and means for releasing the diluent into a diluent holding conduit, the sealed blister located in the cartridge body;
  a hinged hollow cap attached to the cartridge body, the hinged hollow cap movable from a first to a second position, the hinged hollow cap comprising
  a top side, the top side defining a cap vent;
  an underside, the underside defining an inlet, the inlet surrounded by a cap flat surface;
  a leading edge, so that when the cap flat surface is frictionally engaged with the cartridge flat surface and moved from the first to the second position, and when blood is present in the sample storage well, the leading edge skims off excess blood projecting out of the top portion of the sample storage well;
  a means for metering a volume of blood;
  a means for metering the volume of the diluent;
  a means for mixing the volume of the blood and the volume of the diluent; and
  an optical chamber in fluid communication with the bottom portion, the optical chamber for receiving the diluted blood for sample interrogation.

Many laboratory analyses of blood samples may be divided into the following categories: 1) Biochemistry; 2) Coagulation; and 3) Hematology. Most POCT were developed to include mostly Biochemistry testing, which may include the following: glucose, for assessing carbohydrate metabolism; electrolytes and blood gases, for assessing respiratory and metabolic function; enzymes, e.g., ALT, for assessing liver function; metabolites, e.g., creatinine, used for assessing kidney function, and lactate, for detecting sepsis; drugs, for detecting drugs of abuse; and cardiac markers, e.g., BNP and Troponin, for assessing cardiac function. Further POCT development included coagulation tests, e.g. PT-INR and ACT, for monitoring anti-coagulation therapy like warfarin and heparin respectively. Development of POCT for hematology, which includes measuring the quantities of the formed elements of blood, commonly referred to as cell counting has made little progress even though there is a need for POCT for the formed elements of blood.

The system provided herein, comprising an analyzer and a cartridge, provides a compact and versatile POCT system that is effective for use within a variety of health care settings, for example, within space-limited Emergency Department (ED) of hospitals and in the vehicles used by first responders. The system described herein may also be used to determine multiple properties, for example, one or more than one analyte quantity per unit volume of blood and at least one formed element quantity per unit volume of blood, within a single blood sample for example, a capillary blood sample (i.e., a pin-prick blood sample), thereby reducing the need to obtain additional blood samples. By consolidating several different tests in a single, user-friendly POCT analyzer, the system may be operated by non-laboratory personnel.

Other aspects and features of the present invention will become apparent, to those having ordinary skill in the art, upon review of the following description of specific embodiments of the invention, which are provided as examples.

BRIEF DESCRIPTION OF THE DRAWINGS

A better understanding of the novel features and advantages of the present invention will be made by reading the detailed description of the preferred embodiments provided later, in conjunction with the accompanying drawings, in which:

FIG. 1A (Prior Art) a top view illustrating a version of a hemocytometer (a cell counting chamber device) that is used in conjunction with a microscope for manual cell counting;

FIG. 1B (Prior Art) is a cross-sectional view through the hemocytometer shown in FIG. 1A, along line B-B;

FIG. 1C (Prior Art) is an enlarged view of detail C shown in FIG. 1A;

FIG. 1D (Prior Art) is an enlarged view of detail D shown in FIG. 1B.

FIG. 1E (Prior Art) is an enlarged view of the top right square of FIG. 1C as indicated in FIG. 1C;

FIG. 1F (Prior Art) is an enlarged view of center square of FIG. 1C as indicated in FIG. 1C;

FIG. 10F is a perspective view of the cartridge 10A shown in FIG. 10A, in a fully open position;

FIG. 10G is a perspective view of the cartridge 10A shown in FIG. 10A, but in a fully closed position;

FIG. 10H is top view of the cartridge 10A shown in FIG. 10G, in the fully closed position;

FIG. 10J is an enlarged cross-sectional view through the cartridge 10A shown in FIG. 10H along line J-J;

FIG. 10K is an enlarged cross-sectional view through the cartridge 10A shown in FIG. 10H along line K-K;

FIG. 11A is an exploded top perspective view of a cartridge 10B for measuring at least one property of blood, according to a second embodiment of the cartridge;

FIG. 11B is a bottom view of the first housing member 50B of the cartridge shown in FIG. 11A;

FIG. 11C is a perspective top view of the cap 70B shown in FIG. 11A;

FIG. 11D is a perspective bottom view of the cap 70B shown in FIG. 11A;

FIG. 11E is a perspective top view of the cartridge 10B shown in FIG. 11A, in a fully open position;

FIG. 11F is a perspective top view of the cartridge 10B shown in FIG. 11A, in a fully closed position;

FIG. 11G is top view of the cartridge 10B shown in FIG. 11E;

FIG. 11H is top view of the cartridge 10B shown in FIG. 11F;

FIG. 11J is an enlarged cross-sectional view through the cartridge 10B shown in FIG. 11G along line J-J;

FIG. 11K is an enlarged cross-sectional view through the cartridge 10B shown in FIG. 11H along line K-K;

FIG. 12A is an exploded top perspective view of a cartridge 10C for measuring at least one property of blood, according to a third embodiment of the cartridge;

FIG. 12B is a bottom view of the first housing member 50C of the cartridge shown in FIG. 12A;

FIG. 12C is a top view of the second housing member 60C of the cartridge shown in FIG. 12A;

FIG. 12D is a perspective top view of the cartridge 10C shown in FIG. 12A, in a fully open position;

FIG. 12E is a perspective top view of the cartridge 10C shown in FIG. 12A, but in a fully closed position;

FIG. 12F is top view of the cartridge 10C shown in FIG. 12E;

FIG. 12G is an enlarged cross-sectional view through the cartridge 10C shown in FIG. 12F along line G-G;

FIG. 12H is an enlarged cross-sectional view through the cartridge 10C shown in FIG. 12F along line H-H;

FIG. 12J is an enlarged cross-sectional view through the cartridge 10C shown in FIG. 12F along line J-J;

FIG. 13D is top view of the cartridge 10D shown in FIG. 13A, but in a closed position;

FIG. 13E is an enlarged cross-sectional view through the cartridge 10D shown in FIG. 13D along line E-E;

FIG. 13F is an enlarged cross-sectional view through the cartridge 10D shown in FIG. 13D along line F-F.

FIG. 14H is a top view of the cartridge 10E shown in FIG. 14A with the cap in an open position, showing details;

FIG. 14J is an enlarged cross-sectional view through the cartridge 10E shown in FIG. 14H along line J-J;

FIG. 14K is an enlarged cross-sectional view through the cartridge 10E shown in FIG. 14H along line K-K;

FIG. 14L is a detailed view of detail L of the second directional valve shown in FIG. 14J;

FIG. 14M is a perspective top view of the cartridge 10E shown in FIG. 14H.

FIG. 14N is a top view of the cartridge 10E shown in FIG. 14A with the cap in a closed position, showing details;

FIG. 14P is an enlarged cross-sectional view through the cartridge 10E shown in FIG. 14N along line P-P;

FIG. 14Q is an enlarged cross-sectional view through the cartridge 10E shown in FIG. 14N along line Q-Q;

FIG. 14R is a perspective top view of the cartridge 10E shown in FIG. 10N

FIG. 14S is a perspective top view of the cap 70E of cartridge 10E;

FIG. 14T is a perspective bottom view of the cap 70E of cartridge 10E;

FIG. 14U is a perspective view of a first directional valve element 313E (The top and the bottom are the same);

FIG. 14V is a top view of a second directional valve element 321E;

FIG. 14W is a cross-sectional view of the second directional valve element 321E shown in FIG. 14V along line W-W;

FIG. 14X is a first perspective view of a second directional valve element 321E; and FIG. 14Y is a second perspective view of a second directional valve element 321E.

For a better understanding of the present invention, and to show more clearly how it may be carried into effect, reference will now be made, by way of example, to the accompanying drawings, and which are described in the following detailed description of preferred aspects of the invention.

DETAILED DESCRIPTION OF PREFERRED ASPECTS OF THE INVENTION

An analyzer and a system for measuring one or more analyte quantities per unit volume of blood (i.e., the concentration of the analyte) using spectroscopic technique, and one or more formed element quantities per unit volume of blood (i.e., a cell count) using imaging technique, are described. Also described are one or more cartridges for receiving a sample of blood for use within the analyzer.

Figure 8:
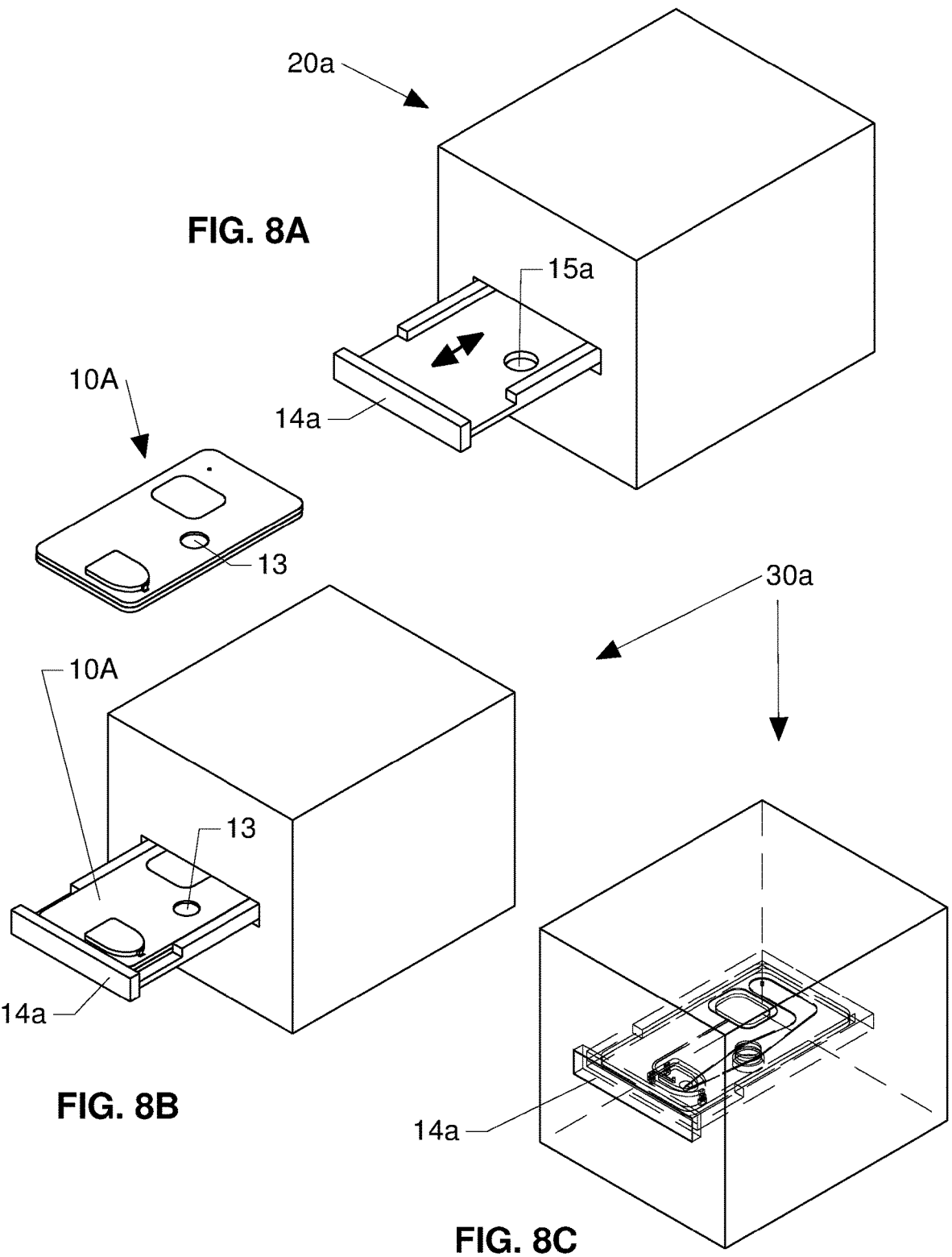
FIG. 8A is perspective view of an example of a first embodiment of a system 30a for measuring one or more analyte quantities per unit volume of blood and one or more formed element quantities per unit volume of blood, in a blood sample, showing a cartridge 10A separate from an analyzer 20a showing a receptor 14a in an open position.
FIG. 8B is perspective view of an example of a first embodiment of a system 30a for measuring one or more analyte quantities per unit volume of blood and one or more formed element quantities per unit volume of blood, in a blood sample, showing the cartridge 10A engaged with the receptor 14a, with the receptor in an open position.
FIG. 8C is perspective view of an example of a first embodiment of a system 30a for measuring one or more analyte quantities per unit volume of blood and one or more formed element quantities per unit volume of blood, in a blood sample, showing the cartridge 10A engaged with the receptor 14a, with the receptor in a closed position.

By way of example, the system 30a comprises a cartridge 10A and an analyzer 20a (see FIGS. 8A-8C). The cartridge 10A comprises at least one optical chamber 13 for interrogating or illuminating at least some of a blood sample with electromagnetic radiation (EMR) via an aperture 15a shown in FIG. 8A. The EMR transmitted through the blood in the optical chamber and/or reflected from the blood in the optical chamber is used to measure the analyte concentration by spectroscopy and the cell count by imaging.

The system of the present invention described comprises at least one cartridge having at least one optical chamber (see 13 in cartridge 10A, used as an example, shown in FIG. 8A), and an analyzer (see 20a shown in FIG. 8A).

As described herein the analyzer typically comprises:
a) at least one receptor (see 14a shown in FIGS. 8A-8C) for receiving the cartridge. A person having skill in the art should appreciate that the receptor may come in different forms, for example, a pull-out tray as illustrated in FIGS. 8A-8C, a hinged tray that swivels in and out of the body of the analyzer, a simple slot for inserting the cartridge, or a stationary tray that can be accessed by opening a door in the body of the analyzer. Any type of cartridge with an optical chamber may be used, or adapted for use (i.e. to ensure alignment of the optical chamber with the path of EMR that is used to interrogate a sample), with the analyzer. Non limiting examples of cartridges that may be used include those shown in FIGS. 10-13 as described herein; and those as described in U.S. Pat. Nos. 8,206,650, 9,470,673, 9,821,307, 9,999,884, 10,272,430, and U.S. Pat. Appl'n Pub. No. US 2019/0224667, and CA Pat. No. 2,978,737 (each of which are incorporated herein by reference).

b) at least one source of EMR (the source of EMR may also be termed interrogating EMR, and these terms are used interchangeably) for interrogating or illuminating at least some of the blood sample in the optical chamber (see optical chamber 13 in FIG. 8A, as an example), and producing a first set of emerging EMR and a second set of emerging EMR. One or more, of the at least one source of interrogating EMR should be a polychromatic source of EMR. A person having skill in the art would realize that polychromatic EMR could be the combination of a plurality of monochromatic EMR. The polychromatic source of EMR may encompasses wavelengths within a range of about 300-2,500 nanometers, for example, within a range of about 400-800 nanometers. Some embodiments of the analyzer may also comprise a collimation or collimating system (e.g., see 46a in FIG. 2) for providing substantially parallel illuminating or emerging rays of EMR, and some embodiments may comprise a focusing system (e.g., see 48F in FIG. 7) having one or more focusing lenses for projecting a real image of the blood sample on to a two-dimensional multi-channel detector. In some embodiments the collimation system may be disposed between the source of EMR and receptor of the analyzer, and in other embodiments the collimation system may be disposed between the receptor of the analyzer and the two-dimensional multi-channel detector. Embodiments of a system having an area of the blood sample being interrogated by the EMR significantly smaller than the area of the two-dimensional multi-channel detector may comprise a magnification system in order to magnify the image to occupy a substantial area of the two-dimensional multi-channel detector, for increasing the resolution of the formed elements of blood. Optional magnification systems are shown as 18b in FIG. 3, 18c in FIG. 4, 18d in FIG. 5, 18e in FIG. 6, and 18g in FIG. 9. Electronic magnification of the image after the image is formed on two-dimensional multi-channel detector is another option for increasing the space between formed elements of blood that are imaged. In some embodiments, the area of the optical chamber may be similar to the area of the two-dimensional multi-channel detector, and no magnification may be required, depending on the size of the formed elements being observed. The depth of field provided by a magnification system is preferably approximately equal to the depth of the optical cavity, in order to keep formed elements at different levels in the optical chamber in focus. Some embodiments may comprise a magnification system that provides a plurality of magnification settings for optimizing the image formed on the two-dimensional multi-channel detector;

c) a means for directing each of the first set of emerging EMR and the second set of emerging EMR to one of a one-dimensional multi-channel detector and a two-dimensional multi-channel detector. The one-dimensional multi-channel detector may be a photodiode linear array or a charge-coupled device (CCD) linear array. The two-dimensional multi-channel detector may be a CCD camera or a complementary metal oxide semiconductor (CMOS) camera. The pixel pitch of the CCD camera and the CMOS camera is preferably between one quarter and one half the size of the formed elements being observed, in order to resolve the formed elements (see Table 1 for the sizes of formed elements of blood). Due to the rapid development in detection and imaging technologies, the examples provided should not be limiting to the present invention in any way;

d) a dispersing element for receiving and dispersing the first set of emerging EMR into its component wavelengths, to produce dispersed EMR; e) the one-dimensional multi-channel detector for receiving the dispersed EMR and generating wavelength-specific electrical signals; f) an analog to digital converter for receiving the wavelength-specific electrical signals and generating wavelength-specific digital information; g) the two-dimensional multi-channel detector for receiving the second set of emerging EMR and generating detector-specific electrical signals; h) the analog to digital converter or a second analog to digital converter for receiving the detector-specific electrical signals and generating detector-specific digital information; and i) one or more processors integrated in the analyzer or separate processor modules electrically connected to the analyzer. The one or more processors may be used to: 1) control the analyzer; 2) transform the wavelength-specific digital information into the one or more analyte quantities per unit volume of blood; and 3) transform the detector-specific digital information into the one or more formed element quantities per unit volume of blood. Examples of output displays from processors are provided as 37a and 39a in FIG. 2. It should be understood by a person skilled in the art, that the digital information used to create displays 37a and 39a may be used in several different ways. For example, instead of an absorbance spectrum 39a, a transmission or reflection spectrum may be displayed. Instead of the outline of formed elements of blood, the formed elements may appear as black spots against a white background, if staining is employed. Moreover, it is the actual digital data (or information) that are used, for example, digital absorbance data, digital transmission data or digital reflection data that are used in conjunction with pre-developed calibration algorithms to predict one or more analyte concentration or one or more cell count.

The source of EMR (interrogating EMR) in the system described may be a single source or multiple sources of EMR, and at least one or a combination of sources must produce polychromatic EMR for spectral or spectroscopic analysis of the blood. A second source of EMR may be polychromatic, a laser (monochromatic), a light emitting diode (LED). The polychromatic source of EMR may be one of an incandescent lamp, a white LED, a ring of LEDs, and a bundle of LEDs. The source(s) of EMR may be arranged to operate in reflection mode, transmission mode, or a combination thereof. Additionally, a dispersing element is required for receiving and dispersing a set of emerging EMR into its component wavelengths, to produce dispersed EMR. The dispersing element may be a grating (diffraction grating) or a dispersion prism (see 28a in FIG. 2), and the grating may be a reflecting grating (see 28c in FIGS. 4 and 28d in FIG. 5) or a transmission grating (see 28b in FIGS. 3 and 28e in FIG. 6). As described below, the cartridges of the present invention may contain staining reagents that may selectively stain the nucleus of leukocytes. Therefore, a person having skill in the art should realize that by choosing a source of EMR of a wavelength or wavelengths that is/are absorbed by a particular stain(s) (or dye) taken up by the nucleus of leukocytes, and using transmission mode, the stained leukocytes will transmit less EMR than the surrounding plasma. In other words, leukocytes that are stained by the particular dye may appear as black dots when the incident wavelength corresponds to the wavelength of absorbance maximum of the dye. In transmission mode, even without the use of staining reagents, formed elements are expected to attenuate more EMR (mono- or polychromatic EMR) than the surrounding plasma, producing images having various shades of grey. The attenuation of EMR may be the result of absorbance, scattering, or a combination thereof. In reflectance mode, and using a black surface on the side opposite to the side of the source of EMR, even without the use of staining reagents, formed elements are expected to reflect more EMR (mono- or polychromatic EMR) than the surrounding plasma, producing lighter images on a darker background; the EMR passing through the plasma is expected to be absorbed by the black surface. These are just examples of how images of formed elements of blood may be created. The systems used for measuring one or more formed element quantities per unit volume of blood, as describe previously, may not all be suitable for measuring one or more analyte quantities per unit volume of blood, therefore both measurements are to be considered when designing a system according to the present invention.

Figure 5:
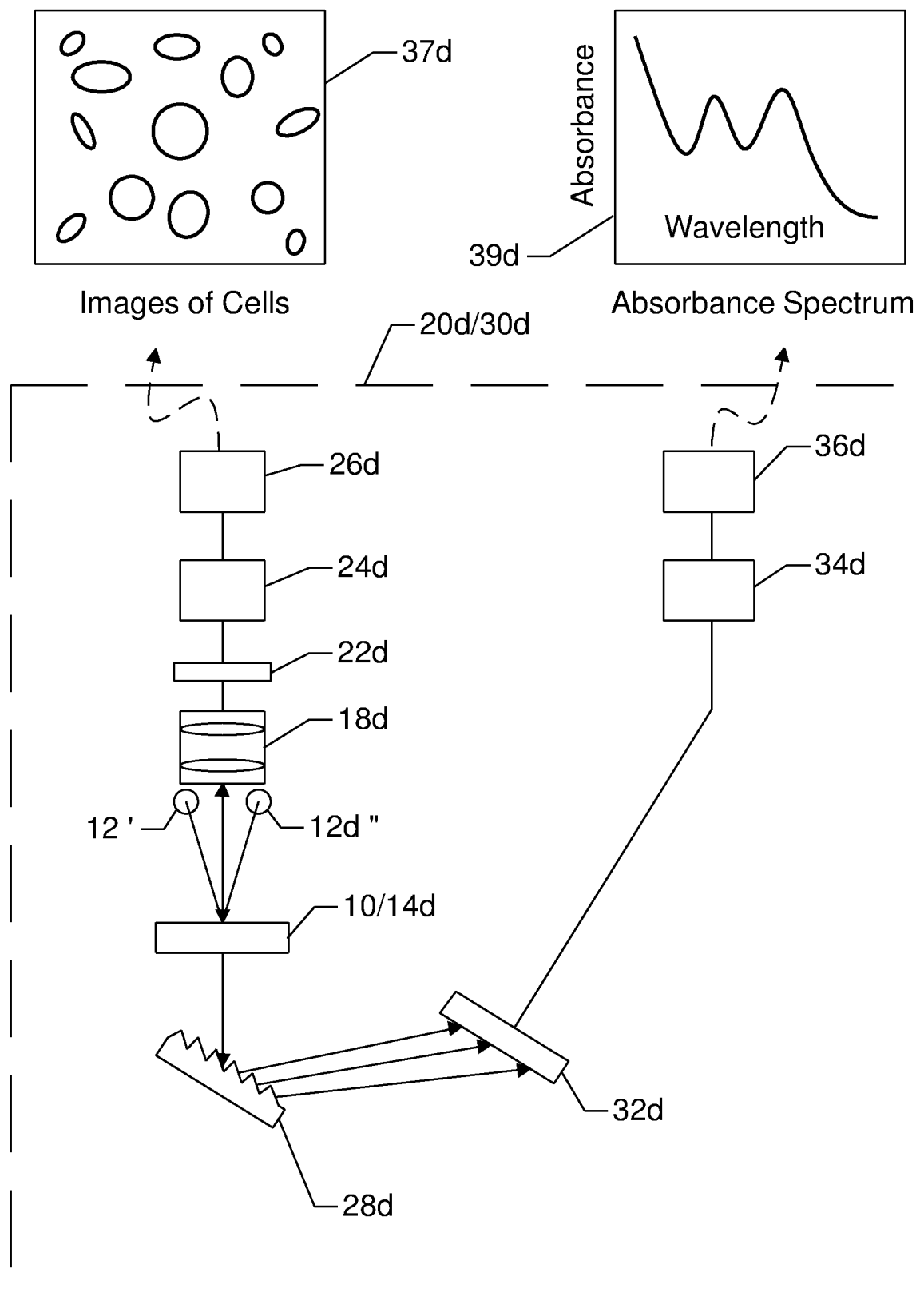
FIG. 5 is a block diagram of an example of a fourth embodiment of a system 30d (lower panel) for measuring one or more analyte quantities per unit volume of blood and one or more formed element quantities per unit volume of blood, in a blood sample. Output displays of the system (upper left and right panels) are provided as non-limiting examples.
Figure 6:
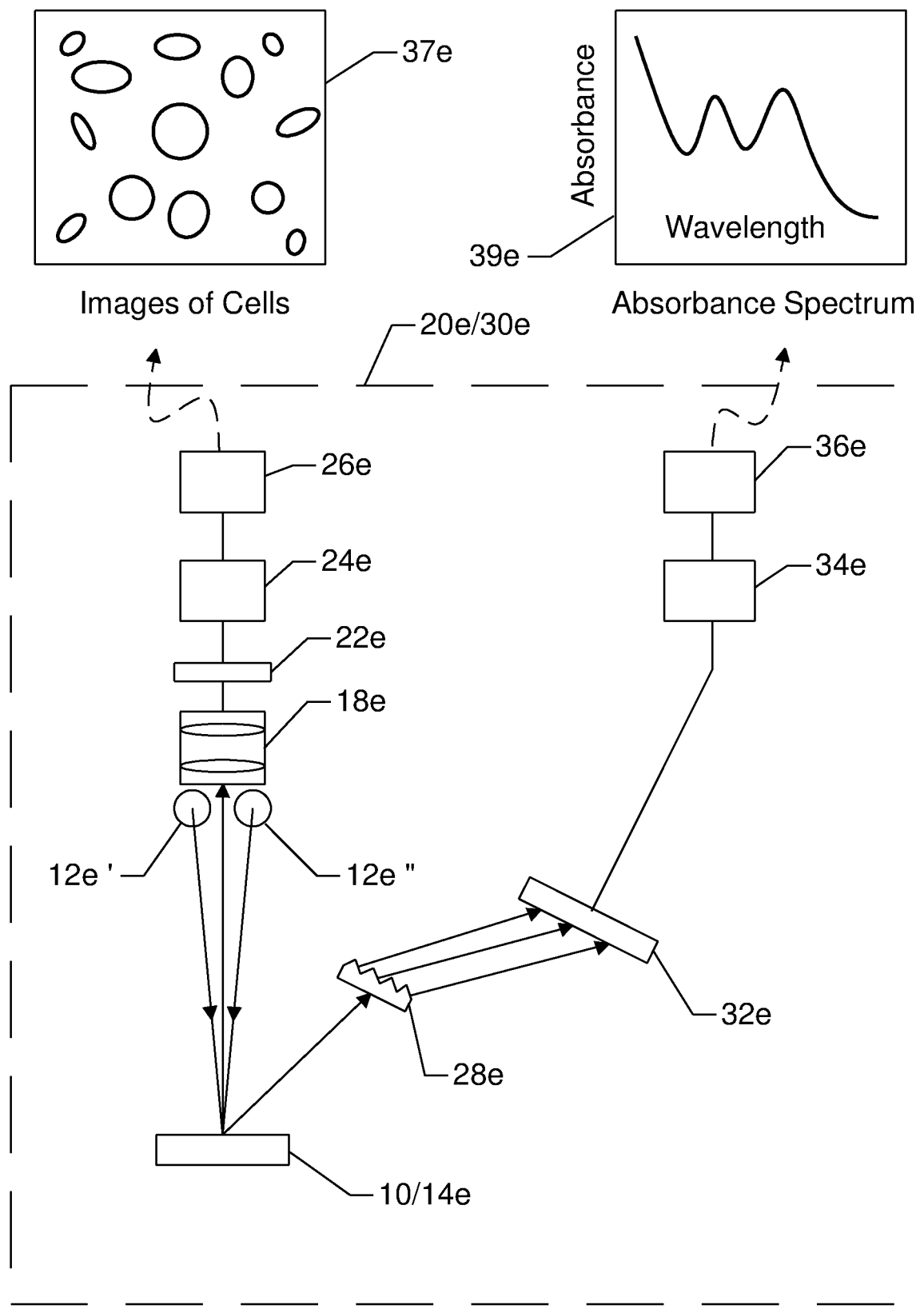
FIG. 6 is a block diagram of an example of a fifth embodiment of a system 30e (upper panel) for measuring one or more analyte quantities per unit volume of blood and one or more formed element quantities per unit volume of blood, in a blood sample. Output displays of the system (upper left and right panels) are provided as non-limiting examples.
Figure 9:
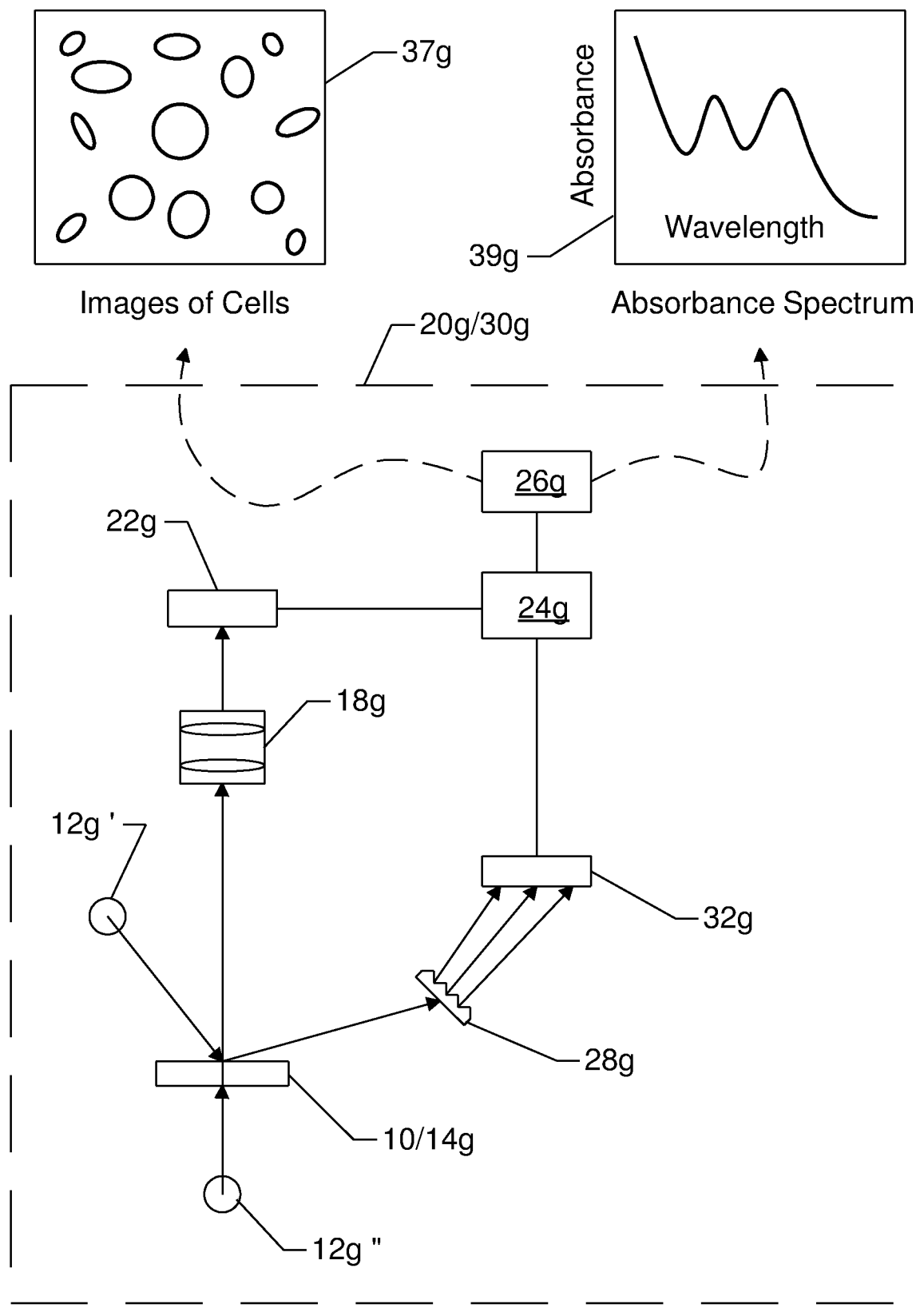
FIG. 9 is a block diagram of an example of a seventh embodiment of a system 30g (lower panel) for measuring one or more analyte quantities per unit volume of blood and one or more formed element quantities per unit volume of blood, in a blood sample. Output displays of the system (upper left and right panels) are provided as non-limiting examples.

In the system described, the means for directing the first and second sets of EMR emerging from the blood sample to the one-dimensional multi-channel detector and the two-dimensional multi-channel detector may involve the use of: 1) a beam splitter (see 16a in FIG. 2, 16c in FIG. 4, and 16f in FIG. 7); 2) a pivotal mirror (see 17b in FIG. 3); 3) a combination of transmitted emerging EMR and reflected emerging EMR (see system 30d in FIG. 5); or 4) the first set of emerging EMR is transmitted through the sample and the second set of emerging EMR is reflected from the sample; 5) the first set of emerging EMR is reflected from the sample and the second set of emerging EMR is transmitted through the sample; and 6) the first set of emerging EMR and the second set of emerging EMR are reflected from the sample, wherein the general direction of the first set of emerging EMR and the general direction of the second set of emerging EMR define an angle less than 90 degrees (see system 30e in FIG. 6 where the source/source of EMR has/have the same location, and see system 30g in FIG. 9 where the sources of EMR have different locations). The beam splitter may be a bifurcated optical fiber (see 16c in FIG. 4), a plate comprising a partially silvered coating or a dielectric coating (see 16f in FIG. 7), and a partially reflecting prism (see 16a in FIG. 2). Beam splitters may be designed to split the incoming EMR into pre-selected ratios of outgoing EMR as required to optimize the outputs (for example, outputs illustrated as 37a-37g and 39a-37g).

The EMR detection techniques used for biochemistry are usually referred to as spectroscopic techniques or spectroscopy. Some Biochemistry tests include for example, blood gases (pH, $pO_2$, i.e., partial pressure of oxygen, and $pCO_2$, i.e., partial pressure of carbon dioxide). These tests usually use biosensor or electrochemical sensor measuring techniques. Therefore, in order to further expand the POCT menu, the cartridge of the present invention may also comprise a biosensor chamber having one or more biosensors for providing additional one or more analyte quantities per unit volume of blood. U.S. Pat. Nos. 8,206,650, 9,470,673 and CA Pat. No. 2,978,737 (hereby incorporated by reference), teach the combination of spectroscopy and biosensor technologies in one cartridge. These patents describe cartridges that use the combination of spectroscopy and biosensor technologies. Additionally, U.S. Pat. Nos. 9,821,307, 9,999,884, 10,272,430, and U.S. Pat. Appl'n Pub. No. US 2019/0224667 (hereby incorporated by reference), teach the combination of spectroscopy and biosensor technologies in one cartridge for conducting coagulation tests, for example PT-INR and ACT. These documents describe cartridges that use the combination of spectroscopy and biosensor technologies, cartridges capable of measuring blood gases and electrolytes (examples of Biochemistry tests, using biosensors), bilirubin and full CO-oximetry (examples of Biochemistry tests using spectroscopy), and PT-INR and ACT (examples of Coagulation tests using spectroscopy).

The cartridge used in the system described herein, comprises an optical chamber having a cavity for containing some of the blood sample, sandwiched between two optical windows, wherein at least one of the optical windows is transparent or translucent. Some other examples of an optical chamber may comprise a cavity for containing some of the blood sample, sandwiched between two optical windows, wherein at least one of the optical windows comprise a reflecting surface for reflecting EMR after the illuminating EMR has penetrated the sample, or a surface for absorbing EMR not reflected by formed elements of blood. The two optical windows are substantially parallel to each other, and the depth of the cavity is preferably about 50-200 micrometers. The area of the transparent or translucent optical window in contact with the blood sample is preferably about 1-100 square millimeters.

Any type of cartridge with an optical chamber may be used, or modified as required to ensure alignment of the optical chamber with the path of EMR that is used to interrogate a sample. Non-limiting examples of suitable cartridges that may be used include those shown in FIGS. 10-13 described herein; and those as described in U.S. Pat. Nos. 8,206,650, 9,470,673, 9,821,307, 9,999,884, 10,272,430, and U.S. Pat. Appl'n Pub. No. US 2019/0224667, and CA Pat. No. 2,978,737 (each of which are incorporated herein by reference). Cartridges may be made of any suitable material, for example, but not limited to a clear polymeric material, a clear plastic, for example, polymethyl methacrylate (PMMA, plexiglass) or polyethylene terephthalate (PET), a material that is transparent to a wavelength of electromagnetic radiation used to interrogate the sample, or a combination thereof. A list of suitable polymers is provided in Table 2 of U.S. Ser. No. 10,272,430 (which is incorporated herein by reference). The optical chamber may be made from the same, or a different, material from that of the cartridge body, provided that the material used for the optical chamber is transparent to a wavelength of electromagnetic radiation used to interrogate the sample.

Still regarding the system described herein, the cartridges may comprise at least one reagent, for example but not limited to, a hemolyzing reagent (for example but not limited to deoxycholate), an anticoagulant (for example but not limited to heparin), a reagent used to measure PT-INR (for example, but not limited to thromboplastin), and a staining reagent (for example but not limited to eosin), preferably in dry form. The at least one reagent may be lyophilized, heat-dried or vacuum dried, and disposed anywhere between the top opening of the sample storage well and one of a vent and a cartridge exit. In some cartridge embodiments, the at least one dry reagent may be disposed in the post-optical chamber conduit. Some of the cartridges may comprise a sealed blister containing a liquid reagent or a diluent (see for example FIGS. 20 and 21, and supporting text, in US 2019/00224667, which is incorporated herein by reference), and the system may further comprise means for releasing the liquid reagent and diluent and means for mixing the blood and the liquid reagent or diluent. In some embodiments of cartridges, release of liquid reagents and diluents are metered. By way of example, which should not be considered limiting in any way, cartridge 10E (see FIGS. 14A-14Y) describes a metering system for liquids contained in blister pouches (also referred to as blisters). As shown in Table 1, the red cell count is about one thousand times the white cell count, therefore in order to avoid over sampling of the red cells, dilution of the sample may be preferred. Although diluting the blood sample is one way of performing red blood cell count using the "Coulter Principle" and the manual hemocytometer, another method may be magnifying a small area of the optical chamber in order to decrease the number of red blood cells counted and at the same time increasing the spaces between the red blood cells, and using a high resolution camera having a pixel pitch between one quarter and one half the size of the red blood cell. Therefore, a preferable pixel pitch for counting red blood cells is less than 4 µm, and a preferable pixel pitch for at least counting white blood cells is 1-10 µm (see Table 1 for nominal sizes of formed elements of blood). Another aspect of the invention described herein is electronic magnification of the image after the image is formed on two-dimensional multi-channel detector.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−25% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The terms "operatively connected", "in operative communication", "in fluid communication" or "fluidly connected" and the like, describe elements of the cartridge, for example, channels, ducts, conduits, tunnels, passageways, that permit either fluid flow, gas flow, or both fluid and gas flow between the various compartments or elements within the cartridge that are connected by the channels, ducts, conduits, tunnels, passageways and the like.

Detailed description of features of examples of the invention is described with reference to the accompanying drawings. These examples are to be considered non-limiting, and a person having ordinary skill in the art should understand that variations are within the scope of the invention, even though they are not explicitly illustrated. The same reference numerals are used for similar elements in different examples; in some cases, letters are appended to the end of the reference numerals to denote the embodiment of the invention illustrated. For example, the letters (lowercase) "a" (FIG. 2), "b" (FIG. 3), "c" (FIG. 4), "d" (FIG. 5), "e" (FIG. 6), "f" (FIG. 7) and "g" (FIG. 9), are used to refer to the $1^{st}$, $2^{nd}$, $3^{rd}$, $4^{th}$, $5^{th}$, $6^{th}$ and $7^{th}$ embodiments or examples of the invention (system), respectively; and the letters (uppercase) "A" (FIGS. 10A-10K), "B" (FIGS. 11A-11K), "C" (FIGS. 12A-12J), "D" (FIGS. 13A-13E) and "E" (FIGS. 14A-14Y), are used to refer to the $1^{st}$, $2^{nd}$, $3^{rd}$, $4^{th}$ and $5^{th}$ embodiments or examples of the invention (cartridge), respectively. It should be noted that absence of a letter after a reference numeral may refer to multiple examples of the invention, for example, 13 refers to an optical chamber in all the examples of cartridges (10A-10E). For easy reference, Table 2 provides a list of the reference numerals used, and a brief description of the corresponding structural features.

TABLE 2

Description of Structural Features.

| Reference Numerals | Description of Structural Features |
|---|---|
| 10 | A generic cartridge for use with analyzers 20a, 20b, 20c, 29d, 20e, 20f and 20g |
| 10A | A first embodiment of a cartridge |
| 10B | A second embodiment of a cartridge |
| 10C | A third embodiment of a cartridge |
| 10D | A fourth embodiment of a cartridge |
| 10E | A fifth embodiment of a cartridge |
| 12a | Source of electromagnetic radiation (EMR) in system 30a |
| 12b | Source of EMR in system 30b |
| 12c | Source of EMR in system 30c |
| 12d' & 12d" | Sources (e.g. a circular array of LEDs, which may comprise white LEDs and small band pass LEDs) of EMR in system 30d |
| 12e' & 12e" | Sources (e.g. a circular array of LEDs, which may comprise white LEDs and small band pass LEDs) of EMR in system 30e |
| 12f | Source of EMR in system 30f |
| 12g' & 12g" | Source of EMR in system 30g |
| 13 | An optical chamber of cartridge 10A, 10B, 10C and 10D |
| 14a | A receptor in analyzer 20a for receiving a cartridge 10 |
| 14b | A receptor in analyzer 20b for receiving a cartridge 10 |
| 14c | A receptor in analyzer 20c for receiving a cartridge 10 |
| 14d | A receptor in analyzer 20d for receiving a cartridge 10 |
| 14e | A receptor in analyzer 20e for receiving a cartridge 10 |
| 14f | A receptor in analyzer 20f for receiving a cartridge 10 |
| 14g | A receptor in analyzer 20g for receiving a cartridge 10 |
| 15a | An opening or aperture in receptor 14a for illuminating optical chamber 13 with EMR |
| 16a | A beam splitter (e.g. a partially reflecting prism) of system 30a |

TABLE 2-continued

Description of Structural Features.

| Reference Numerals | Description of Structural Features |
|---|---|
| 16c | A beam splitter (e.g. a bifurcated optical fiber comprising one or more strands of optical fiber) of system 30c |
| 16f | A beam splitter (e.g. a plate comprising a partially silvered coating, or a plate comprising a dielectric coating) of system 30f |
| 17b | A pivotal mirror of system 30b for directing EMR transmitted through the blood sample, to either detector 22b or detector 32b, depending on the position of the mirror |
| 18b | A magnifying system of system 30b |
| 18c | A magnifying system of system 30c |
| 18d | A magnifying system of system 30d |
| 18e | A magnifying system of system 30e |
| 18g | A magnifying system of system 30g |
| 19b | A pivot for pivotal mirror 17b |
| 20a | A first embodiment of an analyzer of system 30a |
| 20b | A second embodiment of an analyzer of system 30b |
| 20c | A third embodiment of an analyzer of system 30c |
| 20d | A fourth embodiment of an analyzer of system 30d |
| 20e | A fifth embodiment of an analyzer of system 30e |
| 20f | A sixth embodiment of an analyzer of system 30f |
| 20g | A seventh embodiment of an analyzer of system 30g |
| 22a | A two-dimensional multi-channel detector of system 30a |
| 22b | A two-dimensional multi-channel detector of system 30b |
| 22c | A two-dimensional multi-channel detector of system 30c |
| 22d | A two-dimensional multi-channel detector of system 30d |
| 22e | A two-dimensional multi-channel detector of system 30e |
| 22f | A two-dimensional multi-channel detector of system 30f |
| 22g | A two-dimensional multi-channel detector of system 30g |
| 24a | An analog to digital converter of system 30a |
| 24b | An analog to digital converter of system 30b |
| 24c | An analog to digital converter of system 30c |
| 24d | An analog to digital converter of system 30d |
| 24e | An analog to digital converter of system 30e |
| 24f | An analog to digital converter of system 30f |
| 24g | An analog to digital converter of system 30g |
| 26a | A processor of system 30a |
| 26b | A processor of system 30b |
| 26c | A processor of system 30c |
| 26d | A processor of system 30d |
| 26e | A processor of system 30e |
| 26f | A processor of system 30f |
| 26g | A processor of system 30g |
| 28a | An EMR dispersing element (e.g., a dispersion prism) of system 30a |
| 28b | An EMR dispersing element (e.g., a transmission grating) of system 30b |
| 28c | An EMR dispersing element (e.g., a reflecting grating) of system 30c |
| 28d | An EMR dispersing element (e.g., a reflecting grating) of system 30d |
| 28e | An EMR dispersing element (e.g., a transmission grating) of system 30e |
| 28f | An EMR dispersing element (e.g., a prism) of system 30f |
| 28g | An EMR dispersing element (e.g., a transmission grating) of system 30g |
| 30a | A first embodiment of a system comprising an analyzer 20a and a cartridge 10 |
| 30b | A second embodiment of a system comprising an analyzer 20b and a cartridge 10 |
| 30c | A third embodiment of a system comprising an analyzer 20c and a cartridge 10 |
| 30d | A fourth embodiment of a system comprising an analyzer 20d and a cartridge 10 |
| 30e | A fifth embodiment of a system comprising an analyzer 20e and a cartridge 10 |
| 30f | A sixth embodiment of a system comprising an analyzer 20f and a cartridge 10 |
| 30g | A sixth embodiment of a system comprising an analyzer 20g and a cartridge 10 |
| 32a | A one-dimensional multi-channel detector of system 30a |
| 32b | A one-dimensional multi-channel detector of system 30b |
| 32c | A one-dimensional multi-channel detector of system 30c |
| 32d | A one-dimensional multi-channel detector of system 30d |
| 32e | A one-dimensional multi-channel detector of system 30e |
| 32f | A one-dimensional multi-channel detector of system 30f |
| 32g | A one-dimensional multi-channel detector of system 30g |
| 34b | An analog to digital converter of system 30b |
| 34c | An analog to digital converter of system 30c |
| 34d | An analog to digital converter of system 30e |
| 34e | An analog to digital converter of system 30d |
| 34f | An analog to digital converter of system 30f |
| 36b | A processor of system 30b |
| 36c | A processor of system 30c |
| 36d | A processor of system 30d |
| 36e | A processor of system 30e |
| 36f | A processor of system 30f |
| 37a | An example of a display of digital information output of a two-dimensional multi-channel detector of system 30a. In this example, the outline of cells is shown. The cells can be counted using commercially available or public access software. |
| 37b | An example of a display of digital information output of a two-dimensional multi-channel detector of system 30b. In this example, the outline of cells is shown. The cells can be counted using commercially available or public access software. |
| 37c | An example of a display of digital information output of a two-dimensional multi-channel detector of system 30c. In this example, the outline of cells is shown. The cells can be counted using commercially available or public access software. |
| 37d | An example of a display of digital information output of a two-dimensional multi-channel detector of system 30d. In this example, the outline of cells is shown. The cells can be counted using commercially available or public access software. |
| 37e | An example of a display of digital information output of a two-dimensional multi-channel detector of system 30e. In this example, the outline of cells is shown. The cells can be counted using commercially available or public access software. |
| 37f | An example of a display of digital information output of a two-dimensional multi-channel detector of system 30f. In this example, the outline of cells is shown. The cells can be counted using commercially available or public access software. |
| 37g | An example of a display of digital information output of a two-dimensional multi-channel detector of system 30g. In this example, the outline of cells is shown. The cells can be counted using commercially available or public access software. |
| 39a | An example of a display of digital information output of a one-dimensional multi-channel detector of system 30a. In this example, the absorbance spectrum of blood is shown. The digital information is used to develop |

TABLE 2-continued

Description of Structural Features.

| Reference Numerals | Description of Structural Features |
|---|---|
| | calibration algorithms for one or more blood analytes (e.g. bilirubin and various hemoglobin species), and subsequently, the calibration algorithms can be used to predict the one or more analyte quantities in other blood samples. |
| 39b | An example of a display of digital information output of a one-dimensional multi-channel detector of system 30b. In this example, the absorbance spectrum of blood is shown. The digital information is used to develop calibration algorithms for one or more blood analytes (e.g. bilirubin and various hemoglobin species), and subsequently, the calibration algorithms can be used to predict the one or more analyte quantities in other blood samples. |
| 39c | An example of a display of digital information output of a one-dimensional multi-channel detector of system 30c. In this example, the absorbance spectrum of blood is shown. The digital information is used to develop calibration algorithms for one or more blood analytes (e.g. bilirubin and various hemoglobin species), and subsequently, the calibration algorithms can be used to predict the one or more analyte quantities in other blood samples. |
| 39d | An example of a display of digital information output of a one-dimensional multi-channel detector of system 30d. In this example, the absorbance spectrum of blood is shown. The digital information is used to develop calibration algorithms for one or more blood analytes (e.g. bilirubin and various hemoglobin species), and subsequently, the calibration algorithms can be used to predict the one or more analyte quantities in other blood samples. |
| 39e | An example of a display of digital information output of a one-dimensional multi-channel detector of system 30e. In this example, the absorbance spectrum of blood is shown. The digital information is used to develop calibration algorithms for one or more blood analytes (e.g. bilirubin and various hemoglobin species), and subsequently, the calibration algorithms can be used to predict the one or more analyte quantities in other blood samples. |
| 39f | An example of a display of digital information output of a one-dimensional multi-channel detector of system 30f. In this example, the absorbance spectrum of blood is shown. The digital information is used to develop calibration algorithms for one or more blood analytes (e.g. bilirubin and various hemoglobin species), and subsequently, the calibration algorithms can be used to predict the one or more analyte quantities in other blood samples. |
| 39g | An example of a display of digital information output of a one-dimensional multi-channel detector of system 30g. In this example, the absorbance spectrum of blood is shown. The digital information is used to develop calibration algorithms for one or more blood analytes (e.g. bilirubin and various hemoglobin species), and subsequently, the calibration algorithms can be used to predict the one or more analyte quantities in other blood samples. |
| 46a | A collimation system for producing substantially parallel rays of EMR |
| 48f | A focusing system for projecting a real image of the blood sample on to the two-dimensional multi-channel detector |
| 50A | A first housing member of cartridge 10A |
| 50B | A first housing member of cartridge 10B |
| 50C | A first housing member of cartridge 10C |
| 50D | A first housing member of cartridge 10D |
| 50E | A first housing member of cartridge 10E |
| 51 | A sample storage well of cartridges 10A, 10B and 10C |
| 53 | A top opening (or top portion) of a sample storage well 51 |
| 55 | A bottom opening (or bottom portion) of a sample storage well 51 |
| 57A | A sample inlet portion of cartridge 10A, which comprises some elements of the cartridge that interacts with the cap 70A |
| 57B | A sample inlet portion of cartridge 10B, which comprises some elements of the cartridge that interacts with the cap 70B |
| 57D | A sample inlet portion of cartridge 10D, which comprises some elements of the cartridge that interacts with the cap 70D |
| 57E | A sample inlet portion of cartridge 10E, which comprises some elements of the cartridge that interacts with the cap 70E |
| 59A | A flat surface of inlet portion 57A |
| 59B | A flat surface of inlet portion 57B |
| 59D | A flat surface of inlet portion 57D |
| 59E | A flat surface of inlet portion 57E |
| 60A | A second housing member of cartridge 10A |
| 60B | A second housing member of cartridge 10B |
| 60C | A second housing member of cartridge 10C |
| 60D | A second housing member of cartridge 10D |
| 60E | A second housing member of cartridge 10E |
| 63A | An air bladder communication port of a sample inlet portion 57A of cartridge 10A |
| 63B | An air bladder communication port of a sample inlet portion 57B of cartridge 10A |
| 63D | An analyzer pump communication port of a sample inlet portion 57D of cartridge 10D |
| 65A | An air bladder duct for providing fluid connection between an air bladder 67A and an air bladder communication port 63A |
| 65B | An air bladder duct for providing fluid connection between an air bladder 67B and an air bladder communication port 63B |
| 65D | An analyzer pump duct for providing fluid connection between an analyzer pump and an analyzer pump communication port 63D |
| 67A | An air bladder of cartridge 10A |
| 67B | An air bladder of cartridge 10B |
| 67E | An air bladder of cartridge 10E |
| 70A | A cap for closing inlet portion 57A of cartridge 10A |
| 70B | A cap for closing inlet portion 57B of cartridge 10B |
| 70C | A cap for closing inlet portion 57B of cartridge 10C |
| 70D | A cap for closing inlet portion 57D of cartridge 10D |
| 70E | A cap for closing inlet portion 57E of cartridge 10E |
| 71A | A flexible member of air bladder 67A |
| 71B | A flexible member of air bladder 67B |
| 71E | A flexible member of air bladder 67E |
| 73A | A top side of cap 70A |
| 73B | A top side of cap 70B |
| 73E | A top side of cap 70E |
| 75A | An underside of cap 70A, having a cap flat surface 76A and a cap recess 77A |
| 75B | An underside of cap 70B, having a cap flat surface 76B and a cap recess 77B |
| 75D | An underside of cap 70D, having a cap flat surface 76D and a caprecess 77D |
| 75E | An underside of cap 70E, having a cap flat surface 76E and a cap inlet 78E |
| 76A | A cap flat surface disposed at the underside 75A of cap 70A |
| 76B | A cap flat surface disposed at the underside 75B of cap 70B |
| 76D | A cap flat surface disposed at the underside 75D of cap 70D |
| 76E | A cap flat surface disposed at the underside 75E of cap 70E |
| 77A | A cap recess in the underside 75A of cap 70A |
| 77B | A cap recess in the underside 75B of cap 70B |
| 77D | A cap recess in the underside 75D of cap 70D |

TABLE 2-continued

Description of Structural Features.

| Reference Numerals | Description of Structural Features |
|---|---|
| 78E | A cap inlet to cap mixing chamber 79E |
| 79E | A cap mixing chamber for mixing blood and diluent to make diluted blood |
| 81 | A first optical window of optical chamber 13 |
| 83 | A second optical window of optical chamber 13 |
| 85A | A vent of cartridge 10A |
| 85B | A vent of cartridge 10B |
| 85D | A vent of cartridge 10D |
| 85E | A cap vent on cartridge cap 70E of cartridge 10E |
| 87A' & 87A" | Hinges for hingedly attaching cap 70A to body of cartridge 10A |
| 88B' | A hole in the first housing member 50B of cartridge 10B for receiving pivot 89B |
| 88E' | A hole in the first housing member 50E of cartridge 10E for receiving pivot 89E |
| 88B" | A hole in the second housing member 60B of cartridge 10B for receiving pivot 89B |
| 88E" | A hole in the second housing member 60E of cartridge 10E for receiving pivot 89E |
| 89B | A pivot for hingedly attaching cap 70B to body of cartridge 10B |
| 89E | A pivot for hingedly attaching cap 70E to body of cartridge 10E |
| 91A | A cap latch of cap 70A |
| 91B | A cap latch of cartridge 10B |
| 91E | A cap latch of cartridge 10E |
| 92 B | A recess in cap latch 91B for engaging cap 70B |
| 92 E | A recess in cap latch 91E for engaging cap 70E |
| 93A'% 93A" | Holes for anchoring hinges 87A' and 87A" |
| 94B | Groove disposed at the underside 75B and at the sweeping portion of cap 70B for storing excess sample |
| 94E | Groove disposed at the inlet portion 94E for storing excess sample |
| 95A | A cap latch catch for engaging cap latch 91A |
| 97A | An optical chamber inlet conduit, or pre-optical chamber conduit, of cartridge 10A |
| 97B | An optical chamber inlet conduit, or pre-optical chamber conduit, of cartridge 10B |
| 97C | An optical chamber inlet conduit, or pre-optical chamber conduit, of cartridge 10C |
| 97D | An optical chamber inlet conduit, or pre-optical chamber conduit, of cartridge 10D |
| 97E | An optical chamber inlet conduit, or pre-optical chamber conduit, of cartridge 10E |
| 99A | An optical chamber exit conduit, or post-optical chamber conduit, of cartridge 10A |
| 99B | An optical chamber exit conduit, or post-optical chamber conduit, of cartridge 10B |
| 99C | An optical chamber exit conduit, or post-optical chamber conduit, of cartridge 10C |
| 99D | An optical chamber exit conduit, or post-optical chamber conduit, of cartridge 10D |
| 99E | An optical chamber exit conduit, or post-optical chamber conduit, of cartridge 10E, which provides fluid connection between the optical chamber 13 and the air bladder 67E |
| 100A | A double-sided sticky gasket of cartridge 10A |
| 100B | A double-sided sticky gasket of cartridge 10B |
| 100C | A double-sided sticky gasket of cartridge 10C |
| 100D | A double-sided sticky gasket of cartridge 10D |
| 100E | A double-sided sticky gasket of cartridge 10E |
| 200 | A conductivity sensor comprising a pair of conductivity electrodes (also referred to as probes), for performing several functions, e.g., controlling air bladder stepper motor; and measuring hematocrit. |
| 201' & 201" | Ends of sensor 200 having applied voltage via a relay, exposed in optical chamber exit conduit 99B. The ends function as an open switch when the conduit is not occupied by blood, and function as a closed switch when blood bridges the gap between the ends. When the switch is closed, a current travels to the relay in the analyzer, and the relay could control a stepper motor, for example. |
| 203' & 203" | Ends (pins) of sensor 200 projecting out of cartridge 10B. When the cartridge is properly inserted in the analyzer receptor, the sensor could develop electrical communication with relay, for example. The relay is used to apply a voltage across sensor ends 201' and 201", and activate/deactivate air bladder stepper motor, for example, and could also be used to measure hematocrit. |
| 211C | A sealing member installed in cartridge exit duct 217C in cartridge 10C, for frictionally engaging the outer surface of an analyzer pump hollow needle. |
| 211D | A sealing member installed in cartridge air inlet duct 217D in cartridge 10D, for frictionally engaging the outer surface of an analyzer pump hollow needle. |
| 217C | A cartridge exit duct for housing sealing member 211C |
| 217D | A cartridge air inlet duct for housing sealing member 211D |
| 219C | A cartridge exit, a portion of cartridge exit duct 217C of cartridge 10C, for establishing operative communication with an analyzer pump |
| 219D | A cartridge air inlet, a portion of cartridge air inlet duct 217D of cartridge 10D, for establishing operative communication with an analyzer pump |
| 221C | A sample storage well boss of cartridge 10C for increasing the sample storage well storage capacity. |
| 223C | A cap breathable plug of cartridge 10C, an example of a cap vent; may also be referred to as a cap vent |
| 225C | A hydrophobic insert disposed close to the junction of the bottom opening 55 of the sample storage well 51 and the optical chamber inlet conduit 97C of cartridge 10C, for providing means for minimizing, mitigating, or modifying blood flow out of the sample storage well 51. |
| 227C | Recess in first housing member 50C of cartridge 10C for installing hydrophobic insert 225C |
| 229C | Recess in second housing member 60C of cartridge 10C for installing hydrophobic insert 225C |
| 301E | A sealed blister for storing a liquid, for example a diluent for diluting blood or a liquid reagent |
| 303E | A diluent holding conduit for temporarily holding the diluent released from the blister 301E |
| 305E | A blister window in the first housing member 50E for accessing the sealed blister 301E |
| 313E | A first directional valve element of cartridge 10E, which for example, could be an elastomeric flap |
| 315E | A smaller section of the first directional valve element 313E that is flappable for closing of junction where the diluent holding conduit 303E intersects with the blister outlet conduit 317E |
| 316E | A larger section of the first directional valve element 313E that is used to anchor element 313E in receptor 349E (see FIG. 14A) |
| 317E | A blister outlet conduit for transferring blister fluid from blister 301E after it is ruptured, to the diluent holding conduit 303E |
| 319E | A transfer conduit for transferring blister fluid from the diluent holding conduit 303E to the second directional valve 321E |
| 321E | A second directional valve stem for: 1) fluidly connecting bottom opening 55 of sample storage well 51 and a blood vent 323E; 2) fluidly connecting diluent holding conduit 303E and diluent vent 325E; and 3) fluidly connecting the diluent holding conduit 303E and the bottom opening 55 of sample storage well 51 |
| 323E | A blood vent for facilitating filling of the sample storage well 51 |
| 325E | A diluent vent for facilitating filling of the diluent holding conduit 303E |
| 327E | A hole in the second directional valve 321E for providing direct fluid connection between the transfer conduit 319E and the diluent vent 325E |

TABLE 2-continued

Description of Structural Features.

| Reference Numerals | Description of Structural Features |
|---|---|
| 329E | A spike for rupturing the sealed blister 301E |
| 331E | A hole in spike 329E for draining diluent from the ruptured blister 301E |
| 333E | A top flange of the second directional valve stem 321E<br>Note: A space exists between the outer portion of the top flange 333E and the first housing member 50E, unlike bottom flange 335E which comprises an O-ring 337E |
| 335E | A bottom flange of the second directional valve stem 321E |
| 337E | An O-ring around the bottom flange 325E of the second directional valve stem 321E for sealing the bottom flange against the cavity in the second housing member 60E |
| 339E | A neck for joining the top flange 333E and the bottom flange 335E |
| 341E | A locating element in the top flange 333E for aligning the hole 327E with a portion of the transfer conduit 319E |
| 343E | A sealing surface of the bottom flange 335E |
| 345E | A sealing surface of the top flange 333E |
| 347E | A bottom laminate for covering the blister outlet conduit 317E and the transfer conduit 319E |
| 349E | A cavity (or receptor) for housing the first directional valve element 313E |
| 351E | Compressible member for supporting blister 301E over spike 329E |

Overview of System 30a as a Non-Limiting Example

Figure 2:
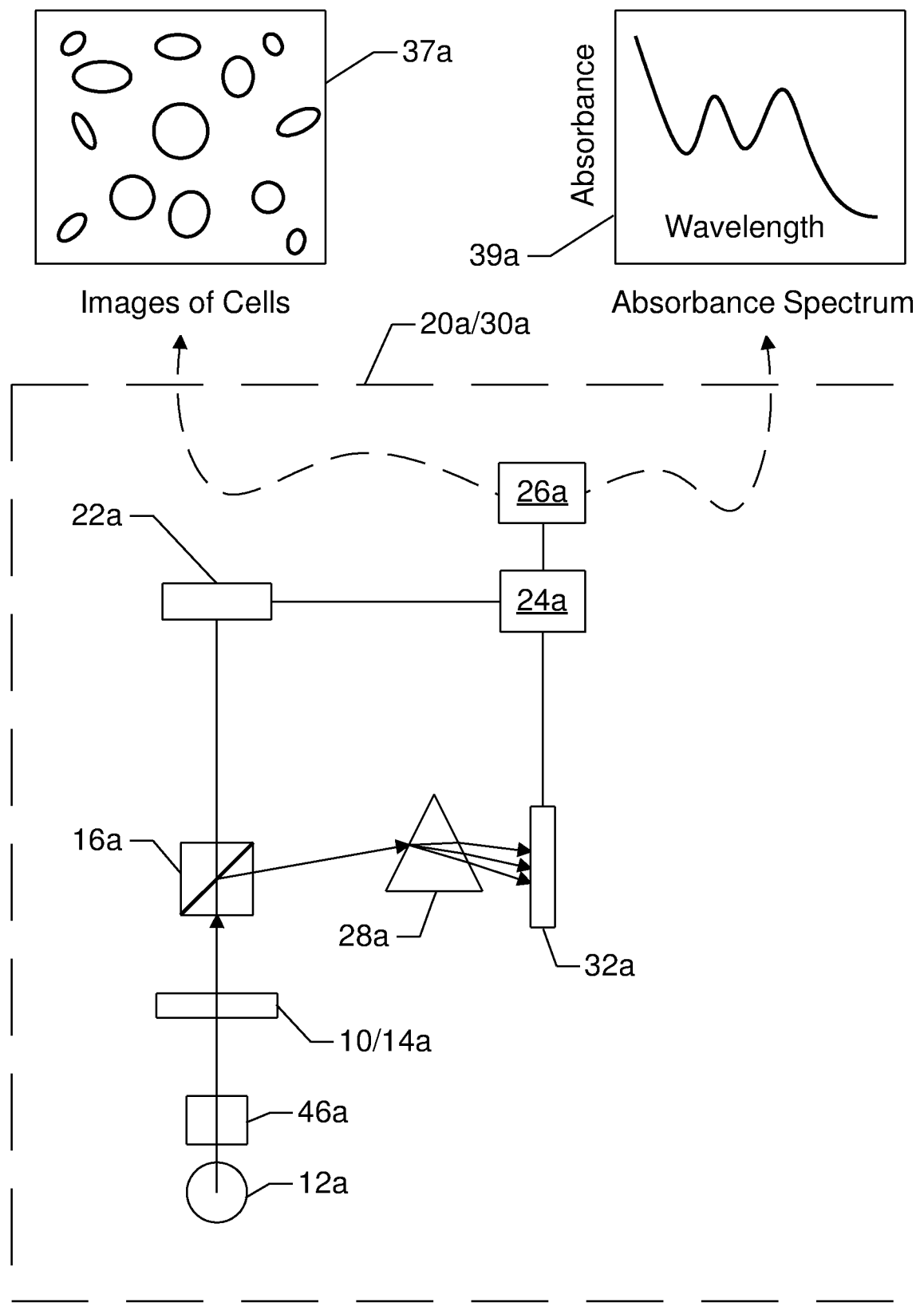
FIG. 2 is a block diagram of an example of a first embodiment of a system 30a (lower panel) for measuring one or more analyte quantities per unit volume of blood and one or more formed element quantities per unit volume of blood, in a blood sample. Output displays of the system (upper left and right panels) are provided as non-limiting examples.

The first embodiment of a system 30a for measuring one or more analyte quantities per unit volume of blood (i.e., the concentration of the analyte) using spectroscopic technique, and one or more formed element quantities per unit volume of blood (i.e., a cell count) using an imaging technique, is illustrated in FIG. 2. System 30a comprises a source of EMR 12a, which may represent a polychromatic source of EMR or a plurality of monochromatic EMR. Depending on the source of EMR, a collimation system 46a may be used to produce substantially parallel rays of EMR for interrogating or illuminating the blood sample in an optical chamber (see 13 in FIGS. 10H & 10K) of a cartridge 10 (10 may be considered a generic cartridge, and could be at least one of 10A, 10B, 10C or 10D, or a similar cartridge described in the prior art) in a receptor 14a of an analyzer 20a (see FIGS. 8A-8C).

The EMR transmitted through the blood sample in the optical chamber 13 of a cartridge 10 is referred to as emerging EMR. The emerging EMR is split using a partially reflective prism 16a, into a first set (or portion) of emerging EMR that is directed on to a one-dimensional multi-channel detector 32a, and a second set of emerging EMR that is directed on to a two-dimensional multi-channel detector 22a. Other embodiments described later will illustrate the use of other means for directing the path of emerging EMR. Prior to directing the first set of emerging EMR to detector 32a, the first set of emerging EMR is directed to a dispersing element 28a for dispersing the first set of emerging EMR into its component wavelengths, to produce dispersed EMR. The dispersing element 28a in this embodiment is a dispersing prism. However, other dispersing elements for example a grating (e.g. a diffraction, transmission or reflective grating), may be used, as shown in other embodiments. The dispersed EMR is then projected on to a wavelength-calibrated one-dimensional multi-channel detector for receiving the dispersed EMR and generating wavelength-specific electrical signals. The one-dimensional multi-channel detector may comprise photodiodes or charge-coupled devices. The wavelength-specific electrical signals generated in the one-dimensional multi-channel detector are digitized using an analog to digital converter 24a, to produce wavelength-specific digital information or data. Subsequently, the processor 26a applies analyte-specific calibration algorithms (installed in the processor) to the wavelength-specific digital information to produce one or more analyte quantities per unit volume of blood. An example of a display of digital information output of the one-dimensional multi-channel detector of system 30a is shown as 39a. In this example, an absorbance spectrum of the blood is shown. Prior to testing unknown blood samples, digital information and the analyte concentrations from a set of known samples are used to develop calibration algorithms for one or more blood analytes (e.g. bilirubin and various hemoglobin species). Subsequently, the calibration algorithms can be used to predict the one or more analyte quantities in other blood samples (unknown samples). An example of a spectroscopic method that may be used as described above is provided in U.S. Pat. No. 6,651,015 to Samsoondar (incorporated herein by reference). Additional information on spectroscopic measurement is also provided below under the title "Spectroscopic measurement".

To produce a plurality of wavelengths, the source of EMR 12a may be a tungsten lamp (other lamps may be used), white light-emitting diodes (LEDs), one or more lasers, one or more LEDs, and any combination thereof, as is well known in the art. An optional collimation system 46a is shown between the source of EMR 12a and the receptor 14a for producing substantially parallel rays of EMR, but other embodiments may have a collimation system installed between the receptor 14a and the detector 22a.

Although cartridge 10A is provided as an example for system 30a illustrated in FIGS. 8A-8C, any suitable cartridge may be used. In addition to an optical chamber 13, the cartridges may contain, for example, conductivity sensors and a biosensor, preferably downstream of the optical chamber. Biosensors, also referred to as electrochemical sensors, may be used to measure, for example, electrolytes and blood gases. In the case of blood gases, the results are given as the partial pressure of oxygen or carbon dioxide, measured in mm mercury. Hematocrit may be measured using optical measurement of the unclotted or clotted blood at one or more wavelengths, and the hematocrit measurement may be used to correct a PT-INR measurement for the patient's hematocrit. Hematocrit may also be measured using for example, a cartridge comprising a conductivity sensor 200 illustrated in FIGS. 11A, 11B, 11G and 11H. If the cartridge contains a hemolysing reagent in the post-optical chamber conduit (discussed below), the conductivity sensor must be disposed in the cartridge where unlysed blood can come in contact with the sensor. Cartridge 10A shown in FIG. 8A is further illustrated in FIGS. 10A-10J, cartridge 10B is illustrated in FIGS. 11A-11K, cartridge 11C is illustrated in FIGS. 12A-12J; and cartridge 10D is illustrated in FIGS. 13A-13E. Other examples of cartridges are described in U.S. Pat. No. 9,470,673, CA Pat. No. 2,978,737, and U.S. Pat. Appl'n Pub. No. US 2019/0224667 (each of which is hereby incorporated by reference). These publications describe threaded as well as hinged caps, and although examples of hinged caps are provided in this application, cartridges that use threaded caps are considered to be within the scope of the present invention.

Still referring to FIG. 2, the second portion of emerging EMR is directed on to the two-dimensional multi-channel detector 22*a*. In this embodiment, the EMR transmitted through a beam splitter 16*a* is directed to a two-dimensional multi-channel detector 22*a* and the reflected portion is directed on to the one-dimensional multi-channel detector 32*a* via a dispersing prism 28*a*. In other embodiments, the EMR transmitted through the beam splitter 16*a* may be directed to detector 32*a* via the dispersing prism 28*a*, and the reflected portion may be directed to detector 22*a*. Whereas polychromatic EMR is required for the spectroscopy, either monochromatic or polychromatic EMR may be used for cell image formation. Therefore, the source of EMR 12*a* may comprise a combination of monochromatic and polychromatic EMR. Moreover, the beam splitter 16*a* may be designed to selectively transmit EMR and reflect EMR in different selected wavelength ranges.

Still referring to FIG. 2, the signals generated after the second portion of emerging EMR is directed on to the two-dimensional detector 22*a* is digitized using the analog to digital converter 24*a*, and the digital information may be displayed as shown in 37*a*, providing the outline of cells. Cells may also be observed as colored spots, dark spots against a lighter background, and lighter spots against a dark background depending on the type of stain used if any, and the wavelength of EMR used as would be know to one of skill in the art. For example, congo red has a strong absorbance band at 340 nm in the near-ultraviolet region and another at 500 nm near the blue-green transition region of the visible spectrum (about 450 nm to about 700 nm), and transmits red wavelengths above 560 nanometers and thus appears red to the eye; malachite green has a strong absorbance band centered at 600 nm near the yellow-red transition region, with a wide transmission band between 400 nm and 550 nm of the visible spectrum, and appears green to the eye; methylene blue has a strong absorbance band centered at 660 nanometers, in the red region of the visible spectrum, and transmits wavelengths below 600 nanometers, and appears blue to the eye Some embodiments may comprise separate analog to digital converter for detectors 22*a* and 32*a*, as illustrated in FIG. 2, system 30*a*, or in other embodiments, for example system 30*b* (see FIGS. 3; 22*b* and 32*b*).

The cells can be counted, and their distribution characterized using commercially available or public access software which may be installed in the processor 26*a*. An example of public domain imaging software, from the U.S. National Institute of Health may be found at URL: rsb.info.nih.gov/nih-image/. Although one processor is shown (26*a*), the system 30*a* may comprise one or more processors and the one or more processors may be an integral part of the analyzer 20*a* or a separate module in electrical communication with the analyzer 20*a*.

The two-dimensional multi-channel detector 22*a* may be a CCD (charge-coupled device) camera or a CMOS (complementary metal oxide semiconductor) camera. The pixels in the CCD camera and the CMOS camera may, for example, have a pixel pitch between one quarter and one half the size of the formed elements being observed, in order to resolve the formed elements. The magnitude of the sizes of formed elements of blood are provided in Table 1, above.

Spectroscopic Measurement

An embodiment of a system for performing spectroscopic measurement for testing of whole blood comprises an analyzer and a cartridge is included herein. Other terms like spectrophotometric, photometric or optical measurement are sometimes used instead of spectroscopic measurement. With respect to the spectroscopic measurement alone, the analyzer may comprise a source of electromagnetic radiation (EMR) and one or more photodetectors for measuring the EMR reflected from the sample in an optical chamber of the cartridge, or EMR transmitted through the sample in the optical chamber of the cartridge. The source of EMR, which impinges upon, illuminates or interrogates the contents of the optical chamber, may be a tungsten lamp (other lamps may be used), one or more lasers, and one or more light-emitting diodes (LEDs) across a range of wavelengths as is well known in the art, and without being limited in any way. The analyzer may also include a spectrometer, which may comprise multichannel detectors such as a photodiode array (PDA) or a charge-coupled device (CCD), for example, without being limited in any way. The spectrometer may also comprise a prism, a transmission grating or a reflecting (or reflection) grating for dispersing EMR reflected from a sample (i.e., reflectance, denoted by R) or EMR transmitted through a sample (i.e. transmittance, denoted by T), into component wavelengths.

Preferably the spectrometer comprises a multichannel photodetector arranged as a linear PDA detector installed in the spectrometer, for example, a linear repetitive installation of discrete photodiodes on an integrated circuit chip. For measuring transmittance, the source of EMR and the PDA detector should be on opposite sides of the optical chamber, and for measuring reflectance, both the source of EMR and the PDA detector should be on the same side of the optical chamber. For reflectance measurement, the distal optical window of the optical chamber may be used as a reflecting member. Alternatively, a reflecting member may be installed in the cartridge receptor of the analyzer, and in close proximity to the optical window distal to the source of EMR.

For illustration of a method for performing spectroscopic measurement of whole blood, and by way of example which is not to be considered limiting, the PDA detector may have a pixel dispersion of 2 nanometers per pixel (i.e., the pixel or digital resolution), and the PDA detector is calibrated (i.e., wavelength calibration) to read from wavelengths 300 nanometers to 812 nanometers. Two laser beams may be used to conduct wavelength calibration, which is well known by persons having knowledge in the art (see for example U.S. Pat. Nos. 6,372,503, and 6,711,516, which are incorporated herein by reference). In this example, the center of pixel 1 is assigned a wavelength of 300 nanometers (laser #1), and the center of pixel 256 is assigned a wavelength of 812 nanometers (laser #2), thereby providing a wavelength range of 300-812 nanometers. For clarity, since the center of pixel 1 is assigned 300 nanometers, the center of pixel 2 will be assigned 302 nanometers, the center of pixel 3 will be assigned 304 nanometers and so on in increments of 2 nanometers per pixel (the pixel dispersion). The two lasers emit be EMR at any wavelength within the range of 300-812 nanometers, having sufficient spacing so that linear interpolation and linear extrapolation of wavelengths can be conducted. A person skilled in spectroscopy should appreciate that the wavelength range and spectral resolution of the PDA detector depends on several factors, for example, the semiconductor material used to construct the PDA, and grating (e.g. diffraction, transmission or reflective grating) and the orientation of the grating relative to the PDA detector. The source of EMR is a major determinant of the wavelength range. Each pixel is typically scanned in microseconds, which provides sufficient time to accumulate sufficient charge on the photodiode, for example to distinguish a signal from noise and dark current, without saturating the photodiode.

Saturation, or "saturating the photodiode", means that the photodiode has reached a maximum response in current and any additional photons impinging upon the photodiode is usually converted to heat instead of current. Because the scanning time is so short, it is reasonable to say that all the photodiodes in the PDA detector are scanned simultaneously. The photons are converted to electrical current, which is measured and digitized. In this present example, absorbance (sometimes referred to as absorption, denoted by A) may be determined, where $$A = -\log_{10} T.$$

It is well known that transmittance is defined as the fraction of incident light which is transmitted or passes through a sample. Thus:

$T = I/I_o$, where $I_o$ = the intensity of light (or EMR) impinging upon or interrogating the sample (i.e. the incident light) and I = the intensity of light (or EMR) emerging from the sample after passing through the sample.

For calculating transmittance, the amount of EMR impinging upon the optical chamber, $I_o$, may be measured by interrogating an optical chamber containing air. The EMR impinging upon the optical chamber, $I_o$, may be measured before or after every sample measurement, or less frequently and stored in the processor for later use.

As an example, spectroscopic measurements are used to estimate prothrombin time (PT; usually reported as PT-INR; PT-International Normalized Ratio), activated partial thromboplastin time (aPTT), or thrombin time (TT), and since a normal PT is about 10-14 seconds, a normal ACT is about 70-130 seconds, and a normal TT is about 15-19 seconds, the measurements are performed every second. An aspect of the invention with respect to coagulation measurements, e.g. PT, ACT and TT, is to use the absorbance at one or more wavelengths or pattern recognition using absorbances at a plurality of wavelengths. Techniques of pattern recognition, combined with spectroscopy are known by those having skill in the art. An example where spectroscopy, combined with pattern recognition algorithms are used and that may be applied to the methods described herein, is provided in Zhang et. Al. (Mid-Infrared Spectroscopy for Coffee Variety Identification: Comparison of Pattern Recognition Methods", J. of Spectroscopy, Volume 2016, Article ID 7927286, the contents of which are incorporated herein by reference). As blood coagulates, the blood changes from various liquid varieties to various gel varieties, with corresponding changes in spectroscopic patterns, allowing one to use similar techniques as those used by Zhang et. al. to identify different variety of coffee beans. The specific blood coagulation time measured depends on the reagents included in the cartridge. For example, thromboplastin may be used for PT, celite or kaolin may be used for ACT, and thrombin may be used for TT.

Typically, blood coagulation time is measured using mechanical methods. For spectroscopic-based assays, citrated plasma is usually used in place of whole blood, because with whole blood, a much larger fraction of the incident EMR is scattered and absorbed by the blood cells, compared with the change in emerging EMR due to gelling of the plasma. However, separating out the plasma from the whole blood requires time and centrifugation equipment. It is well known that as plasma clots or coagulates, the absorbance at a single wavelength increases. By way of example, G. O. Gogstad et. al. (1986, "Turbidimetric Determination of Prothrombin Time by Clotting in a Centrifugal Analyzer" Clin. Chem. 32/10, 1857-1862; the contents of which are incorporated herein by reference), describe change in absorbance spectra of plasma during coagulation. However, measurement of coagulation time using whole blood instead of plasma is more representative of in vivo coagulation. Therefore, there is a need for spectroscopic measurement of the blood coagulation time employing whole blood. In order to improve the signal to noise ratio when whole blood is used with the devices as described herein, the depth of the optical chamber should be relatively small, for example about 100 micrometers. The use of absorbance, reflectance or transmittance at a single wavelength to generate a clotting reaction curve (for example as shown in FIG. 1 of Gogstad et. al. 1986, using absorbance), and the calculations used to compute clotting time, are considered to be within the scope of the present invention. Gogstad et. al. also provided examples of calculations use to compute clotting time that may be used according to the methods described herein.

As an example, the source of EMR may be a tungsten lamp. U.S. Pat. No. 6,651,015 (to Samsoondar, the contents of which are incorporated herein by reference) describes how spectrophotometric apparatus are calibrated for measuring properties of blood, using multi-wavelength analysis. With the use of a source of EMR like a tungsten lamp, which provides multiwavelength EMR (the tungsten lamp is polychromatic, whereas a laser is monochromatic), and the use of a linear PDA detector, the analyzer has the capacity to generate full absorbance spectra in milliseconds. Several spectra may be collected over milliseconds and the absorbances averaged to minimize noise. Mathematical smoothing techniques, which are covered extensively in the literature, may be used to minimize noise. Other mathematical techniques like the use of an order derivative of absorbance are also discussed in U.S. Pat. No. 6,651,015. Even though full absorbance spectra are obtained, selected portions of the absorbance spectra, a range of the absorbance spectra, or the full absorbance spectra, may be used in order to determine a concentration of one or more than one analyte of interest. Examples of absorbance spectra are provided in FIGS. 2-7 & 9 (see 39a-f and 39g respectively).

Cell Counting

Manual cell counting uses a microscope and a hemocytometer. A version of a prior art hemocytometer is provided in FIGS. 1A-1F, comprising a 4-mm (millimeter) thick glass slide with grid lines ground in the slide (one of two counting chambers is shown as C in FIG. 1A), and a cover glass. The grid C is divided into 9 major squares measuring 1×1 mm as shown in FIG. 10. Except for the central major square, each of the other 8 major squares are subdivided into 16 of 0.25×0.25 mm squares (see FIG. 1E). The central square consists of smaller spaced grid lines that can assist in determining the size of a cell (see FIG. 1F). With a coverglass in place over the counting chamber, two sample introduction ports may be used to introduce the cells (in a liquid suspension) to be counted (FIG. 1A). An enlarged cross-sectional view through the glass slide and cover glass shown in FIG. 1A along line B-B is presented in FIG. 1B. A view of detail D shown in FIG. 1B, showing a 0.1 mm gap between the top surface of the counting area and the bottom surface of the coverglass is provided in FIG. 1D. The volume of each 1×1 mm corner square is 100 nanoliters. After the cell suspension is loaded in the hemocytometer, the number of cells in the corner squares are counted using a microscope, and averaged.

U.S. Pat. No. 7,521,243 to Lindberg et al teaches a sample acquiring device for volumetric enumeration of white blood cells in a blood sample that includes a measurement cavity for receiving a blood sample. Lindberg's method includes acquiring a blood sample into an optical chamber holding a reagent comprising a hemolyzing agent and a staining agent for staining white blood cells. Some embodiments of cartridges, for example cartridges 10A-10C illustrated in FIGS. 10A-13E, comprise one or more reagents disposed in the post-optical chamber conduit, sufficiently far enough from the optical chamber and the one of a vent and a cartridge exit. Disposing the one or more reagents outside of the optical chamber, and specifically in the post-optical chamber conduit, enables the first sample interrogation to be performed on unaltered blood, and subsequently enables the second sample interrogation to be performed on altered blood, wherein altered blood is a mixture of blood and at least some of the one or more reagents.

Lindberg's system is incapable of jointly interrogating a blood sample free of reagents (sometimes referred to as an unaltered blood sample) and interrogating a mixture of blood sample and reagent(s) (sometimes referred to as an altered blood sample) in the same sample holder or cartridge.

Overview of Systems 30b, 30c, 30d, 30e, 30f and 30g as Non-Limiting Examples

Figure 3:
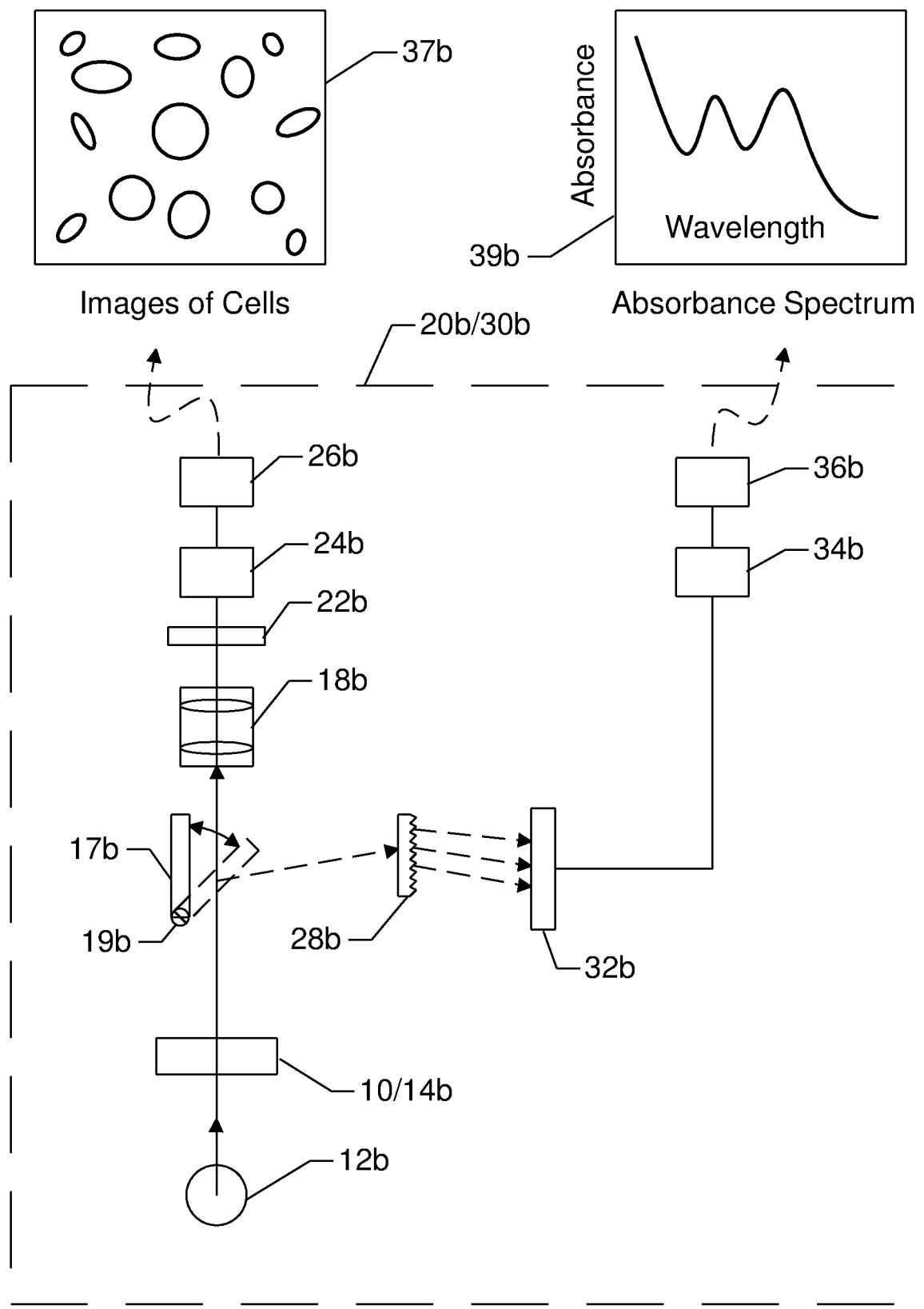
FIG. 3 is a block diagram of an example of a second embodiment of a system 30b (lower panel) for measuring one or more analyte quantities per unit volume of blood and one or more formed element quantities per unit volume of blood, in a blood sample. Output displays of the system (upper left and right panels) are provided as non-limiting examples.

A second embodiment of a system 30b for measuring one or more analyte quantities per unit volume of blood (i.e., the concentration of the analyte) using a spectroscopic technique, and one or more formed element quantities per unit volume of blood (i.e., a cell count) using an imaging technique is illustrated in FIG. 3. The most significant differences when compared with system 30a are:
1) instead of using a beam splitter 16a, a pivotal mirror 17b is used to direct EMR transmitted through the blood sample, to either detector 22b or detector 32b, depending on the position of the mirror;
2) system 30b comprises a magnification system 18b for projecting a real enlarged image on to the detector 22b; and
3) instead of a prism 28a, the EMR dispersing element is a transmission grating 28b.

The differences between the first set of emerging EMR and the second set of emerging EMR are: a) each set emerges from the sample at a different time, depending on the position of the pivotal mirror 17b; b) the first set of emerging EMR is reflected off the pivotal mirror 17b; and c) the second set of emerging EMR bypasses the pivotal mirror 17b. In some embodiments, the second set of emerging EMR may be reflected off the pivotal mirror and the first set of emerging EMR may bypass the pivotal mirror.

Figure 4:
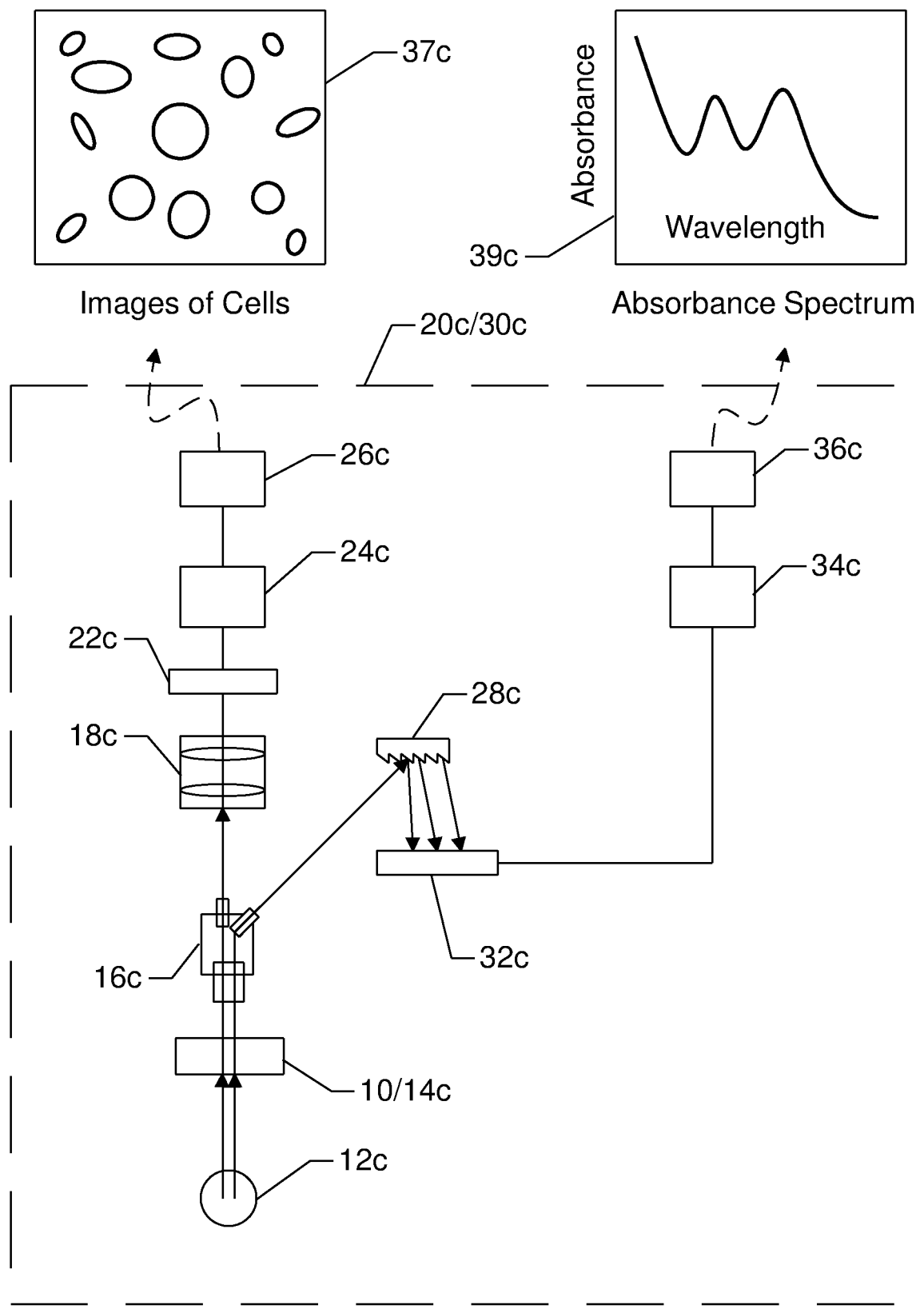
FIG. 4 is a block diagram of an example of a third embodiment of a system 30c (lower panel) for measuring one or more analyte quantities per unit volume of blood and one or more formed element quantities per unit volume of blood, in a blood sample. Output displays of the system (upper left and right panels) are provided as non-limiting examples.

A third embodiment of a system 30c is illustrated in FIG. 4. The most significant differences when compared with system 30b are:
1) a bifurcated optical fiber comprising one or more strands of optical fiber is used as a beam splitter; and
2) instead of a transmission grating 28b, the EMR dispersing element is a reflecting grating 28c.

The bifurcated optical fiber may be designed so that the magnitude of the first set of emerging EMR and the magnitude of the second set of emerging EMR are optimized to produce accurate measurements of the one or more cell counts and the one or more analyte concentrations.

A fourth embodiment of a system 30d is illustrated in FIG. 5. The most significance differences when compared to the first three embodiments 30a, 30b and 30c illustrated in FIGS. 2, 3 and 4 respectively are:
1) multiple sources of EMR (12' and 12d" are shown as examples, but others may be arranged in a circular manner, with respect to an axis represented by the direction of reflected and transmitted EMR) are used to interrogate the sample;
2) EMR reflected from the sample is projected on to the detector 22d (i.e., the second set of emerging EMR is reflected EMR);
3) EMR transmitted through the sample is projected on to the detector 32d (i.e., the first set of emerging EMR is transmitted EMR), via a reflecting grating 28d; and
4) no beam splitter or pivotal mirror is required.

A fifth embodiment of a system 30e is illustrated in FIG. 6. The most significance difference when compared to the fourth embodiment 30d illustrated in FIG. 5 is that EMR reflected from the sample is projected on to both detectors 22e, and 32e via a transmission grating 28e, wherein the general direction of first set of emerging EMR (reflected EMR) and the general direction of the second set of emerging EMR (also reflected EMR) define an angle less than 90 degrees.

Figure 7:
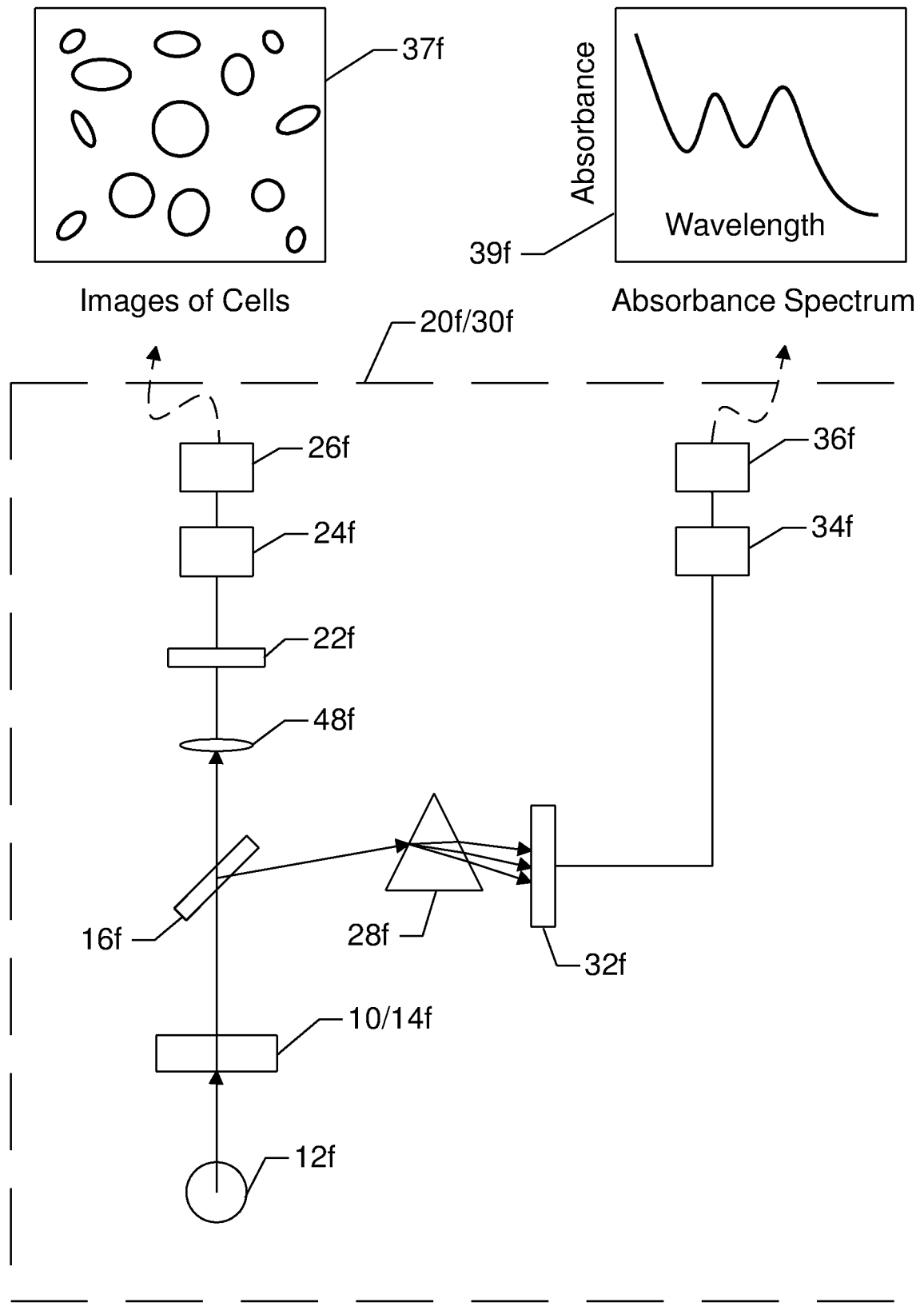
FIG. 7 is a block diagram of an example of a sixth embodiment of a system 30f (lower panel) for measuring one or more analyte quantities per unit volume of blood and one or more formed element quantities per unit volume of blood, in a blood sample. Output displays of the system (upper left and right panels) are provided as non-limiting examples.

A sixth embodiment of a system 30f is illustrated in FIG. 7. This embodiment is similar to the first embodiment 30a (see FIG. 2), with the following differences:
1) the beam splitter 16f is a plate comprising a partially silvered coating, or a plate comprising a dielectric coating;
2) no collimator is present (compared with a collimator 46a in system 30a);
3) a focusing system 48f is provided to focus the EMR transmitted through the sample on to the detector 22f;
4) two analog to digital converters 24f and 34f are shown; and 5) two processor systems 26f and 36f are shown.

In some embodiments, the beam splitter 16f is designed to transmit EMR at different wavelengths when compared to the wavelengths of the EMR that are reflected from the beam splitter 16f. For example, which is not to be considered limiting, methylene blue has a strong absorbance band centered at 660 nm, in the red region of the visible spectrum, and transmits wavelengths below 600 nm, appearing blue to the eye. On the other hand, hemoglobin appears red and can function as a red dye for tracking erythrocytes since erythrocytes are the only formed elements containing hemoglobin. As described in URL: ncbi.nlm.nih.gov/pmc/articles/PMC3005160/, hemoglobin has strong absorbance bands below 600 nm, and transmits wavelengths above 600 nm. Therefore in an embodiment of a system, for example, 30f (see FIG. 7, herein), the source of EMR 12f may be white light (and includes the visible spectrum: about 450-700 nm), a reagent, for example, methylene blue may be used to selectively stain the leukocytes, and the beam splitter 16f may be designed to transmit a range of red wavelengths and reflect a range of blue wavelengths. In this configuration, the red light will be absorbed by the stained leukocytes, and the blue light will be absorbed by the hemoglobin; leukocytes will appear as dark spots on the two-dimensional multi-channel detector 22f, and the blue light will be absorbed by the hemoglobin in erythrocytes, providing electrical signals on the one-dimensional multi-channel detector 32f, which could yield an absorbance spectrum like 39f having a wavelength range of about 450 nm to about 600 nm. This may also be applied to beam splitter 16a in system 30a (see FIG. 2).

A seventh embodiment of a system 30g is illustrated in FIG. 9. This embodiment is similar to the previously described embodiments, and the most significant difference is that two sources of EMR (12g' and 12g") are used, wherein source 12g' is on one side of the cartridge 10 and source 12g" is on the opposite side of the cartridge 10. Consequently, the first set of emerging EMR is mostly reflected EMR with mostly 12g' as the illuminating source, and the second set of emerging EMR is mostly transmitted EMR with mostly 12g" as the illuminating source.

Simplified Perspective View of System 30a as a Non-Limiting Example

An example of a system 30a comprising an analyzer 20a and a cartridge 10A is illustrated in FIGS. 8A-8C, in a simplified form. Shown in FIG. 8A is perspective view of a first embodiment of a system 30a for measuring one or more analyte quantities per unit volume of blood and one or more formed element quantities per unit volume of blood, in a blood sample, showing the analyzer 20a, with the analyzer receptor 14a in an open position, and also showing the cartridge 10A outside the analyzer 20a. Shown in FIG. 8B is perspective view of a first embodiment of a system 30a showing the cartridge 10A engaged with the analyzer receptor 14a, with the analyzer receptor 14a in an open position. Shown in FIG. 8C is perspective view of a first embodiment showing the cartridge 10A engaged with the analyzer receptor 14a, with the analyzer receptor 14a in a closed position. Although cartridge 10A is used for illustration, several embodiments of cartridges may be used. Detail of four examples of cartridges are provided below, which should not be considered limiting in any way. The differences between the cartridges are highlighted.

Overview of Cartridges 10A, 10B, 10C and 10D as Non-Limiting Examples

As mentioned previously, uppercase letters ("A", "B", "C" and "D") are sometimes used to refer to cartridge features, whereas the lowercase letters ("a", "b" etc.) are sometimes are used to refer to system features. Table 2 (above) provides a list of the reference numerals used, and a description of the corresponding structural features.

Figure 10A:
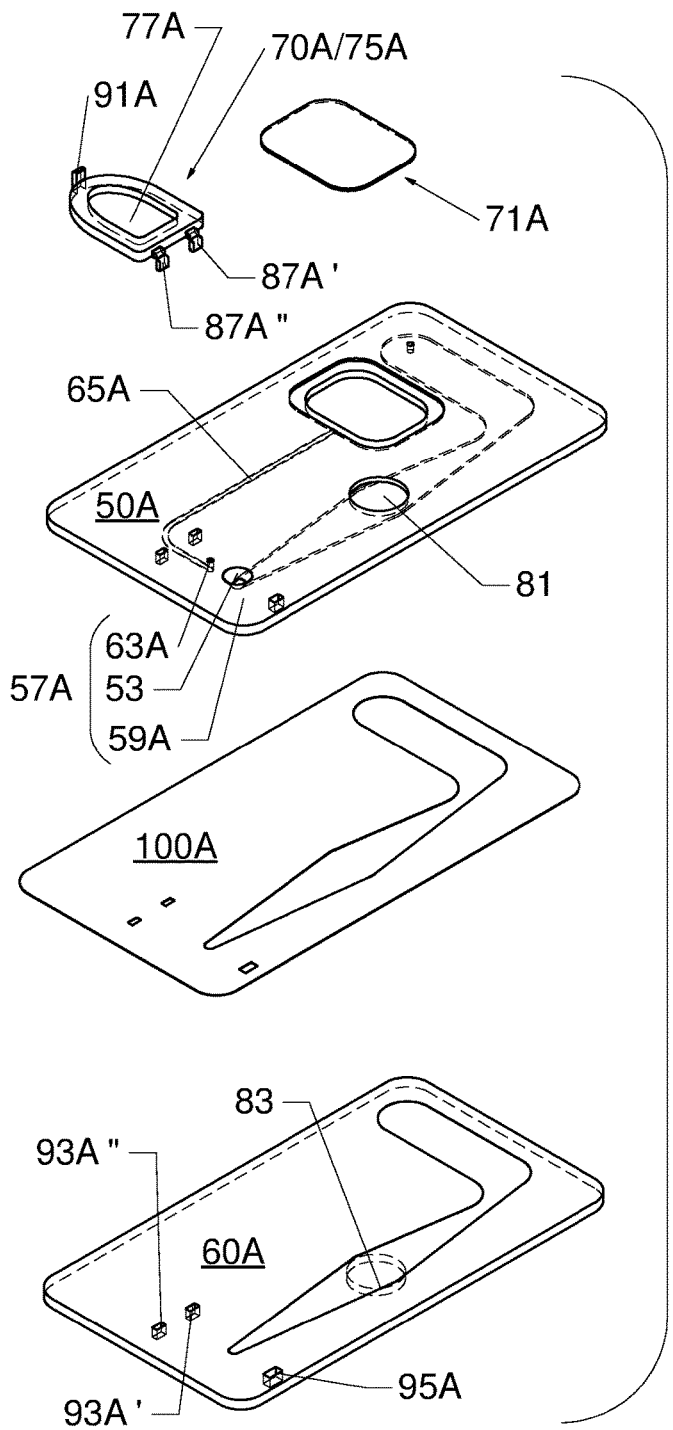
FIG. 10A is an exploded top perspective view of a cartridge 10A for measuring at least one property of blood, according to a first embodiment of the cartridge.

Cartridge 10A (see FIGS. 10A-10J) is a first embodiment of a cartridge used with a system for measuring one or more analyte quantities per unit volume of blood and one or more formed element quantities per unit volume of blood, in a blood sample. However, this and the other embodiments of cartridges provided in this application may also be used for measuring one or more properties of a blood sample, for example, but not limited to, the concentration of bilirubin or hemoglobin, and a leukocyte count. The cartridge comprises a cartridge body having an upper surface and a lower surface. Shown in FIG. 10A is an exploded top perspective view of cartridge 10A. In this example, the upper surface is the top surface of a first housing member 50A, and the lower surface is the bottom surface of a second housing member 60A. In FIG. 10A, details of the upper surface are shown but the bottom surface is not shown. The bottom surface is a plain surface having an optical window 83 (see FIG. 10K). The housing members 50A and 60A are held together by a double-sided sticky gasket 100A. However, this is just one non-limiting example illustrating how the cartridge (comprising a cartridge body having an upper surface and a lower surface) may be manufactured and assembled. For example, the cartridge may comprise a plurality of members and gaskets, the cartridge may be 3-D printed, or the cartridge may be 3-D printed in combination with a plurality of members and gaskets.

Figure 10B:
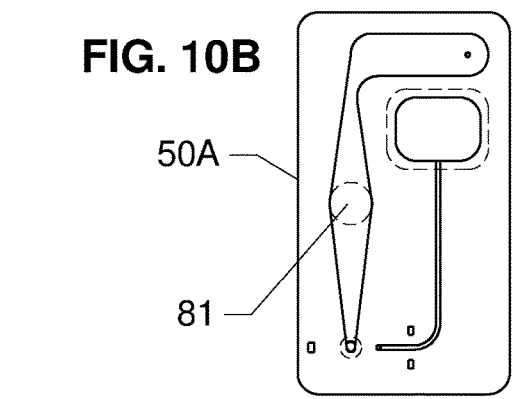
FIG. 10B is a bottom view of the first housing member 50A of the cartridge shown in FIG. 10A.
Figure 10C:
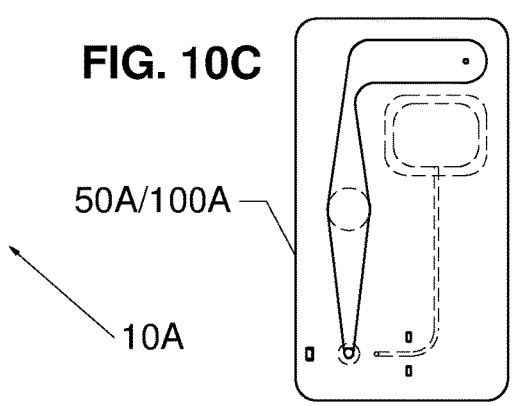
FIG. 10C is the bottom view of the first housing member 50A of the cartridge shown in FIG. 10B, overlaid by and in alignment with a gasket 100A shown in FIG. 10A.
Figure 10D:
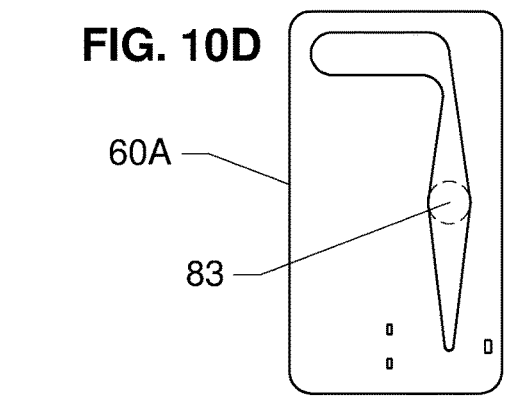
FIG. 10D is a top view of the second housing member 60A of the cartridge shown in FIG. 10A.
Figure 10E:
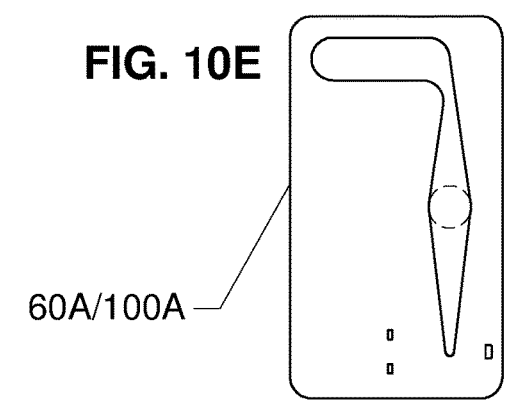
FIG. 10E is the top view of the second housing member 60A shown in FIG. 10D, overlaid by and in alignment with the gasket 100A shown in FIG. 10A.

Shown in FIG. 10B is a bottom view of the first housing member 50A of the cartridge shown in FIG. 10A, and shown in FIG. 10C is the bottom view of the first housing member 50A of the cartridge shown in FIG. 10B overlaid by and in alignment with the gasket 100A shown in FIG. 10A. Shown in FIG. 10D is a top view of the second housing member 60A of the cartridge shown in FIG. 10A, and shown in FIG. 10E is the top view of the second housing member 60A shown in FIG. 10D overlaid by and in alignment with the gasket 100A shown in FIG. 10A. The cutouts in the gasket 100A are not labeled because FIGS. 10B-10E illustrate how the gasket cutouts are aligned with the first and second housing members 50A and 60A respectively, and a person having ordinary skill in the art should appreciate that the gasket cutouts could be designed differently without affecting the functionality of the cartridge in any significant way.

Shown in FIG. 10F is a perspective view of the cartridge 10A shown in FIG. 10A, in a fully open position, i.e., the cap 70A is in an open position. Shown in FIG. 10G is a perspective view of the cartridge 10A shown in FIG. 10A, in a fully closed position, i.e., the cap 70A is in a closed position. Shown in FIG. 10H is top view of the cartridge 10A shown in FIG. 10G, in the fully closed position. Shown in FIG. 10J is an enlarged cross-sectional view through the cartridge 10A shown in FIG. 10H along line J-J. Shown in FIG. 10K is an enlarged cross-sectional view through the cartridge 10A shown in FIG. 10H along line K-K.

The sample inlet portion 57A comprises some elements of the cartridge that interact with cap 70A, for example a top portion 53 of a sample storage well 51 for receiving the blood sample, a flat surface 59A, and an air bladder communication port 63A (see FIGS. 10A, 10F, 10J and 10K). The sample inlet portion may also be described as comprising a sample storage well 51, a flat surface 59A, and an air bladder communication port 63A. The sample storage well 51 also comprises a bottom portion (or bottom opening) 55 for releasing at least a portion of the blood sample into an optical chamber inlet conduit or pre-optical chamber conduit 97A (see FIGS. 10H-10K). Depending on the relative hydrophilicity of the sample storage well 51 and the relative hydrophobicity of the pre-optical chamber conduit 97A, the blood may stop at the bottom opening 55 of the sample storage well 51.

In some embodiments, a hydrophobic insert (for example, 225C shown in FIGS. 12F, 12H and 12J) disposed close to the junction of the bottom opening 55 of the sample storage well 51 and the optical chamber inlet conduit 97A for providing means for minimizing, mitigating, or modifying blood flow out of the sample storage well 51. In other embodiments, an enlarged cavity may replace the hydrophobic insert, and the enlarged cavity may function as a capillary break. In other embodiments, the sample storage well may be in the form of an insert made from hydrophilic (i.e. wettable) material, and the optical chamber inlet conduit 97A may be made from less hydrophilic material (i.e., less wettable). The use of a hydrophobic insert like 225C allows the rest of the cartridge to be manufactured from a less hydrophobic or hydrophilic material.

In addition to an enlarged cavity, a hydrophobic insert and a sample storage well insert, other structural features that provide means for minimizing, mitigating, or modifying blood flow out of the sample storage well except when either positive pressure is applied to the surface of the blood sample in the sample storage well (e.g. in cartridges 10A, 10B and 10D), or negative pressure is applied to the leading edge of the blood sample (e.g., in cartridges 10C). The leading edge of the blood sample refers to the front end of the sample, flowing out from the sample storage well 51, which is the first portion of the blood sample to enter the optical chamber 13. Some examples of structural features include: a sample storage well insert having internal walls more wettable than the optical chamber inlet conduit (an example of a sample storage well insert is illustrated in details in U.S. Pat. Appl'n Pub. No. US 2019/0224667); a sample storage well having internal walls more wettable than the optical chamber inlet conduit; an optical chamber inlet conduit less wettable than the internal walls of the sample storage well; and any combination thereof. Also, the stringency of the requirement to mitigate blood flow from the sample storage well into the optical chamber inlet conduit depends on the property of the blood measured.

Cartridge 10A employs the use of positive pressure that may be applied to the surface of the blood sample in the sample storage well 51. This is accomplished by through participation of the following:

1) an air bladder 67A in the cartridge for generating positive pressure by squeezing a flexible member 71A (FIGS. 10F and 10G) of the air bladder 67A, and for generating negative pressure by releasing the squeezed flexible member 71A;
2) a means in an analyzer that is operating in conjunction with the cartridge when the cartridge is inserted within a receptor of the analyzer, the means for squeezing the air bladder via flexible member 71A (not shown);
3) an air bladder communication port 63A of a sample inlet portion 57A (FIGS. 10A and 10F),
4) an air bladder duct 65A (FIGS. 10A and 10H) for providing fluid connection between an air bladder 67A and an air bladder communication port 63A;
5) a vent 85A for releasing pressure in the optical chamber (FIGS. 10F-10H);
6) a flat surface 59A located on the upper surface of the cartridge body, the flat surface 59A of the cartridge body surrounding the top portion of the sample storage well 53 and the air bladder communication port 63A (e.g. as shown in FIG. 10J), and
7) a cap flat surface 76A located on the underside 75A of the cap 70A (see FIG. 10A).

The cartridge is adjustable between an unsealed configuration (see FIG. 10F) and a sealed configuration (see FIG. 10G). In the unsealed configuration the sample storage well is configured to receive the blood sample; in the sealed configuration a portion of the flat surface 59A of the cartridge body mates with the cap flat surface 76A to form a closed air passage operatively connecting the air bladder communication port 63A to the sample storage well 51 so that either positive pressure or negative pressure is transferable to the sample storage well. The closed air passage may be facilitated by a groove set into the upper surface of the cartridge body, a recess 77A set into the underside 75A of the cap 70A, or a combination thereof. In this embodiment, a cap recess 77A is shown in FIGS. 10A, 10F, 10J and 10K, illustrating formation of the closed air passage.

Squeezing the air bladder 67A via the flexible member 71A creates positive pressure and releasing the flexible member 71A creates negative pressure at the surface of blood in the sample storage well 51. Therefore, the air bladder provides means for both pushing the blood towards the vent 85A and pull the blood away from the vent 85A. This is an example of a positive to negative pressure means for creating blood flow. A negative to positive pressure means for creating blood flow is provided through cartridge 10C (see FIGS. 12A-12J).

When blood from, for example a pin prick of blood on a patient's skin (i.e., capillary blood) or blood in a syringe (i.e., venous or arterial blood), is deposited in the sample storage well 51, the blood may stay in the sample storage well 51, depending on the cartridge design, the material used to build the cartridge, and the requirement of means for minimizing, mitigating, or modifying blood flow out of the sample storage well 51. After the cap 70A is closed, i.e., adjusting the cartridge from an unsealed to a sealed configuration, the cartridge is placed in a receptor like 14a illustrated in FIGS. 8A-8C, and the rest of the process is fully automated. The next step in this example is to use pressurized air from air bladder 67A to fill the optical chamber 13 (see FIGS. 10H & 10K) by pushing at least some of the blood out of the sample storage well 51. The activation of the air bladder may be programmed so that the leading edge of the blood stops anywhere in the optical chamber exit conduit, i.e., between the optical chamber 13 and the vent 85A.

Using a system configuration 30a as an example (see FIG. 2), sample interrogation takes place after the optical chamber 13 is filled with blood. The EMR transmitted through the blood in optical chamber 13 is split using beam splitter 16a. EMR reflected from the beam splitter 16a (i.e., a first set of emerging EMR) is projected on to the one-dimensional multi-channel detector 32a via an EMR dispersing element 28a, and EMR transmitted through the beam splitter 16a (i.e., a second set of emerging EMR) is projected on to the two-dimensional multi-channel detector 22a. Signals from the two detectors 22a and 32a are digitized using the analog to digital converter 26a, and the processor 26a processes digital data (or digital information). The processed information may be displayed as images of cells (37a) and an absorbance spectrum (39a). The displays may come from unaltered blood, but in some embodiments, the cartridge 10a may contain one or more dry reagents disposed in the optical chamber inlet conduit 97A or the optical chamber 13, where the blood dissolves the one or more dry reagents.

U.S. Pat. No. 7,521,243 to Lindberg et al teaches a sample acquiring device for volumetric enumeration of white blood cells in a blood sample, the device having an optical chamber containing several dry reagents, including RBC lysing reagents and WBC staining reagents. Lindberg does not teach disposing a reagent in the optical chamber exit conduit (or post-optical chamber conduit). Moreover, Lindberg's sample acquiring device depends on capillary action for blood flow, therefore blood can only flow in one direction and that direction is into the optical chamber. This is to be contrasted with an embodiment of the present invention that may comprise one or more reagents in the space between the optical chamber and one of a vent and a cartridge exit.

For example, in some modifications of cartridge 10A, the one or more reagents is disposed in the post-optical chamber conduit 99A. In this embodiment, the system may be programmed so that blood flows into the optical chamber exit conduit 99A whereby the blood is able to reach and dissolve at least a portion of the one or more reagents. The one or more reagents is disposed in the post-optical chamber conduit, sufficiently far enough from the optical chamber and the one of a vent and a cartridge exit, enabling the first sample interrogation on unaltered blood. Therefore, while the unaltered blood is being interrogated by EMR (i.e., a first sample interrogation), blood in the optical chamber exit duct 99A is reacting with at least a portion of the one or more reagents. After a predetermined time, after the first sample interrogation, the mixture of blood and one or more reagents (i.e., altered blood) is pulled back into the optical chamber for a second sample interrogation, by releasing the squeezed air bladder 67A. Therefore, the first sample interrogation uses unaltered blood and the second sample interrogation uses altered blood (i.e., a mixture of blood and some of the one or more reagents). As an example, if the reagents comprise hemolyzing reagents and leukocyte specific stains, the first sample interrogation could provide means for measuring hemoglobin concentration by using the one-dimensional multi-channel detector 32b as well as means for counting erythrocytes using the two-dimensional multi-channel detector 22*b*, and the second sample interrogation could provide means for counting leukocytes, also using the two-dimensional multi-channel detector 22*b* (see FIG. 3).

It is known that an average PCV or hematocrit is about 45%, and it is also known that erythrocytes account for most of the formed elements of blood (see Table 1). Therefore, the space between erythrocytes, which comprises mostly plasma, is about 55% of the area of the optical chamber, assuming cells are distributed approximately as a monolayer. A shallow (~50 μm) optical chamber is more likely to provide a monolayer of erythrocytes. It is also known that the number of leukocytes in a blood sample is about 0.1% the number of erythrocytes, therefore a deeper (~200 μm) optical chamber could provide a monolayer of leukocytes because of the relatively low cell count. Manual counting of erythrocytes using a hemocytometer illustrated in FIGS. 1A-1F and a microscope usually requires about 200× dilution of the blood sample, to provide an adequate number of cells for an accurate cell count. The dilution is required because the manual process is very tedious and error prone and a 200*x* dilution provides sufficient erythrocytes for counting.

During the first sample interrogation in the present invention, a magnified image of a relatively small area of the optical chamber containing undiluted blood provides sufficient erythrocytes and sufficient spaces between erythrocytes for accurate erythrocyte counting and may be an alternative to diluting the blood sample. If the shallow optical chamber is used, in order to provide erythrocyte counting, then it may be preferred to interrogate a larger area of the same optical chamber to provide leukocyte counting. As examples, magnification may be provided by magnification systems 18*b*, 18*c*, 18*d*, 18*e* and 18*g* are shown in FIGS. 3, 4, 5, 6 and 9 respectively. Magnification and/or high resolution two-dimensional multi-channel detectors may facilitate erythrocyte counting without having to dilute the blood sample. The size of an erythrocyte is 6-8 μm (see Table 1), therefore a preferred pixel pitch in a two-dimensional multi-channel detector for counting erythrocytes is less than 4 μm, and a preferred pixel pitch for counting erythrocytes and leukocytes is 1-10 μm.

The number of leukocytes is about 0.1% the number of erythrocytes, therefore, in order to count leukocytes it is preferred to use an undiluted blood sample. U.S. Pat. No. 7,521,243 to Lindberg describes a method to selectively lyse the erythrocytes (the term hemolyze may be used), leaving the leukocytes intact. Non-limiting examples of hemolyzing reagents include: a quaternary ammonium salt, a saponin, a bile acid such as deoxycholate, a digitoxin, a snake venom, a glucopyranoside, or a non-ionic detergent of type Triton (see U.S. Pat. No. 7,521,243 to Lindberg). For counting leukocytes, it may also be preferred to interrogate a larger area of the optical chamber and if the area of the optical chamber is similar to the area of the two-dimensional multi-channel detector, no magnification may be required. Another reagent may be a staining reagent. Staining reagents may selectively stain the nuclei of leukocytes. Without being limited in anyway, staining reagents may be selected from eosin, methylene blue, methylene green, azure, thionin, toluidine blue, or any combination thereof.

An aspect of the present invention is therefore to dispose the one or more reagents in the post-optical chamber conduit of the cartridge.

Shown in FIG. 11A is an exploded top perspective view of cartridge 10B that may be used instead of cartridge 10A. The major differences in cartridge 10B compared with cartridge 10A are as follows:
1) the cap 70B is hingedly attached to the cartridge body via a pivot 89B in the cap 70B and holes 88B' and 88B" in the first and second housing members 50B and 60B respectively, for receiving the pivot 89B, and
2) in addition to recess 77B that is used to facilitate formation of a closed air passage discussed previously, there is a second recess or groove 94B disposed at the underside 75B and at the sweeping portion of cap 70B, for storing excess sample (see FIG. 11C).

In some embodiments, a groove may be set in the flat surface 59B of inlet portion 57B; by adding excess blood sample where the excess bulges above the top opening 53 of the sample storage well 51, the excess blood may be swept away by a sweeping edge of the cap, and a fixed volume of blood may be retained in the sample storage well 51. The recess 94B or a groove in the flat surface 59B could receive and store the excess blood and avoid contaminating the analyzer with blood. For some measurements, a predetermined ratio of blood volume to quantity of one or more reagents is required for more accurate measurement; means for minimizing, mitigating, or modifying blood flow out of the sample storage well 51 were discussed previously.

Shown in FIG. 11B is a bottom view of the first housing member 50B of the cartridge shown in FIG. 11A. Shown in FIG. 11C is a perspective top view of the cap 70B shown in FIG. 11A showing the tops side 73B. Shown in FIG. 11D is a perspective bottom view of the cap 70B shown in FIG. 11A showing the underside 75B. Shown in FIG. 11E is a perspective top view of the cartridge 10B shown in FIG. 11A, in a fully open position (or unsealed configuration). Shown in FIG. 11F is a perspective top view of the cartridge 10B shown in FIG. 11A, in a fully closed position (or sealed configuration). Shown in FIG. 11G is top view of the cartridge 10B shown in FIG. 11E. Shown in FIG. 11H is top view of the cartridge 10B shown in FIG. 11F. Shown in FIG. 11J is an enlarged cross-sectional view through the cartridge 10B shown in FIG. 11G along line J-J. Shown in FIG. 11K is an enlarged cross-sectional view through the cartridge 10B shown in FIG. 11H along line K-K, showing the closed air passage connecting air bladder communication port 63B to sample well 51 via cap recess 77B.

Another major difference in cartridge 10B is: 3) a cap latch 91B and a recess 92B in the cap latch 91B are used for engaging cap 70B, when the cartridge is adjusted to a sealed configuration (see FIGS. 11G-11K). In some embodiments of caps 70A and 70B, gaskets are disposed at the cap flat surfaces 76A and 76B respectively, for creating better seals between caps and cartridges in their sealed configurations. Alternatively, the gaskets may be disposed at the flat surfaces 59A and 59B of the inlet portions 57A and 57B respectively of cartridges 10A and 10B respectively.

Yet another major difference in cartridge 10B is: 4) a conductivity sensor 200 comprising a pair of conductivity electrodes (also referred to as probes), for performing several functions, e.g., controlling air bladder activation means (e.g. a stepper motor in the analyzer, having a linear actuator that presses against flexible member 71B of air bladder 67B); an analyzer pump that is discussed below; and measuring hematocrit also discussed below.

Referring to FIGS. 11A, 11B, 11G and 11H, ends (pins) 203' and 203" of sensor 200 projecting out of cartridge 10B facilitate electrical communication with a relay, when the cartridge is properly inserted in the analyzer receptor. In use, a voltage is applied over ends 201' and 201" (see FIG. 11B) of conductivity sensor 200 via the relay in the associated analyzer. The ends 201' and 201" are exposed in optical chamber exit conduit 99B, and can make contact with blood when the leading edge of the blood reaches the ends 201' and 201". The ends 201' and 201" function as an open switch when the conduit is not occupied by blood, and function as a closed switch when blood bridges the gap between the ends 201' and 201". When the switch is closed, a current travels to the relay in the analyzer, and the relay may control, for example, a stepper motor. The relay is used to apply a voltage across sensor ends 201' and 201", and may be used to activate/deactivate an air bladder stepper motor. Some embodiments of a cartridge may comprise a conductivity sensor like 200, installed anywhere in the cartridge where the conductivity sensor can make contact with unaltered blood, and the sensor may be used for measuring hematocrit (see U.S. Pat. No. 5,821,399 to Zelin and U.S. Pat. No. 5,112,455 to Cozzette). The electrical conductivity of blood is inversely proportional to the hematocrit because the erythrocyte membranes act as insulators.

A conductivity sensor like 200 shown in cartridge 10B is not provided in cartridge 10A but it is optional in cartridge 10A. In embodiment 10A, activation of the air bladder of the cartridge may be controlled by preprogramming the activation based on pre-determined expected travel of the leading edge of the blood. However, a sensor 200 may be used to provide more precise movement of the leading edge of the sample.

Common to cartridges 10A and 10B is the use of respective air bladders 67A and 67B for providing positive pressure by squeezing the air bladder, and for providing negative pressure by releasing the squeezed air bladder (negative pressure can only be created after the air bladder is squeezed and then released). Therefore, the use of the air bladder may be described as a positive to negative pressure means for creating a blood flow in a direction towards the vent and creating a blood flow in a direction away from the vent (85A & 85B).

Cartridge 10C is described next, where a negative to positive pressure means is described. Positive to negative pressure means and negative to positive pressure means were discussed previously, and these are aspects of the present invention.

The most significant difference between cartridge 10C and cartridges 10A and 10B is the use of a pump in an associated analyzer, for providing a negative to positive pressure means. The negative pressure means may be used for pulling the leading edge of the blood sample from the sample storage well 51 to fill the optical chamber 13 (for performing a first sample interrogation on unaltered blood) and subsequently, a positive pressure used to push against the leading edge of the blood. In embodiments having one or more reagents disposed in the optical chamber exit conduit 99C, the positive pressure may be used to fill the optical chamber 13 with altered blood, for conducting a second sample interrogation. First and second sample interrogations were discussed previously.

Since the associated analyzer comprises a pump, an air bladder like 67A and a vent like 85A shown for cartridge 10A are not required for cartridge 10C.

Illustrated in FIG. 12A is an exploded top perspective view of cartridge 10C for measuring at least one property of a sample, showing a sealing member 211C installed in a cartridge exit duct 217C (see FIGS. 12F & 12G), for frictionally engaging an outer surface of a pump hollow needle. The pump hollow needle comprises a first end operatively connected to the analyzer pump, a second end distal to the first end and operatively connected to the first end, and the outer surface of the pump hollow needle. Illustrated in FIG. 12B is a bottom view of the first housing member 50C of the cartridge 10C shown in FIG. 12A. Illustrated in FIG. 12C is a top view of the second housing member 60C of the cartridge shown in FIG. 12A. Illustrated in FIG. 12D is a perspective view of the cartridge 10C in a fully open position and illustrated in FIG. 12E is a perspective view of the cartridge 10C in a fully closed position, showing a cap breathable plug 223C (an example of a cap vent). It should be noted that when cartridge 10C is in a fully closed position, it is not in a sealed configuration as cartridge 10A shown in FIG. 10G, since cap vent 223C exposes the blood in the sample storage well 51 to atmospheric pressure. A person having ordinary skill in the art should appreciate that other means may be used for subjecting the blood in the sample storage well 51 to atmospheric pressure, for example without any limitations, a hole in the cap, or a leaky seal between the cartridge body upper surface and the cap when the cap is closed. For simplicity, the means for subjecting the blood in the sample storage well 51 to atmospheric pressure when the cap is closed, may be described as a cap vent. Illustrated in FIG. 12F is top view of the cartridge 10C shown in FIG. 12E, illustrating a flow path from the cap vent 223C to the cartridge exit 219C. Cartridge exit 219C is a portion of cartridge exit duct 217C of cartridge 10C, for establishing operative communication with an analyzer pump. Illustrated in FIG. 12G is an enlarged cross-sectional view through the cartridge 10C shown in FIG. 12F along line G-G. Illustrated in FIG. 12H is an enlarged cross-sectional view through the cartridge 10C shown in FIG. 12F along line H-H. Illustrated in FIG. 12J is an enlarged cross-sectional view through the cartridge 10C shown in FIG. 12F along line J-J.

Cartridge 10C also comprises the following features, which are not shown for cartridges 10A & 10B:
1) a sample storage well boss 221C for increasing the sample storage well storage capacity (see FIGS. 12D & 12J); and
2) a hydrophobic insert 225*c* (see FIGS. 12F, 12H & 12J) disposed close to the junction of the bottom opening 55 of the sample storage well 51 and the optical chamber inlet conduit 97C, for providing means for minimizing, mitigating, or modifying blood flow out of the sample storage well 51.

Recesses 227C and 229C in first housing member 50C and the second housing member 60C respectively, are shown in FIGS. 12B & 12C for installing the hydrophobic insert 225C. Hydrophobic insert 225C is an example of means for minimizing, mitigating, or modifying blood flow out of the sample storage well 51. In other embodiments, an enlarged cavity may replace the hydrophobic insert, and the enlarged cavity may function as a capillary break. In yet other embodiments, the sample storage well may be in the form of an insert made from hydrophilic (i.e. wettable) material, and the optical chamber inlet conduit 97A may be made from less hydrophilic material (i.e., less wettable). An example of a sample storage well insert is illustrated in U.S. Pat. Appl'n Pub. No. US 2019/0224667.

In addition to an enlarged cavity, a hydrophobic insert, and a sample storage well insert, other structural features may provide means for minimizing blood flow out of the sample storage well except when either positive pressure or negative pressure is applied to the blood sample. Some of these features include: a sample storage well insert having internal walls more wettable than the optical chamber inlet conduit; a sample storage well having internal walls more wettable than the optical chamber inlet conduit; an optical chamber inlet conduit less wettable than the internal walls of the sample storage well; and any combination thereof. As mentioned previously, the stringency of the requirement to mitigate blood flow from the sample storage well into the optical chamber inlet conduit 97C depends on the property of the blood measured.

Cartridge 10D is similar to cartridge 10A, except that an analyzer pump is required, instead of an air bladder, to provide positive pressure to the closed air passage operatively connecting the analyzer pump communication port 63D to the sample storage well 51 so that either positive pressure or negative pressure is transferable to the sample storage well (see FIG. 13E). Therefore, the use of the analyzer pump may be described as a positive to negative pressure means for creating a blood flow in a direction towards the vent 85D and creating a blood flow in a direction away from the vent 85D. A reversed mechanism was mentioned previously for cartridge 10C (see FIGS. 12A-12J), in that cartridge 10C provides a negative to positive pressure means, i.e., negative pressure is provided first, and if the optical chamber exit contains one or more reagents, positive pressure may be used to push a mixture of blood and reagent(s) back into the optical chamber.

Figure 13A:
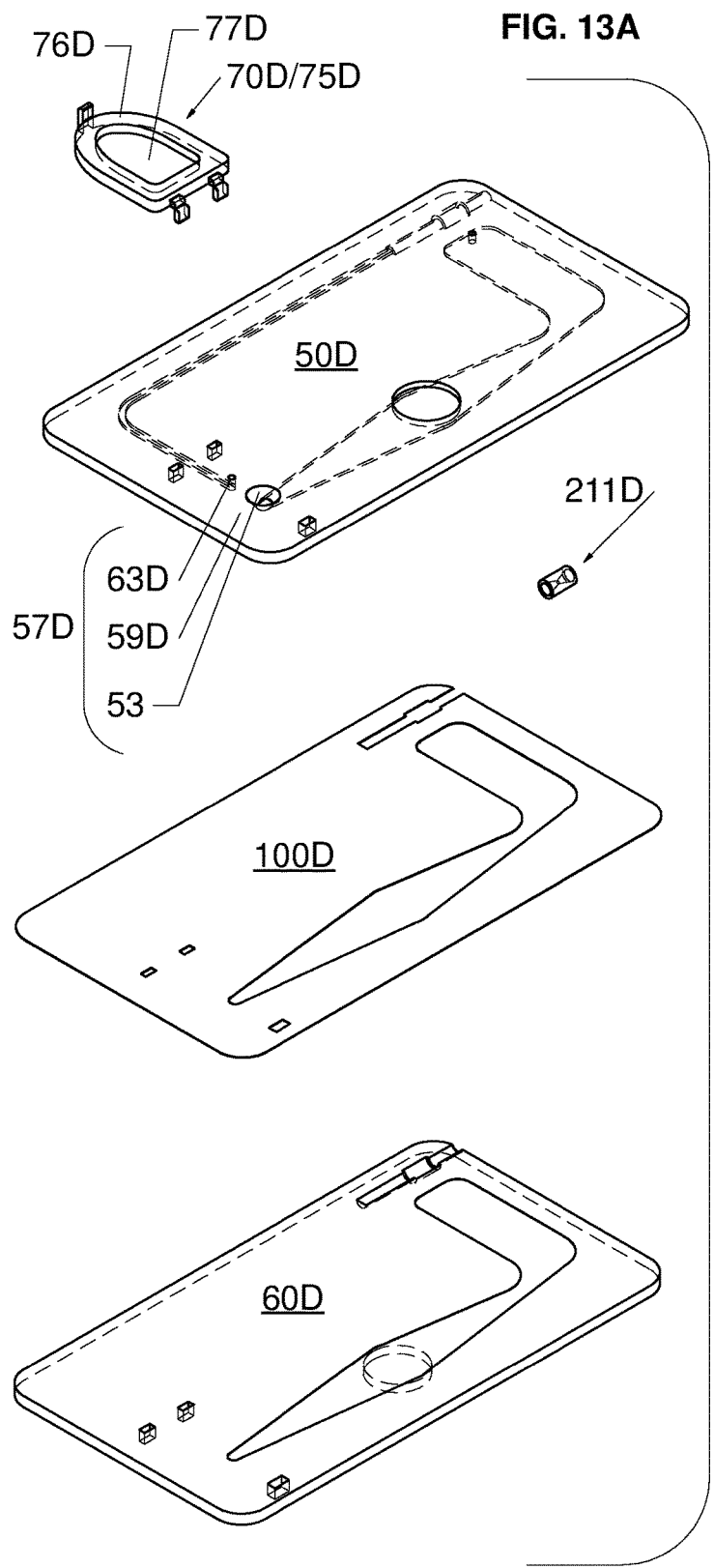
FIG. 13A is an exploded top perspective view of a cartridge 10D for measuring at least one property of blood, according to a fourth embodiment of a cartridge.
Figure 13B:
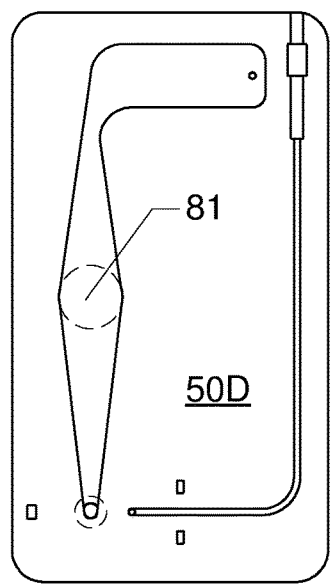
FIG. 13B is a bottom view of the first housing member 50D of the cartridge shown in FIG. 13A.
Figure 13C:
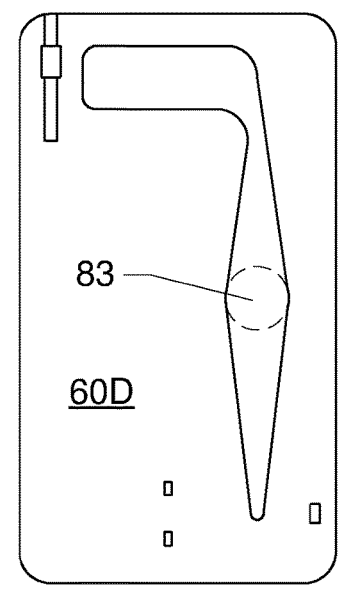
FIG. 13C is a top view of the second housing member 60D of the cartridge shown in FIG. 13A.

Shown in FIG. 13A is an exploded top perspective view of a cartridge 10D for measuring at least one property of blood, showing a sealing member 211D installed in cartridge air inlet duct 217D (see FIGS. 13D & 13F), for frictionally engaging an outer surface of a pump hollow needle. Like the analyzer pump discussed regarding cartridge 10C, the pump hollow needle comprises a first end operatively connected to the analyzer pump, a second end distal to the first end and operatively connected to the first end, and the outer surface of the pump hollow needle. Shown in FIG. 13B is a bottom view of the first housing member 50D of the cartridge shown in FIG. 13A. Shown in FIG. 13C is a top view of the second housing member 60D of the cartridge shown in FIG. 13A. Shown in FIG. 13D is top view of the cartridge 10D shown in FIG. 13A. Shown in FIG. 13E is an enlarged cross-sectional view through the cartridge 10D shown in FIG. 13D along line E-E, and shown in FIG. 13F is an enlarged cross-sectional view through the cartridge 10D shown in FIG. 13D along line F-F. For clarity, 217D is referred to as a cartridge air inlet duct and 219D is referred to as a cartridge air inlet, in order to differentiate 217D and 219D from similar structures 217C and 219C found in cartridge 10C; 217C is referred to as a cartridge exit duct and 219C is referred to as a cartridge exit. Moreover, it should be noted that cartridge 10D has a vent 85D (see FIG. 13D) similar to vent 85A in cartridge 10A (see FIG. 10H), whereas cartridge 10C does not have a vent like 85A and 85D; instead, cartridge 10C has a cap vent 223C (see FIG. 12F).

Overview of Cartridge 10E as a Non-Limiting Example

Figure 14A:
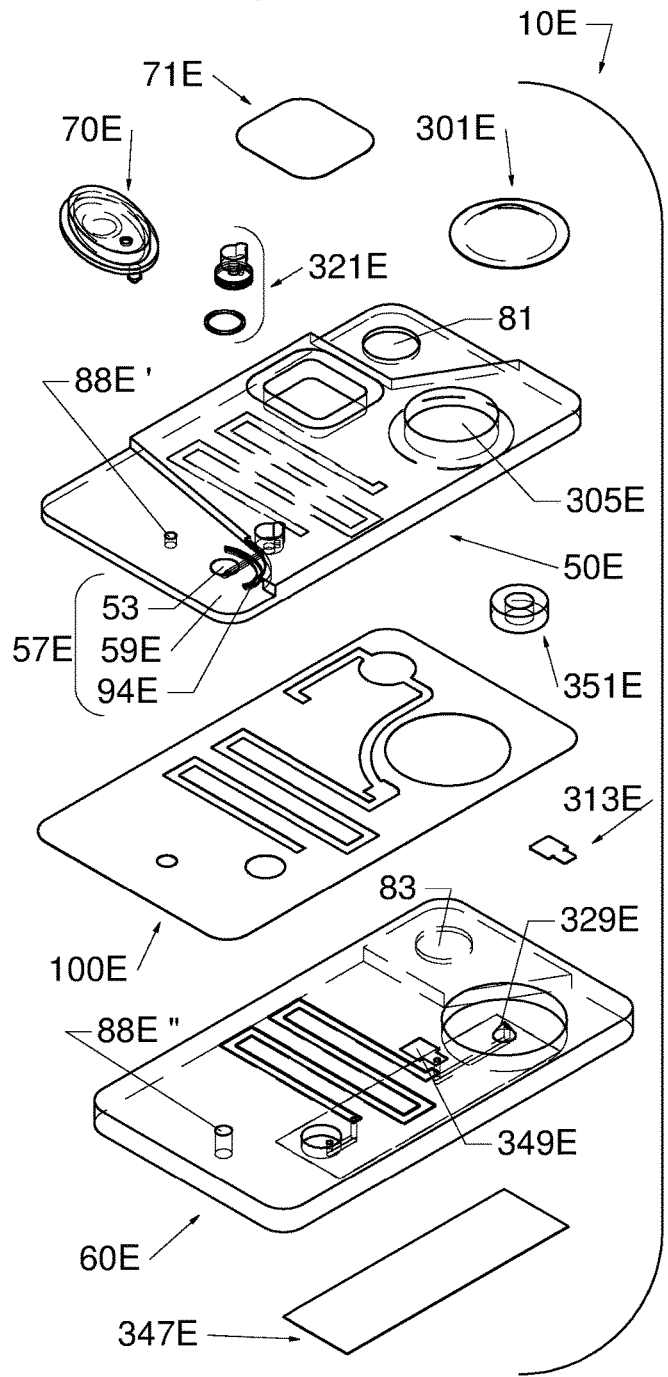
FIG. 14A is an exploded top perspective view of a cartridge 10E for measuring at least one property of blood, according to a fifth embodiment of the cartridge.

Cartridge 10E (see FIGS. 14A-14Y) is a fifth embodiment of a cartridge that may be used within a system for measuring one or more analyte quantities per unit volume of blood and one or more formed element quantities per unit volume of blood, in a blood sample. Cartridge 10E may also be used for measuring one or more properties of a blood sample, for example, but not limited to, the concentration of bilirubin or hemoglobin, and a leukocyte count. Cartridge 10E comprises a cartridge body having an upper surface and a cartridge lower surface. Shown in FIG. 14A is an exploded top perspective view of a cartridge 10E. In this example, the upper surface is the top surface of a first housing member 50E, and is shown in FIG. 14F. The lower surface is the bottom surface of a second housing member 60E, and is shown in FIG. 14G. The bottom surface is a plain surface having an optical window 83 and a bottom laminate 347E for covering a blister outlet conduit 317E and a transfer conduit 319E (see FIG. 14J), and these elements are explained below.

Housing members 50E and 60E may be held together by a double-sided sticky gasket 100E as shown in FIG. 14A, however, this is a non-limiting example illustrating how the cartridge (comprising a cartridge body having an upper surface and a lower surface) may be manufactured and assembled. For example, the cartridge may comprise a plurality of members and gaskets, the cartridge may be 3-D printed, or the cartridge may be 3-D printed in combination with a plurality of members and gaskets.

Figure 14B:
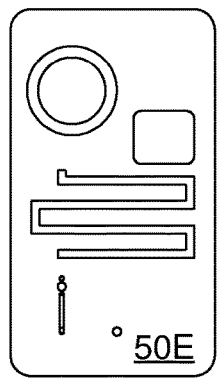
FIG. 14B is a bottom view of the first housing member 50E of the cartridge shown in FIG. 14A.
Figure 14C:
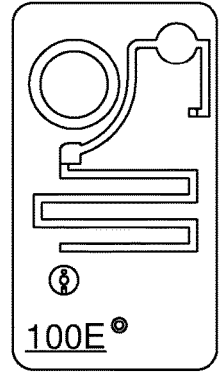
FIG. 14C is the bottom view of the first housing member 50E of the cartridge shown in FIG. 14B, overlaid by and in alignment with a gasket 100E shown in FIG. 14A.
Figure 14D:
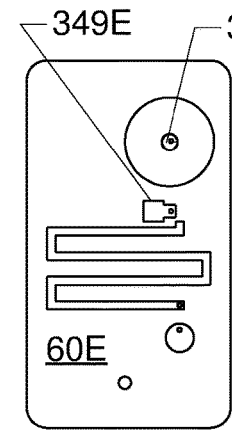
FIG. 14D is a top view of the second housing member 60E of the cartridge shown in FIG. 14A.
Figure 14E:
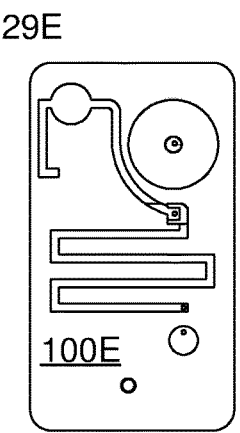
FIG. 14E is the top view of the second housing member 60E shown in FIG. 14D, overlaid by and in alignment with the gasket 100E shown in FIG. 14A.
Figure 14F:
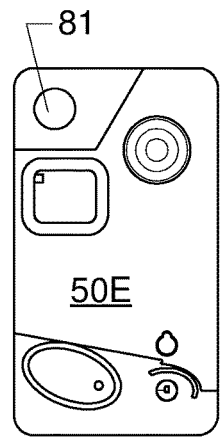
FIG. 14F is a top view of the cartridge 10E shown in FIG. 14A with the cap in an open position.
Figure 14G:
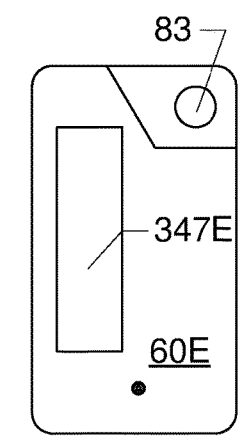
FIG. 14G is a bottom view of the cartridge 10E shown in FIG. 14A.

Shown in FIG. 14B is a bottom view of the first housing member 50E of the cartridge shown in FIG. 14A, and shown in FIG. 14C is the bottom view of the first housing member 50E of the cartridge shown in FIG. 14B, overlaid by and in alignment with a gasket 100E shown in FIG. 14A. The cutouts in the gasket 100E are not labeled because FIGS. 14B-14E illustrate how the gasket cutouts are aligned with the first and second housing members 50E and 60E respectively, and a person having ordinary skill in the art should appreciate that the gasket cutouts could be designed differently without affecting the functionality of the cartridge in any significant way.

Shown in FIG. 14H is a top view of the cartridge 10E with the cap 70E in an open position. This cap operates in a similar manner as cartridge 70B in cartridge 10B (see FIGS. 11A-11K), but there are several differences, as illustrated in FIG. 14S, a perspective top view of the cap, and in FIG. 14T, a perspective bottom view of the cap. The top side 73E of the cap 70E comprises a cap vent 85E (see FIG. 14S), and the underside 75E comprises a cap inlet 78E to a cap mixing chamber 79E (see FIGS. 14P & 14Q). Therefore the cap is a hollow cap having an inlet disposed at the underside and a vent disposed at the top side, and the hollow chamber of the cap functions as a mixing chamber and reservoir for altered or diluted blood. The underside 75E of the cap 70E comprises an inlet 78E to the mixing chamber 79E, and a flat surface 76E surrounding the inlet 78E, for mating with a flat surface 59E of the cartridge inlet portion 57E (see FIG. 14A).

In this example, blood and diluent are mixed in the mixing chamber 79E to provide diluted blood. It is explained below how a metered volume of blood (for example, 20 μL), is mixed with a metered volume of diluent (for example, 180 μL), to provide a 1:10 diluted blood sample. It was previously explained that some manual hemocytometers use a 1:200 diluted blood in order to count red blood cells. A 1:10 diluted blood sample may provide a compromise between 1:200 dilution and no dilution, for counting both red and white blood cells, using a system described in this application. However, other dilutions are within the scope of the present invention.

The diluent is stored in a sealed blister 301E, shown in FIGS. 14A, 14H, 14N. A cross-sectional view of the blister 301E is shown in FIG. 14J. The blister 301E may comprise a dome-shaped top, a flat bottom, and a cavity for containing the diluent. Blisters that may be used in the cartridge described herein are also provided in U.S. 9,470,67320 and CA Pat. No. 2,978,737 (to Samsoondar, which is incorporated herein by reference). In FIG. 14J the blister is shown resting on a compressible member 351E so that the spike 329E can only rupture the bottom portion of the blister when force is applied to the top portion of the blister. The blister window 305E (an opening on the top surface of first housing member 50E; see FIG. 14A) may be covered with a paper label, having perforations along a circle slightly smaller than the diameter of the window 305E, so that the paper label is easily torn by a stepper motor actuator, for example, which may be used to apply force on the blister for rupturing the blister.

After the blister is ruptured, the diluent flows through the hole 331E in the spike 329E, into a diluent holding conduit 303E via a blister outlet conduit 317E (see FIGS. 14H & 14J). A flexible member 313E shown in detail in FIG. 14U is installed in a receptor 349E (see FIGS. 14A & 14J). The flexible member may be made from an elastomeric material, for example, which should not be considered limiting in any way, PDMS (polydimethylsiloxane). In this example, diluent flowing out of the blister outlet conduit 317E cannot flow back into the blister because the pressure closes the flap 315E of the flexible member 313E, and covers receptor 349E.

At the leading end of the diluent holding conduit 303E, a second directional valve element or valve stem 321E (see FIGS. 14V-14Y) is located in the up (open) position, and air is allowed to escape through a diluent vent 325E (see FIG. 14P). An O-ring 337E (see FIGS. 14X & 14Y) provides a seal between the second housing member 60E and the bottom flange of element 321E of the second directional valve.

The analyzer may be programmed to force diluent from the blister 301E until a slight excess of diluent escapes past the diluent vent 325E (i.e. thereby filing or priming the diluent holding conduit 303E). A metered volume of diluent can be sequestered in the diluent holding conduit 303E by pushing the element 321E down (see FIG. 14L). As an example, a stepper motor actuator or a solenoid actuator in the analyzer may be used to move the valve stem 321E. A resilient means, for example a spring, keeps the valve stem in the up position, and the valve stem 321E must be pushed downward in order to keep it in the down position. An example of means for pushing the stem down is a plunger in the analyzer, activated by a stepper motor or a solenoid.

In some embodiments, the position of the valve stem 321E may be controlled using a metal insert in the valve stem, wherein the metal is capable of being attracted to one or more electromagnets installed in the analyzer above the valve element, below the valve element, or a combination thereof. By activating one of the electromagnets, the valve element may be pulled towards the activated electromagnet. When the analyzer comprises an electromagnet above and below the valve elements, a resilient means, for example a spring, may not be required to reverse the valve stem position. With a single electromagnet, a resilient means, such as a spring, may be required to reverse valve stem position. A person skilled in the art would understand that a spring can be installed above or below the valve element. Instead of a spring, other types of resilient means may be used, for example a diaphragm made from a resilient material, and a ball may be used as the valve stem. Some of these examples are described in U.S. Pat. Appl'n Pub. No. US 2019/0224667 (which is incorporated herein by reference).

With the stem 321E the up position (and the diluent holding conduit 303E primed), the blood sample is deposited in the sample storage well 51 through the top opening 53 (FIGS. 14P & 14Q). The blood flow cannot proceed beyond the blood vent 323E (see FIG. 14P) because there is insufficient capillary action to allow the blood to leave the vent 323E.

The valve stem 321E is preferably made from hydrophobic material, for example PTFE (polytetrafluoroethylene), and the sealing surfaces 343E and 345E (see FIGS. 14X & 14Y) may be, for example, a layer of elastomeric material to provide more efficient seals. A hydrophobic stem 321E has the ability to further inhibit movement of blood out of the blood vent 323E. With the leading edge of the blood controlled, the blood volume is metered by skimming off excess blood at the sample storage well inlet 53 when the cap 70E is closed. Therefore, with the valve stem 321E in the up position as shown in FIG. 14P, the cartridge can meter the volumes of both the diluent and the blood. By pushing the stem 321E down, as shown in FIG. 14L, fluid connection between the diluent and the blood is established.

After the fluid connection between the diluent and blood is established, the air bladder may be activated to provide positive air pressure, to push a metered volume of diluent and a metered volume of blood (at the leading end of the blood) into the mixing chamber 79E (see FIG. 14L in conjunction with FIG. 14P) through the cap inlet 78E (see FIG. 14T). The diluent and the blood become mixed as the two flow into the large mixing chamber 79E in the cap 70E. Any trapped air is allowed to rise to the top of the mixing chamber 79E. The analyzer is programmed to provide sufficient pressurized air to ensure all the metered diluent enters the mixing chamber, and air in the mixing chamber escapes through the cap vent 85E (see FIG. 14S). A metered volume of blood may be carried with the much larger volume of diluent (depending on the required dilution factor). By releasing the air bladder, and maintaining the applied pressure, diluted blood is drawn into the optical chamber 13, via the optical chamber inlet conduit 97E and the optical chamber outlet exit conduit 99E (see FIGS. 14H & 14N). The diluted sample in the optical chamber is now ready for sample interrogation.

Alternatively, in place of an air bladder 67E, some cartridges may use an analyzer pump as described for cartridge 10D (see FIGS. 13A-13E), for providing positive and negative pressure.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

I claim:

1. An analyzer for measuring one or more analyte quantities per unit volume of whole or altered blood and quantities of one or more formed elements per unit volume of the whole or altered blood, in a whole or altered blood sample, the analyzer comprising:
    a receptor for receiving a removable cartridge, the removable cartridge comprising an optical chamber configured for receiving the whole blood sample, the optical chamber comprising an upper optical window and a lower optical window and one or both of the upper and lower optical windows is a transparent or a translucent optical window;
    at least one source of interrogating EMR for interrogating at least some of the whole blood sample or altered blood, and producing a first set of emerging EMR and a second set of emerging EMR wherein the receptor positions and aligns the removable cartridge, and defines at least one interrogating EMR path for the interrogating EMR from the at least one source to intersect with at least one of the upper and lower optical windows of the optical chamber of the removable cartridge received within the receptor;

means for communicating, from the removable cartridge as positioned and aligned within the receptor, the first set of emerging EMR to a one-dimensional multi-channel detector and the second set of emerging EMR to a two-dimensional multi-channel detector;

a dispersing element for receiving and dispersing the first set of emerging EMR into its component wavelengths, to produce dispersed EMR, wherein the first set of emerging EMR is communicated to the one-dimensional multi-channel detector via the dispersing element such that the first set of emerging EMR is provided to the one-dimensional multi-channel detector as dispersed EMR;

the one-dimensional multi-channel detector for receiving the dispersed EMR and generating wavelength-specific electrical signals;

an analog to digital converter for receiving the wavelength-specific electrical signals and generating wavelength-specific digital information;

the two-dimensional multi-channel detector for receiving the second set of emerging EMR and generating detector-specific electrical signals;

one of the analog to digital converter and a second analog to digital converter for receiving the detector-specific electrical signals and generating detector-specific digital information; and one or more processors for:
controlling the analyzer;
transforming the wavelength-specific digital information into the one or more analyte quantities per unit volume of whole blood; and
transforming the detector-specific digital information into an image of the one or more formed element quantities per unit volume of whole blood, for counting the one or more formed elements.

2. The analyzer of claim 1, wherein the at least one source of interrogating EMR is one of a polychromatic EMR, a combination of a plurality of monochromatic EMR, and a combination of one or more polychromatic and one or more monochromatic EMR.

3. The analyzer of claim 2, wherein the polychromatic source of EMR is one of an incandescent lamp, a white LED, a ring of LEDs, a bundle of LEDs, a plurality of lasers, and a combination thereof.

4. The analyzer of claim 2, wherein the polychromatic source of EMR encompasses wavelengths within a range of about 300-2,500 nanometers.

5. The analyzer of claim 2, wherein the polychromatic source of EMR encompasses wavelengths within a range of about 400-800 nanometers.

6. The analyzer of claim 1, wherein the means for directing the first set of emerging EMR to the one-dimensional multi-channel detector and the second set of emerging EMR to the two-dimensional multi-channel detector comprises one of a beam splitter or a pivotal mirror, wherein:
the first set of emerging EMR is transmitted through the optical chamber, and the second set of emerging EMR is reflected from the optical chamber;
the first set of emerging EMR is reflected from the optical chamber and the second set of emerging EMR is transmitted through the optical chamber; or
the first set of emerging EMR is reflected from the optical chamber and the second set of emerging EMR is reflected from the optical chamber; and
wherein a first general direction of the first set of emerging EMR and a second general direction of the second set of emerging EMR define an angle less than 90 degrees.

7. The analyzer of claim 6, wherein the beam splitter is selected from one of a bifurcated optical fiber, a plate comprising a partially silvered coating, a plate comprising a dielectric coating, and a partially reflecting prism.

8. The analyzer of claim 1, wherein the analyzer further comprises a magnification system disposed between the receptor and the two-dimensional multi-channel detector.

9. The analyzer of claim 8, wherein the magnification system provides a plurality of magnification settings for optimizing the image formed on the two-dimensional multi-channel detector.

10. The analyzer of claim 1, wherein the one-dimensional multi-channel detector is one of a photodiode linear array and a charge-coupled device (CCD) linear array, and wherein the two-dimensional multi-channel detector is selected from a CCD camera and a complementary metal oxide semiconductor (CMOS) camera.

11. The analyzer of claim 10, wherein the CCD camera or the CMOS camera comprises pixels having a pixel pitch of about 1-10 μm.

12. The analyzer of claim 10, Therein the CCD camera or the CMOS camera comprises pixels having a pixel pitch of less than 4 μm.

13. The system of claim 1, wherein a collimation system is disposed between the source of interrogating EMR and the two-dimensional multi-channel detector.

14. The system of claim 1, wherein a focusing system is disposed between the source of interrogating EMR and the two-dimensional multi-channel detector.

15. The analyzer of claim 1 further comprising an analyzer pump for operating in conjunction with the cartridge, the analyzer pump having a positive pressure mode for generating positive pressure and a negative pressure mode for generating negative pressure, and a hollow needle comprising a first end operatively connected to the analyzer pump, a second end distal to the first end and operatively connected to the first end, the hollow needle further comprising an outer surface, the outer surface for engaging with a sealing member installed in one of a cartridge exit duct of the cartridge and a cartridge air inlet duct of the cartridge.

16. A system comprising the analyzer of claim 1 and the cartridge with the optical chamber placed within the receptor.

17. The system of claim 16, wherein the cartridge further comprises a biosensor chamber having one or more biosensors for generating additional one or more analyte quantities per unit volume of whole blood.

18. The system of claim 16, wherein one of the upper optical window and the lower optical window comprises a reflecting surface for reflecting EMR after the interrogating EMR has penetrated the optical chamber.

19. The system of claim 16, wherein the upper and the lower optical windows are substantially parallel to each other, and the upper and the lower optical windows are spaced apart about 50-200 micrometers.

20. The system of claim 16, wherein an area of the transparent or the translucent optical window is about 1-100 square millimeters.

21. The system of claim 16, wherein the cartridge comprises an upper surface and a lower surface the upper surface defining a sample storage well comprising a top opening, a hingedly attached cap, one of a cartridge vent and a cap vent, one of an air bladder, a cartridge exit and a cartridge air inlet, the sample storage well in fluid communication with the one of a cartridge vent and cap vent, and the one of an air bladder, cartridge exit and a cartridge air inlet, and wherein at least one reagent is disposed between the top opening and one of the cartridge vent, the cartridge exit, and the cartridge air inlet.

22. The system of claim 21, wherein the at east one reagent is one of a hemolyzing reagent and a staining reagent.

23. The system of claim 16, wherein the cartridge further comprises a sealed blister, the sealed blister containing one of a liquid reagent and a diluent, the system further comprising:
   a means for releasing the liquid reagent or the diluent from the sealed blister into the cartridge;
   a means for metering the liquid reagent or the diluent; and
   a means for mixing the liquid reagent or the diluent with the whole blood sample.

24. The cartridge of claim 16, the cartridge further comprising:
   a cartridge body having an upper surface and a lower surface;
   the upper surface defining a sample storage well, the sample storage well comprising a top portion for receiving a blood sample and a bottom portion for releasing at least a portion of the blood sample into the optical chamber;
   a pre-optical chamber conduit for transferring a portion of the blood sample from the sample storage well to the optical chamber;
   a post-optical chamber conduit between the optical chamber and one of a vent and a cartridge exit, the post-optical chamber conduit for receiving excess blood flowing out of the optical chamber;
   one or more reagents disposed in the post-optical chamber conduit, sufficiently far enough from the optical chamber and the vent or the cartridge exit, so that when the blood sample is positioned in the optical chamber a first sample interrogation is performed on unaltered blood, and when the blood sample is mixed with at least some of the one or more reagents to produce an altered blood, a second sample interrogation is performed on the altered blood;
   a cap having a top side and an underside, the cap attached to the cartridge body and movable from a first to a second position;
   the cartridge body further comprising one of:
      A) a positive to negative pressure means, so that when the blood sample is present in the cartridge body and when a positive pressure is applied, at least a portion the blood sample flows in a direction towards the vent, and when a negative pressure is applied at least a portion of the blood sample flows in a direction away from the vent, the positive to negative pressure means comprising:
         one of
            I) an air bladder in the cartridge body for generating the positive and the negative pressure by respectively squeezing and releasing the air bladder; and
            II) a cartridge air inlet duct positioned in the cartridge body and operatively connected to a closed air passage facilitated by a groove set into the upper surface of the cartridge body, a recess set into the underside of the cap, or a combination thereof, the cartridge air inlet duct comprising a sealing member so that when the cartridge is inserted within an analyzer, the sealing member frictionally engages an outer surface of a hollow needle operatively connected with an analyzer pump, and the positive pressure and the negative pressure generated by the analyzer pump are transferable to the cartridge air inlet duct;
         one of:
            an air bladder communication port defined by the upper surface of the cartridge body, wherein the air bladder communication port is operatively connected with the air bladder, and
            an analyzer pump communication port defined by the upper surface of the cartridge body, so that when the cartridge is inserted within the analyzer, the analyzer pump communication port operatively connects with the analyzer pump;
         a flat surface located on the upper surface of the cartridge body, the flat surface of the cartridge body surrounding the top portion of the sample storage well and one of the air bladder communication port and the analyzer pump communication port; and
         a cap flat surface located on the underside of the cap; wherein
         the cartridge is adjustable between an unsealed configuration and a sealed configuration;
         in the unsealed configuration the cap is in the first position and the sample storage well is configured to receive the blood sample; and
         in the sealed configuration the cap is in the second position and a portion of the flat surface of the cartridge body mates with the cap flat surface to form the closed air passage operatively connecting one of the air bladder communication port and the analyzer pump communication port to the sample storage well so that either the positive pressure or the negative pressure is transferable to the sample storage well; and
      B) a negative to positive pressure means so that when the blood sample is present in the cartridge body and when the negative pressure is applied, at least a portion the blood sample flows in a direction towards a cartridge exit duct, and when the positive pressure is applied at least a portion of the blood sample flows in a direction away from the cartridge exit duct, the negative to positive pressure means comprising:
         the cartridge exit duct positioned in the cartridge body and operatively connected to the optical chamber via the post-optical chamber conduit, the cartridge exit duct comprising a sealing member so that when the cartridge is inserted within the analyzer, the sealing member frictionally engages the outer surface of the hollow needle so that the negative pressure and the positive pressure generated by the analyzer pump are transferable to the cartridge exit duct; wherein
         the cartridge is adjustable between an open configuration and a closed configuration;

in the open configuration the cap is in the first position and the sample storage well is configured to receive the blood sample; and in the closed configuration the cap is in the second position and the sample storage well is covered with the cap, the cap further comprising a cap vent so that when the blood sample is positioned within the sample storage well, the blood sample is subjected to atmospheric pressure, so that the negative pressure and the positive pressure are transferable to a leading edge of the blood sample.

25. The cartridge of claim 24, wherein the top portion of the sample storage well comprises a boss for increasing a storage capacity of the sample storage well.

26. The cartridge of claim 25, wherein the cap is one of a hinged cap and a screw-type cap.

27. The cartridge of claim 26, further comprising a conductivity sensor, the conductivity sensor comprising a pair of conductivity electrodes disposed between the optical chamber and one of the vent and the cartridge exit duct, so that when the blood sample is positioned within the cartridge body and the cartridge is positioned within the analyzer, the conductivity sensor detects a location of the leading edge of the blood and communicates with the analyzer to control one of the air bladder and the analyzer pump.

28. The cartridge of claim 24, wherein the cartridge further comprises one of an enlarged cavity disposed near a junction of the bottom portion of the sample storage well and the pre-optical chamber, and a hydrophobic insert disposed near the junction, the sample storage well further comprising internal walls, the internal walls of the sample storage well characterized as being more wettable than a surface of the pre-optical chamber.

29. The cartridge of claim 24, wherein the cartridge further comprises a biosensor chamber, the biosensor chamber disposed between, and in operative communication with the optical chamber and the one of a vent and a cartridge exit duct, and wherein the biosensor chamber comprises one or more biosensors for generating one or more signals used to calculate one or more properties of the blood sample.

30. The system of claim 24, wherein the sample storage well is a sample storage well insert, and the sample storage well insert is inserted in the cartridge body, and wherein the sample storage well insert is more wettable than the cartridge body.

31. The cartridge of claim 16, the cartridge further comprising:

a cartridge body having an upper surface and a lower surface;

a sample inlet portion located on the upper surface, the sample inlet portion comprising:

a sample storage well defined by the upper surface, the sample storage well comprising a top portion for receiving a blood sample and a bottom portion for releasing at least a portion of the blood sample into a pre-optical chamber conduit;

an analyzer pump communication port defined by the upper surface, the analyzer pump communication port in operative communication with an analyzer pump when the cartridge is installed within an analyzer;

a flat surface located on the upper surface of the cartridge body, the flat surface surrounding the top portion of the sample storage well and the analyzer pump communication port;

the pre-optical chamber conduit for transferring at least a portion of the blood from the sample storage well to the optical chamber;

a post-optical chamber conduit for receiving excess blood flowing out of the optical chamber, post-optical chamber conduit in operative communication with the optical chamber and a vent, the vent for modulating blood flow in the cartridge;

a cartridge air inlet duct operatively connected to a closed air passage facilitated by a groove set into the upper surface of the cartridge body, a recess set into the underside of a cap, or a combination thereof the cartridge air inlet duct comprising a sealing member for frictionally engaging an outer surface of an analyzer pump hollow needle so that when the cartridge is installed within the analyzer, pressure from the analyzer pump is transferable to the analyzer pump communication port via the cartridge air inlet duct;

a cap having a top side and an underside, the cap attached to the cartridge body and movable from a first to a second position;

a cap flat surface located on the underside: wherein
the cartridge is adjustable between an unsealed configuration and a sealed configuration;

in the unsealed configuration the cap is in the first position and the sample storage well is configured to receive the blood sample; and in the sealed configuration the cap is in the second position, and a portion of the flat surface of the cartridge body mates with the cap flat surface to form the closed air passage and operatively connecting the analyzer pump communication port to the sample storage well so that when installed within the analyzer, pressure is transferable from the analyzer pump to the sample storage well.

32. The cartridge of claim 31, wherein the top portion of the sample storage well comprises a boss for increasing the sample storage well storage capacity.

33. The cartridge of claim 31, wherein the cap is one of a hinged cap and a screw-type cap.

34. The cartridge of claim 31, further comprising a conductivity sensor, the conductivity sensor comprising a pair of conductivity electrodes disposed between the optical chamber and one of the vent and the cartridge exit duct, so that when the blood sample is positioned within the cartridge body and the cartridge is positioned within the analyzer, the conductivity sensor detects a location of a leading edge of the blood and communicates with the analyzer to control the analyzer pump.

35. The cartridge of claim 31, wherein the cartridge further comprises one of an enlarged cavity disposed near a junction of the bottom portion of the sample storage well and the pre-optical chamber, and a hydrophobic insert disposed near the junction, the sample storage well further comprising internal walls, the internal walls of the sample storage well characterized as being more wettable than a surface of the pre-optical chamber.

36. The cartridge of claim 16, the cartridge further comprising:

a cartridge body having a upper surface and a lower surface;

a sample storage well defined by the upper surface, the sample storage well comprising a top portion for receiving the blood sample and a bottom portion for receiving a metered volume of a diluent and for releasing a diluted blood;

a cartridge flat surface located on the upper surface surrounding the top portion of the sample storage well;

a sealed blister for containing the diluent, and means for releasing the diluent into a diluent holding conduit, the sealed blister located in the cartridge body;

a hinged hollow cap attached to the cartridge body, the hinged hollow cap movable from a first to a second position, the hinged hollow cap comprising a top side, the top side defining a cap vent;

an underside, the underside defining an inlet, the inlet surrounded by a cap flat surface;

a leading edge, so that when the cap flat surface is frictionally engaged with the cartridge flat surface and moved from the first to the second position, and when blood is present in the sample storage well, the leading edge skims off excess blood projecting out of the top portion of the sample storage well;

means for metering a volume of blood;

means for metering the volume of the diluent;

means for mixing the volume of the blood and the volume of the diluent; and the optical chamber in fluid communication with the bottom portion, the optical chamber for receiving the diluted blood for sample interrogation.

* * * * *